(12) United States Patent
Kisseleva et al.

(10) Patent No.: US 10,233,240 B1
(45) Date of Patent: Mar. 19, 2019

(54) METHODS FOR TREATING CHOLESTATIC LIVER FIBROSIS

(71) Applicant: The Regents of the University of California, Oakland, CA (US)

(72) Inventors: Tatiana Kisseleva, La Jolla, CA (US); David Brenner, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 43 days.

(21) Appl. No.: 14/279,245

(22) Filed: May 15, 2014

Related U.S. Application Data

(63) Continuation-in-part of application No. 13/450,400, filed on Apr. 18, 2012, now abandoned.

(60) Provisional application No. 61/476,556, filed on Apr. 18, 2011.

(51) Int. Cl.

| | |
|---|---|
| *C07K 16/28* | (2006.01) |
| *C12N 15/113* | (2010.01) |
| *A61K 45/06* | (2006.01) |
| *A61K 47/48* | (2006.01) |
| *A61K 39/395* | (2006.01) |
| *A61K 31/7088* | (2006.01) |
| *G01N 33/50* | (2006.01) |

(52) U.S. Cl.
CPC .......... *C07K 16/28* (2013.01); *A61K 31/7088* (2013.01); *A61K 39/3955* (2013.01); *A61K 45/06* (2013.01); *A61K 47/48* (2013.01); *C12N 15/113* (2013.01); *C12N 15/1138* (2013.01); *G01N 33/5091* (2013.01); *G01N 2800/085* (2013.01)

(58) Field of Classification Search
None
See application file for complete search history.

(56) References Cited

U.S. PATENT DOCUMENTS

| | | | | |
|---|---|---|---|---|
| 8,206,710 | B2 * | 6/2012 | Ebel | ........................ C07K 16/30 424/133.1 |
| 2006/0160867 | A1 | 7/2006 | Freedman | |

OTHER PUBLICATIONS

Rosenbloom et al. Narrative review: Fibrotic diseases:cellular and molecular mechanisms and novel therapies. Annals of Internal Medicine. 2010; 152:159-166.*
Wynn et al. Mechanism of fibrosis: therapeutic translation for fibrotic disease. Nature Medicine. 2012; 18(7):1028-1040.*
Zolak et al. Pleural mesothelial cells in the pathogenesis of idiopathicpulmonary fibrosis. American Journal of Respiratory and Critical Care Medicine, 2012; 185: supp. Abbstract A5559.*
Bowie et al. Deciphering the Message in Protein Sequences: Tolerance to Amino Acid Substitutions. Science, 1990, 247:1306-1310.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. Journal of Cell Biology; 111:2129-2138, 1990.*
Lazar et al. Transforming Growth Factor alpha: Mutation of Aspartic Acid 47 and Leucine 48 Results in Different Biological Activities. Molecular Cellular Biology, 8:1247-1252, 1988.*
Aagaard et al. RNAi Therapeutics: Principles, Prospects and Challenges. Advanced Drug Delivery Reviews 59 (2007) 75-86.*
Warzocha et al. Antisense strategy: biological utility and prospects in the treatment of hematological malignancies. Leukemia and Lymphoma, 24(3-4): 267-281.*
Vajdos et al. Comprehensive Functional Maps of the Antigenbinding Site of an Anti-ErbB2 Antibody Obtained with Shotgun Scanning Mutagenesis. Journal of Molecular Biology Jul. 5, 2002;320(2):415-28 at 416.*
Brown et al. Tolerance to Single, but Not Multiple, Amino Acid Replacements in Antibody V, CDR2. Journal of Immunology, May 1996;156(9):3285-91 at 3290.*
Paul. Fundamental Immunology, 3rd Edition, Raven Press, New York, Chapter 8, pp. 292-295, 1993.*
MacCallum et al. Antibody-antigen Interactions: Contact Analysis and Binding Site Topography. Journal of Molecular Biology, 262:732-745, 1996.*
Casset et al. A peptide mimetic of an anti-CD4 monoclonal antibody by rational design. Biochemical and Biophysical Research Communications, 307:198-205, 2003.*
Vajdos et al. Comprehensive Functional Maps of the Antigenbinding Site of an Anti-ErbB2 Antibody Obtained with Shotgun Scanning Mutagenesis. Journal of Molecular Biology, Jul. 5, 2002;320(2):415-28.*
Fundamental Immunology 242 (William E. Paul, M.D. ed., 3d ed. 1993 (Year: 1993).*
Galli et al. "Antidiabetic thiazolidinediones inhibit collagen synthesis and hepatic stellate cell activation in vivo and in vitro" Gastroenterology. 122(7) :1924-1940, 2002.
Taimr et al. Activated stellate cells express the TRAIL receptor-2/ death receptor-5 and undergo TRAIL-mediated apoptosis. Hepatology. 37:87-95, 2003.
Eitner et al. PDGF-C is a proinflammatory cytokine that mediates renal interstitial fibrosis. Journal of American Society of Nephrologist. 19:281-289, 2008.
Kamada et al. Enhanced carbon tetrachloride-induced liver fibrosiss in mice lacking adiponectin. Gastroenterology. 2003; 125 (6): 1796-1807.
Mao et al. HSP72 attenuates renal tubular cell apoptosis and interstitial fibrosis in obstructive nephropathy. American Journal of Physiology Renal Physiology; 295: F202-F214, 2008.
Jeong et al. "STAT1 inhibits liver fibrosis in mice by inhibiting stellate cell proliferation and stimulating NK cell cytotoxicity." Hepatology. 44:1441-1451, 2006.

(Continued)

*Primary Examiner* — Sandra E Dillahunt
(74) *Attorney, Agent, or Firm* — Greer, Burns & Crain Ltd.; Gregory P. Einhorn

(57) ABSTRACT

Provided are methods of treating fibrotic conditions in a subject by the identification of specific subsets of fibrogenic myofibroblasts, such as portal fibroblasts expressing mesothelin, and diagnostic methods useful for determining fibrosis, and the prognosis of fibrosis.

21 Claims, 32 Drawing Sheets

Specification includes a Sequence Listing.

(56) References Cited

OTHER PUBLICATIONS

Myung et al. Heat shock protein 90 inhibtor induces apoptosis and attenuates activation of hepatic stellate cells. Journal of Pharmacology and Experimental Therapeutics. 330(1):276-282, 2009).

Tanaka et al. Heat shock protein 70 protects against bleomycin-induced pulmonary fibrosis in mice. Biochemical Pharmacology. 2010; 80: 920-931.

Rodriguez-Vilarrupla et al. PPAR-alpha activation reduces portal pressure and amerliorates endothellial dysfunction in cirrhosis. Journal of Hepatology 52 (S1):S9, Apr. 2010.

* cited by examiner

FIG. 2
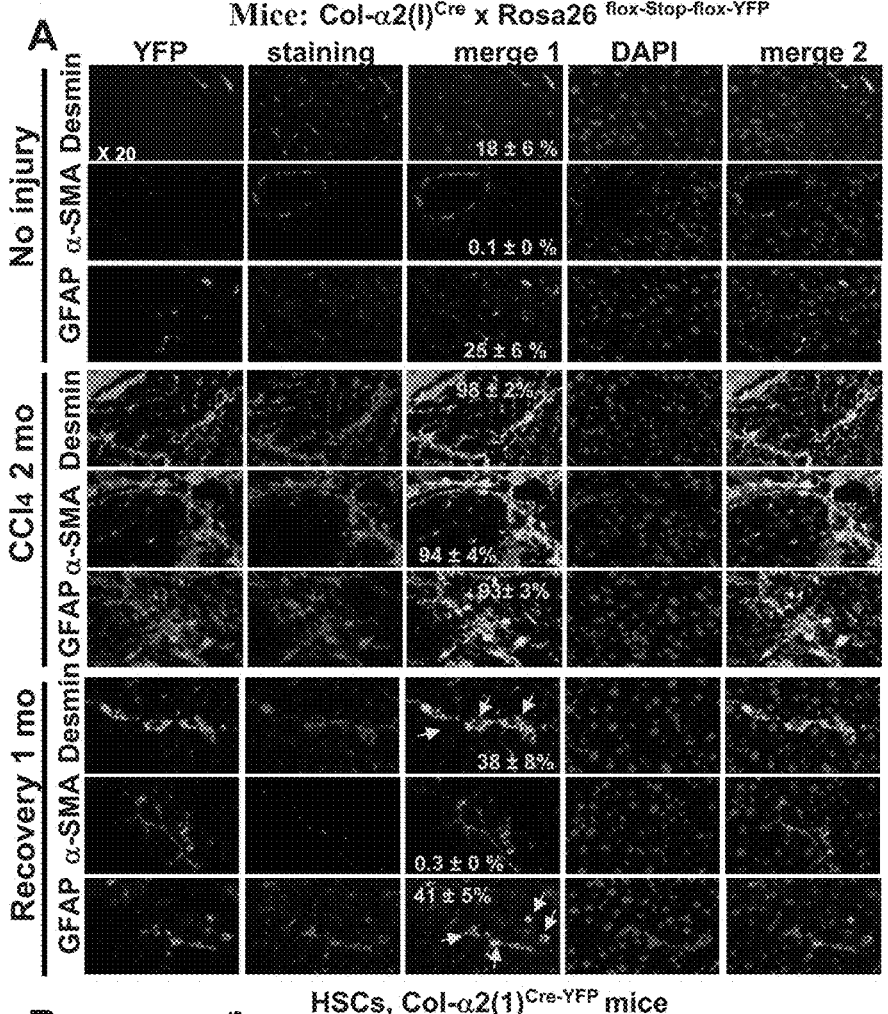
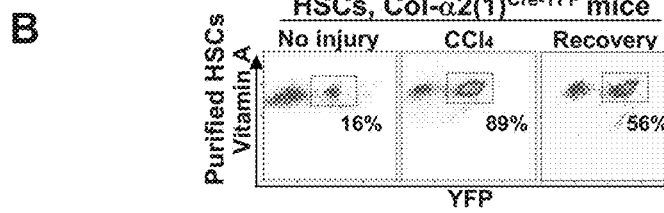
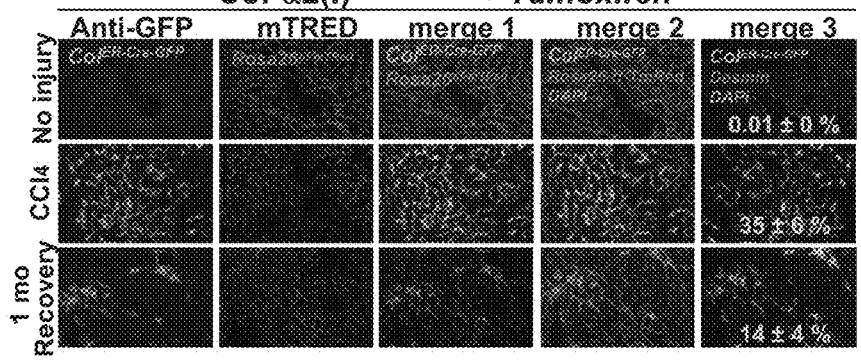

FIG. 4
A
Mice:
Col-α2(I)$^{Cre}$ x Rosa26$^{flox-Stop-flox-YFP}$
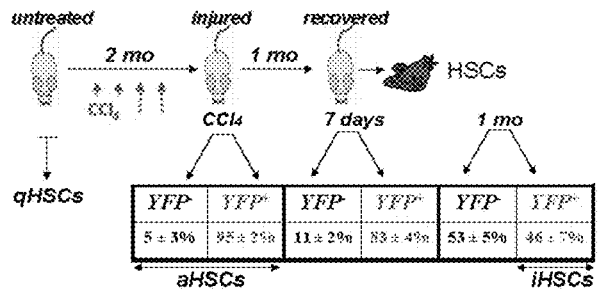
B
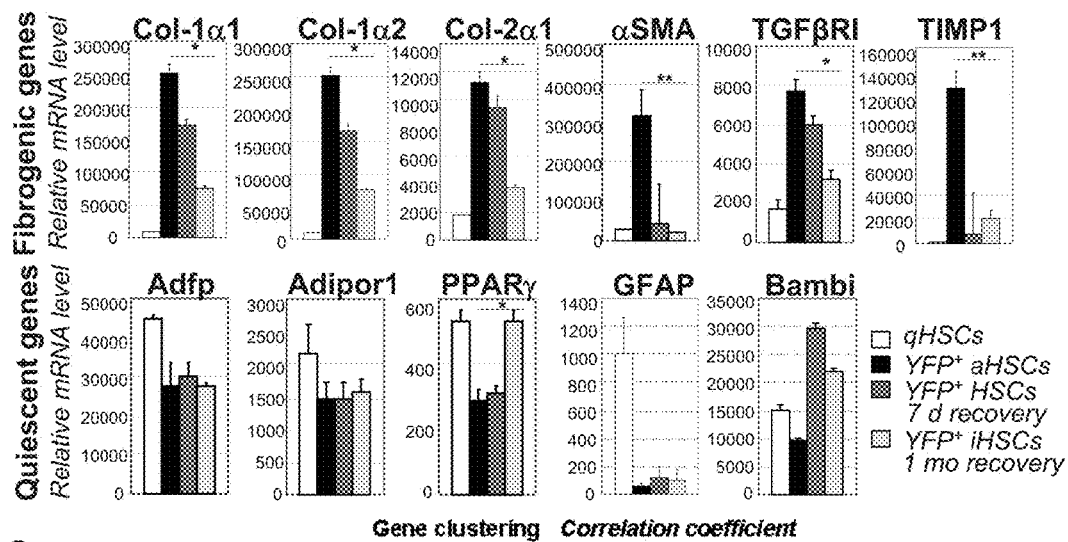
C
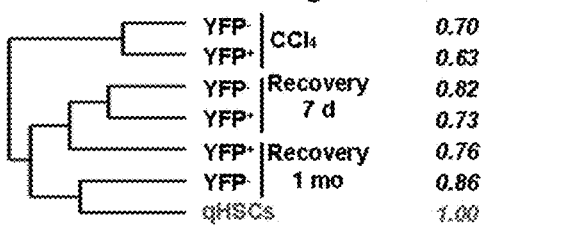
D
| SIGNATURE GENES : | | | |
|---|---|---|---|
| Maximum ↑ YFP⁺ iHSCs 1 mo | Fold | Maximum ↑ YFP⁺ HSCs 7 d | Fold * |
| Cathepsin S | 85 | Keratin 20 | 14 |
| CD74 | 66 | Hspa1a | 10 |
| MHC class II (H2-Ab1) | 42 | Hspa1b | 12 |
| CXCL1 | 3.5 | Glypican 3 (Gpc3) | 5.5 |
| CD52 | 31 | Calpain 6 | 4 |
| CCL4 | 31 | midkine | 3 |
| CD83 | 29 | MMP2 | 3 |
| Integrin α X (Itgax) | 18 | Cyclin G2 (Ccng2) | 3.6 |
| Lectin (Lgals3) | 12 | PPARγc1a | 2.7 |
| CXCL10 | 11 | Hspb2 | 2 |

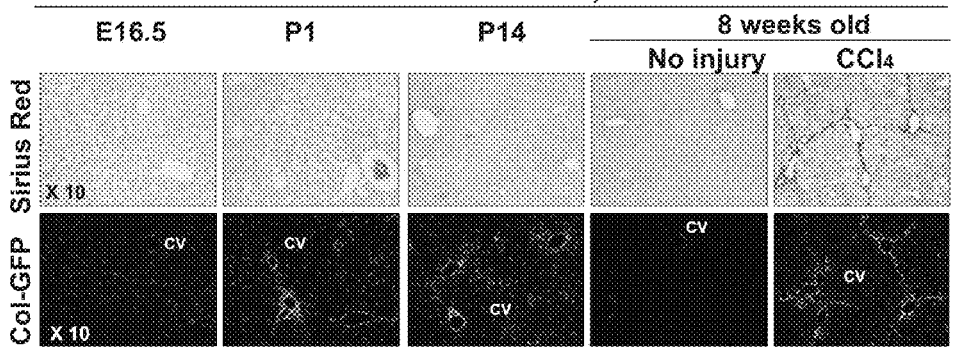
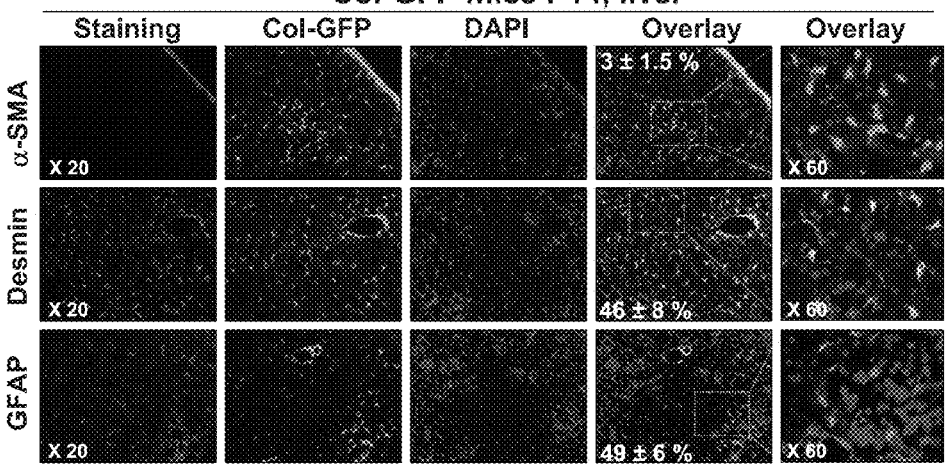
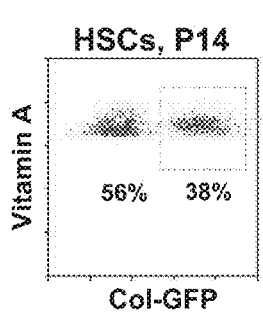
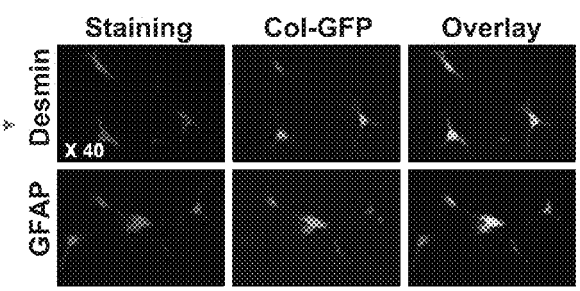
FIG. 11

FIG. 12
Mice: *Tamoxifen* inducible Col-α2(I)$^{ER-Cre}$ x Rosa26$^{flox-mTRed-Stop-flox-GFP}$
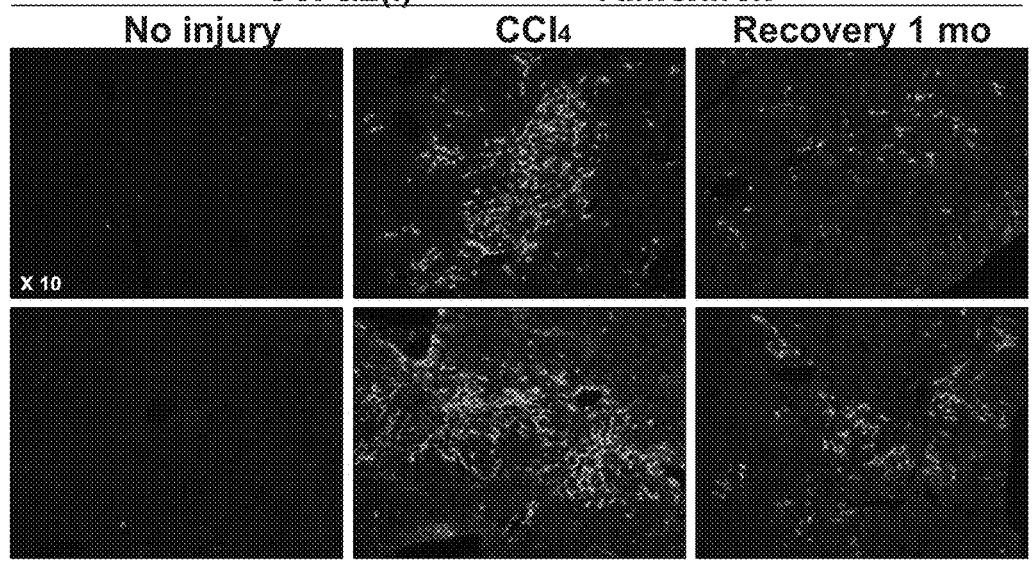
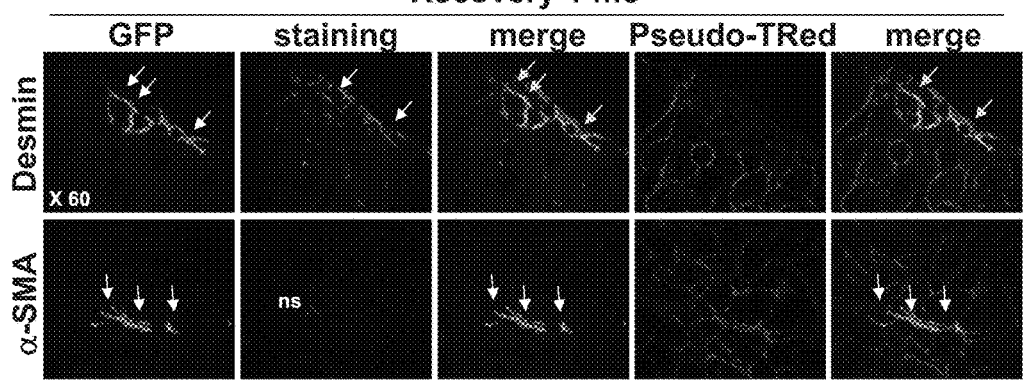

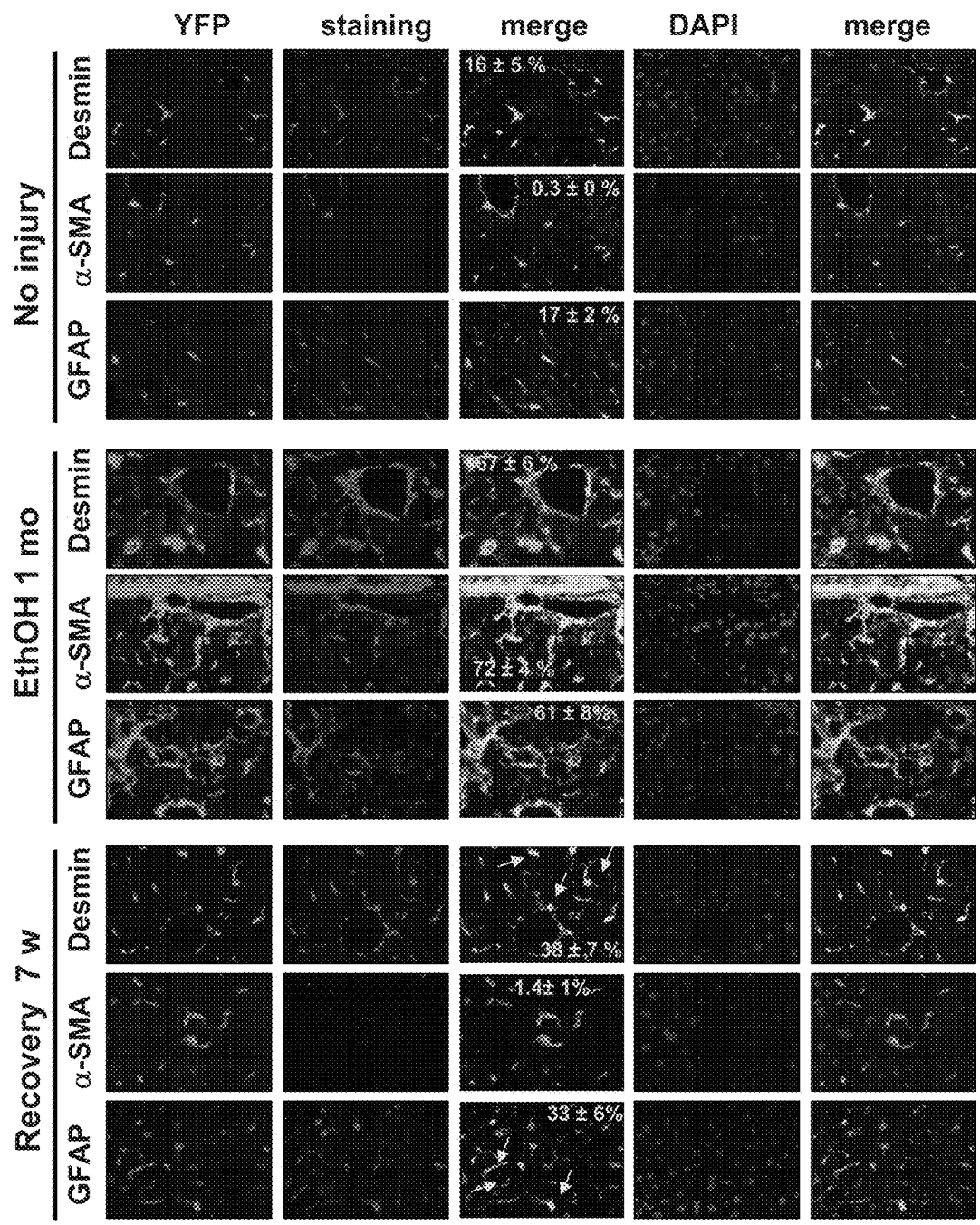
FIG. 14 (cont. 2/3)

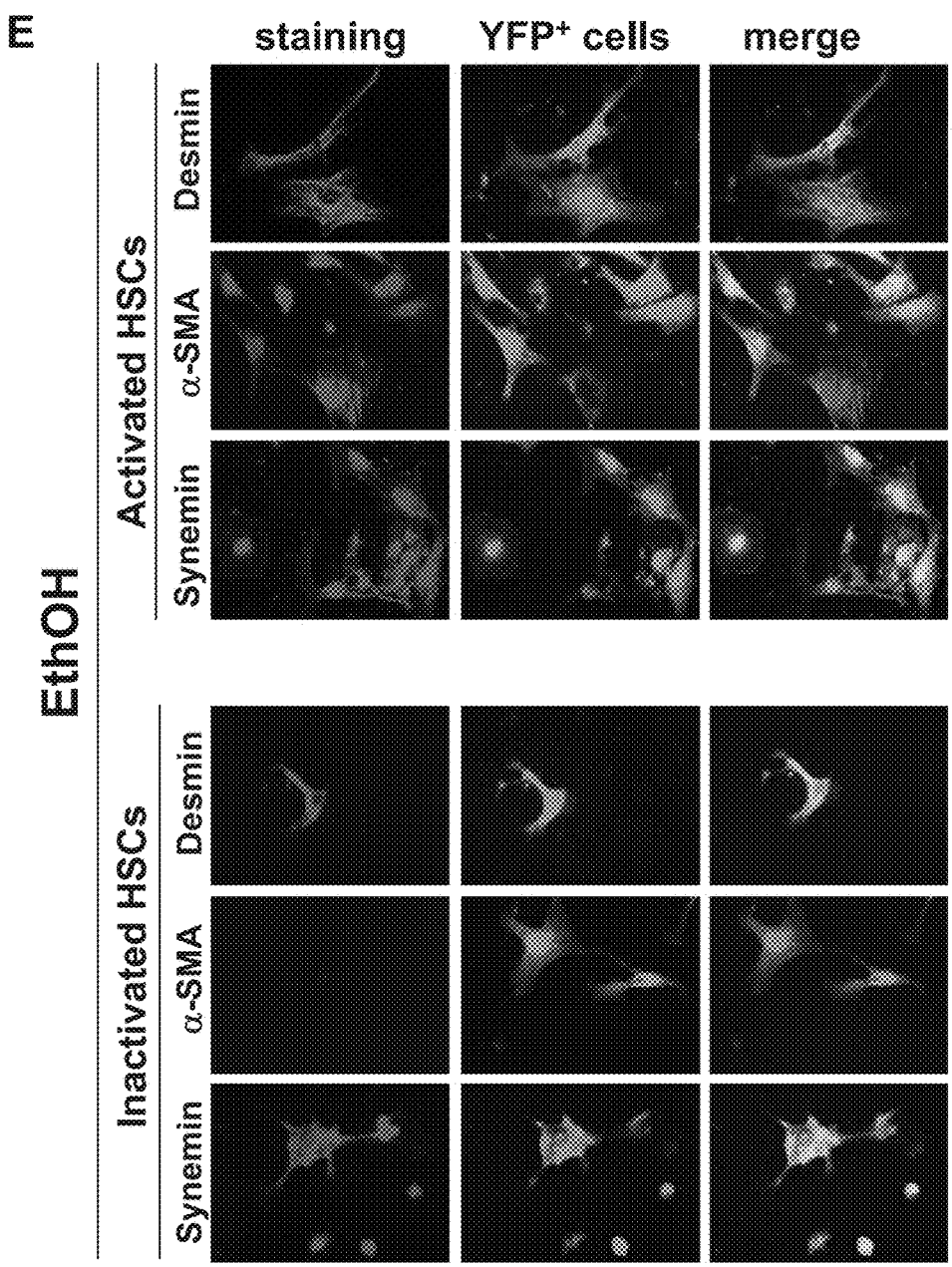
FIG. 14 (cont. 3/3)

A
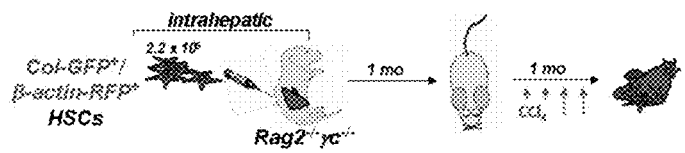
| Rag2$^{-/-}$γc$^{-/-}$ mice | № mice | Engraftment, % | RFP$^+$GFP$^+$ cells, whole liver | |
|---|---|---|---|---|
| | | | No injury | CCl4 |
| qHSCs | 8 | 50% | ± | + |
| HSCs, 7d | 14 | 78% | + | +++ |
| HSCs, 1 mo | 10 | 70% | + | ++ |
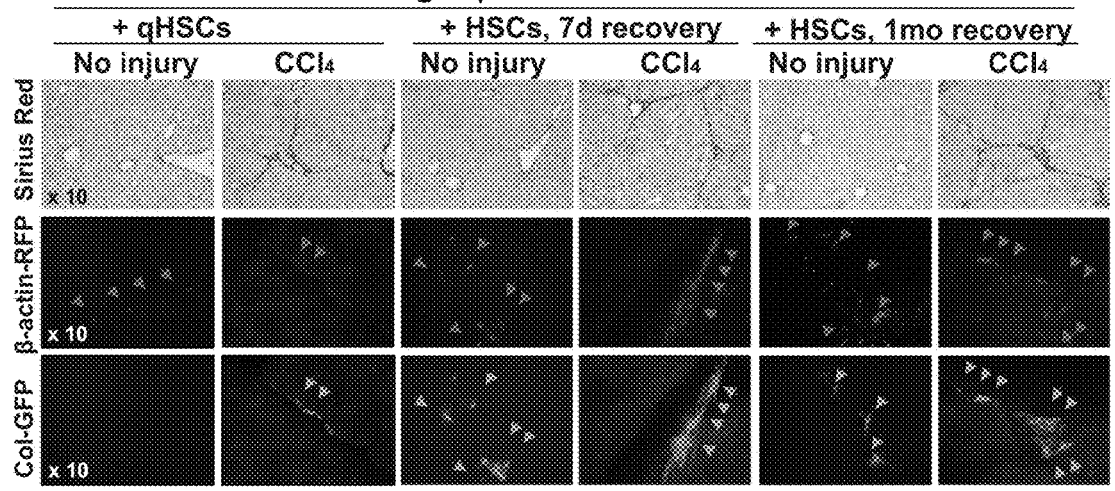
B
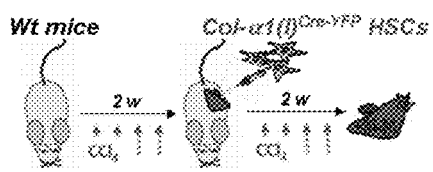
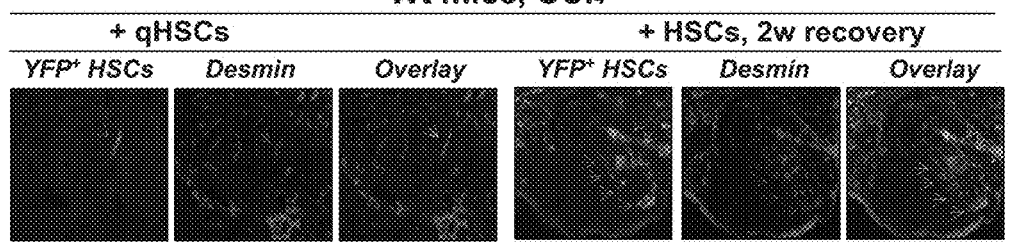
FIG. 16

FIG. 17
A  Mice: Col-α1(I)^Cre x Rosa26^flox-Stop-flox-YFP x Col-α1(I)-GFP mice
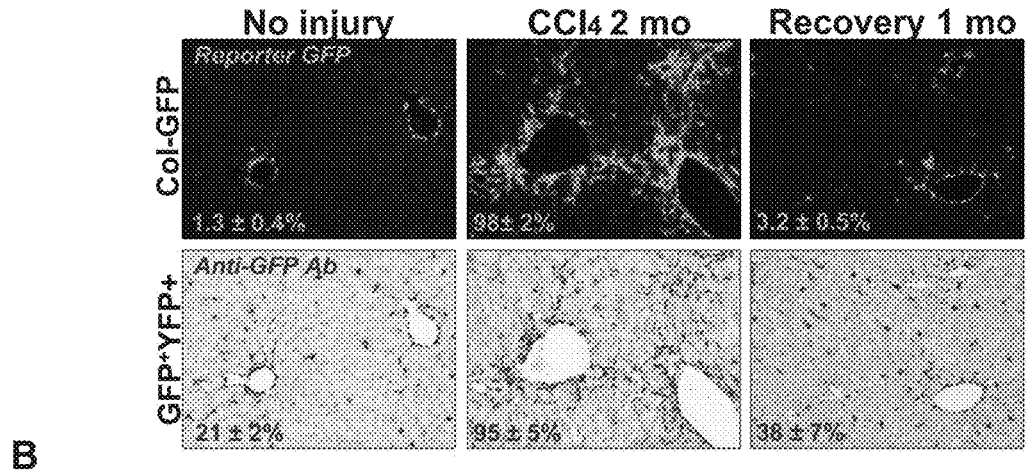
B
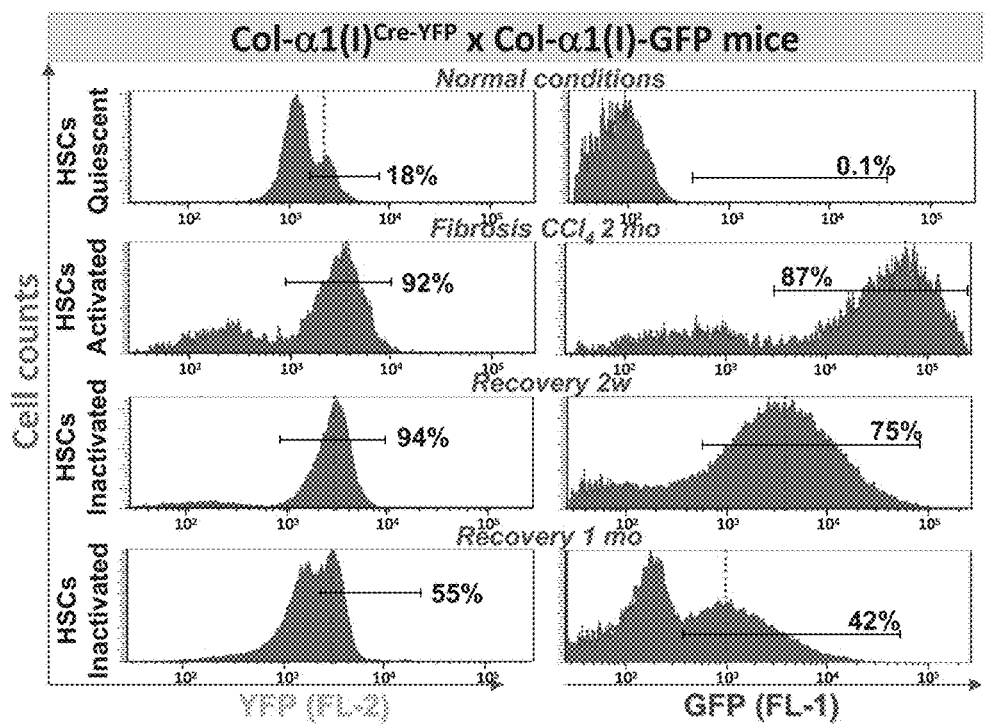
| Genetically labeled HSCs, mean fluorescent intensity | | | | |
|---|---|---|---|---|
| Mice: | Quiescent | Activated | Inactivated 2w | Inactivated 1 mo |
| Col1-α(I)^Cre-YFP | 2300 ± 30 | 3300 ± 155 | 2900 ± 120 | 2800 ± 170 |
| Col-α1(I)-GFP | 100 ± 30 | 60000 ± 3000 | 3900 ± 360 | 990 ± 110 |

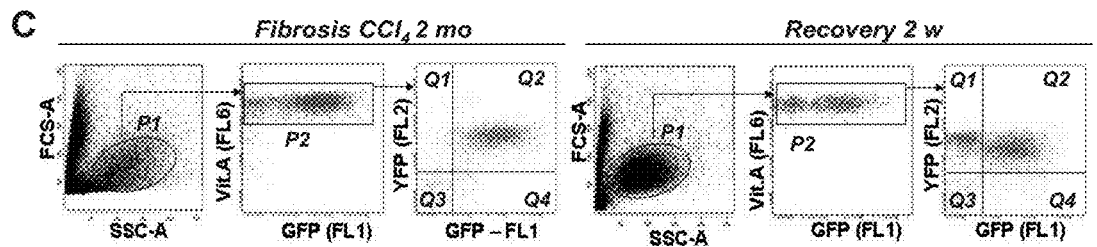
FIG. 17 (cont.)
FIG. 18
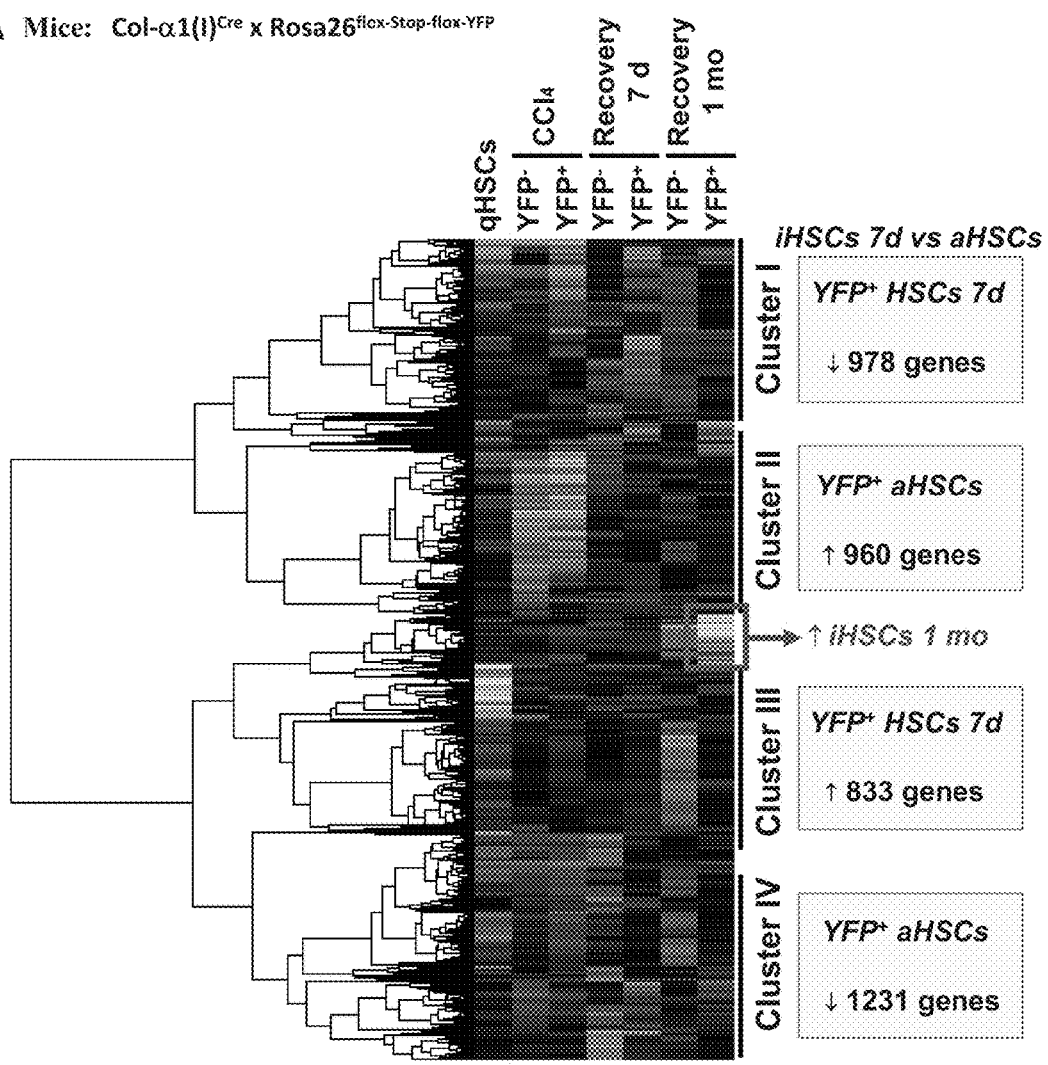

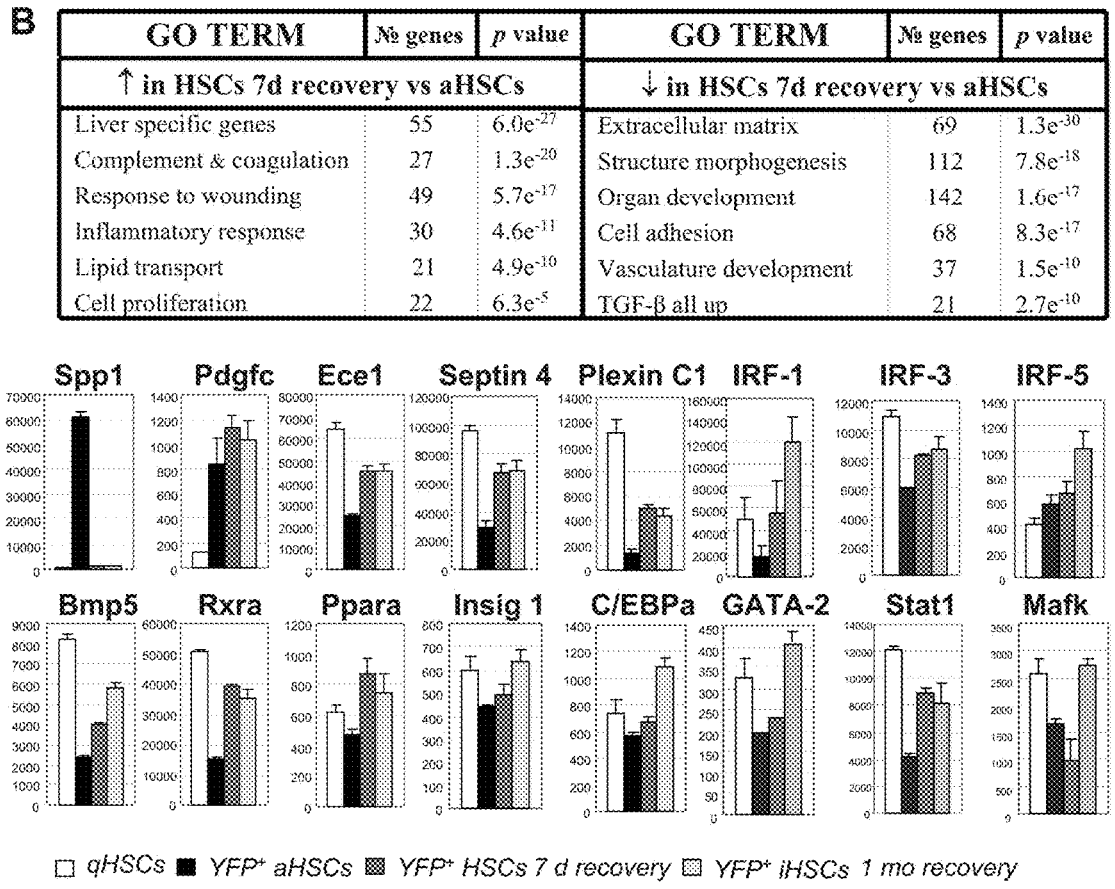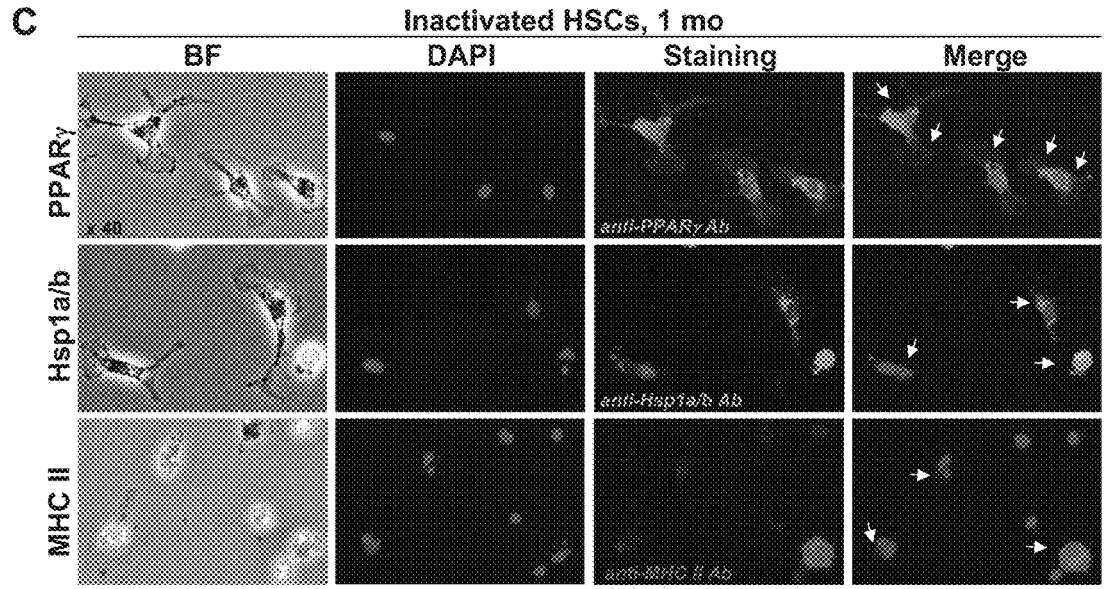
FIG 18. (cont. 2/4)

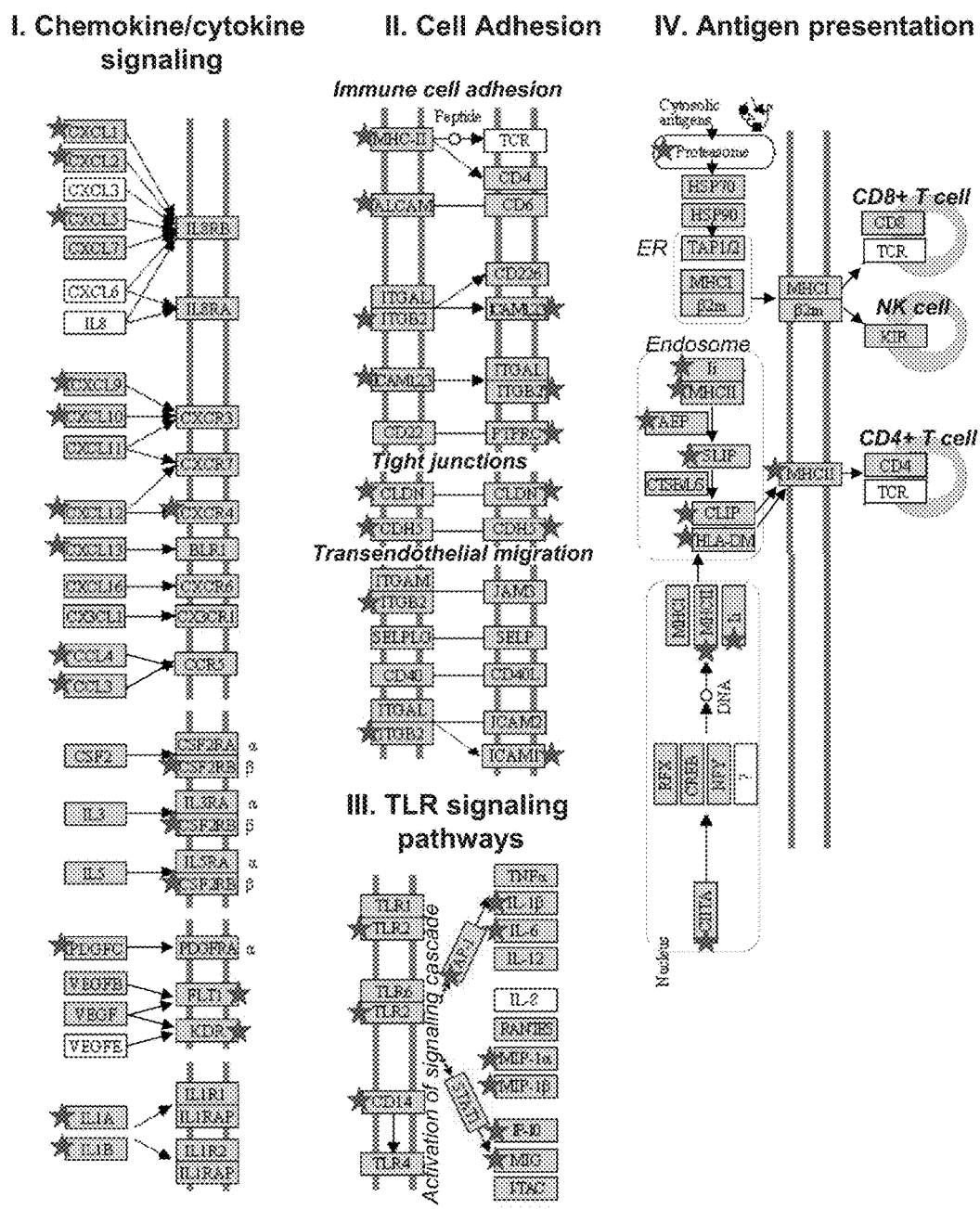
FIG. 18 (cont. 3/4)

E *Pathways upregulated in YFP+ HSCs after 7 days recovery*
I. ECM-Receptor interaction
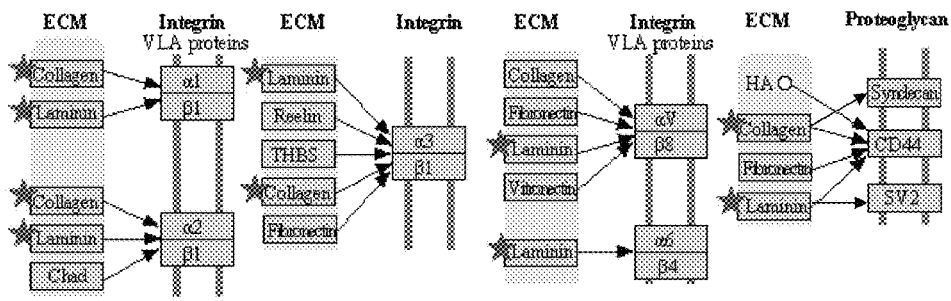
II. Signaling pathways in cancer
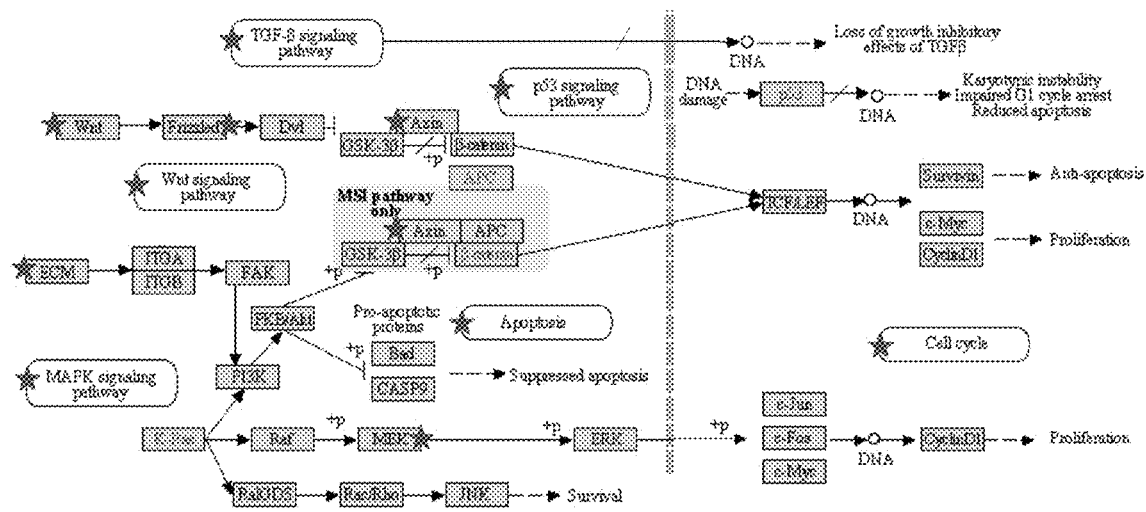
FIG. 18 (cont. 4/4)

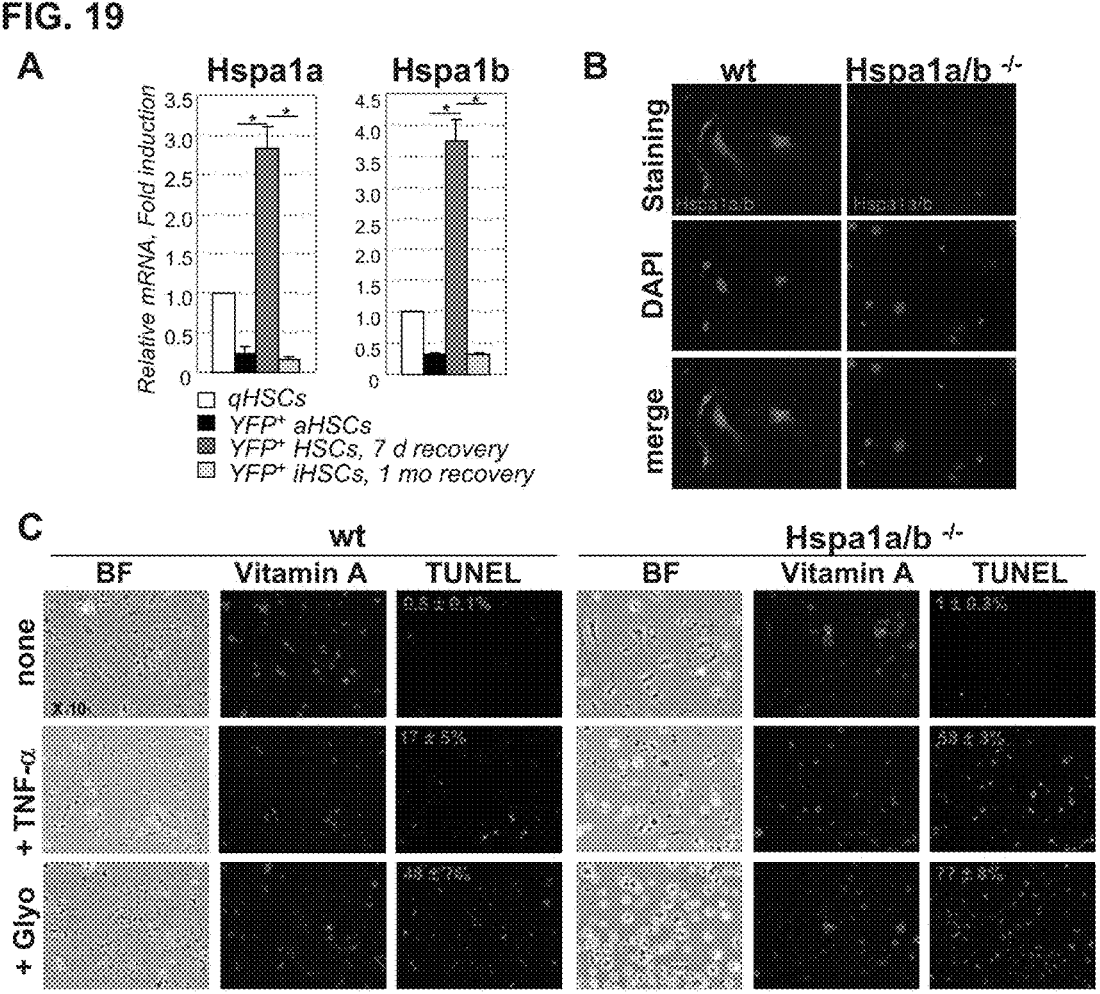

A

| SIGNATURE GENES | | SIGNATURE GENES | |
|---|---|---|---|
| Maximum ↑ PF (BDL) | Fold | Maximum ↑ PF (BDL) | Fold |
| Calcitonin a (Calca) | 48 | Mapk13 | 5.8 |
| Mesothelin (msln) | 28 | Integrin β4 (Itgb4) | 5.5 |
| Uroplakin 1β | 22 | CD55 | 5.3 |
| Frizzled-related protein 4 (Sfrp4) | 21 | IL-20Ra | 4.5 |
| Basonuclin 1 (Bnc1) | 18 | Gremlin 1 (Grem1) | 4.2 |
| Proteoglycan 4 (Prg4) | 18 | FGF9 | 4.1 |
| Asporin (aspn) | 14 | Elastin microfibril interfacer Emilin2 | 3.8 |
| Glipican 3 (Gpc3) | 12 | CD109 | 3.6 |
| IL-18R-1 | 11 | Fibulin 1 (Fbln1) | 3.6 |
| Vitrin (Vit) | 9.9 | S100a4 (FSP-1) | 3.4 |
| CD200 | 9.3 | NADPX oxidase 4 (Nox4) | 3.3 |
| Thrombospondin 4 (Thbs4) | 7.7 | Elastin (Eln) | 2.8 |
| Bcam | 7.3 | Thy1 (CD90) | 1.8 |
| Claudin 10 (Cldn 10) | 7.0 | Cytoglobin | 0.5 |

B

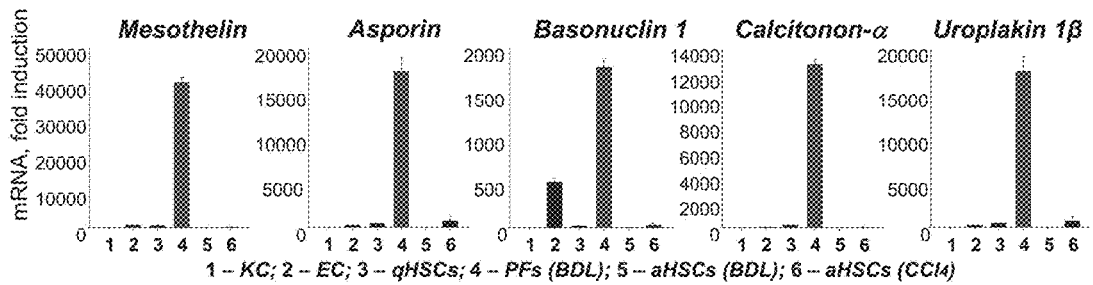

1 — KC; 2 — EC; 3 — qHSCs; 4 — PFs (BDL); 5 — aHSCs (BDL); 6 — aHSCs (CCl4)

FIG. 20 (1/2)

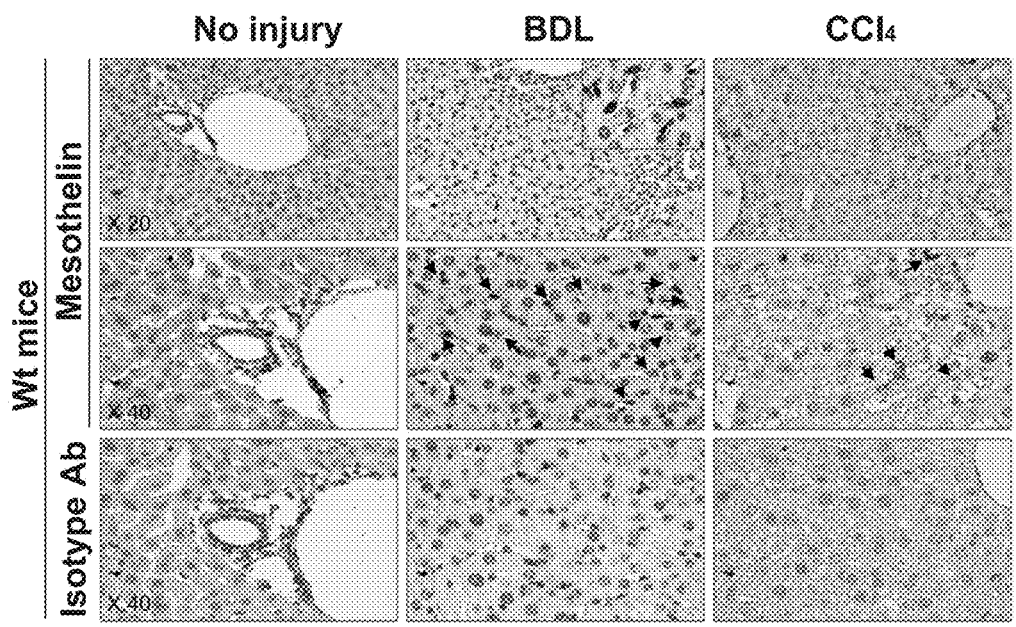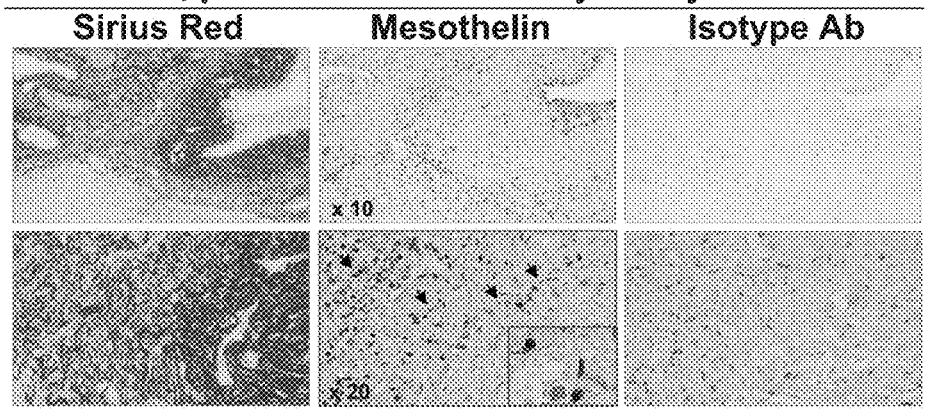
FIG. 20 (2/2)

SEQUENCE LISTING

<160> NUMBER OF SEQ ID NOS: 12

<210> SEQ ID NO 1
<211> LENGTH: 8
<212> TYPE: PRT
<213> ORGANISM: artificial sequence
<220> FEATURE:
<223> OTHER INFORMATION: synthetic peptide

<400> SEQUENCE: 1

Gly Tyr Ser Ile Asn Thr Tyr Tyr
1               5

<210> SEQ ID NO 2
<211> LENGTH: 7
<212> TYPE: PRT
<213> ORGANISM: artificial sequence
<220> FEATURE:
<223> OTHER INFORMATION: synthetic peptide

<400> SEQUENCE: 2

Ile Asn Pro Ser Gly Val Thr
1               5

<210> SEQ ID NO 3
<211> LENGTH: 13
<212> TYPE: PRT
<213> ORGANISM: artificial sequence
<220> FEATURE:
<223> OTHER INFORMATION: synthetic peptide

<400> SEQUENCE: 3

Ala Arg Trp Ala Leu Trp Gly Asp Phe Gly Met Asn Val
1               5                   10

<210> SEQ ID NO 4
<211> LENGTH: 6
<212> TYPE: PRT
<213> ORGANISM: artificial sequence
<220> FEATURE:
<223> OTHER INFORMATION: synthetic peptide

<400> SEQUENCE: 4

Glu Gly Ile Tyr His Trp
1               5

<210> SEQ ID NO 5
<211> LENGTH: 3
<212> TYPE: PRT
<213> ORGANISM: artificial sequence
<220> FEATURE:
<223> OTHER INFORMATION: synthetic peptide

<400> SEQUENCE: 5

Lys Ala Ser
1

<210> SEQ ID NO 6
<211> LENGTH: 9
<212> TYPE: PRT
<213> ORGANISM: artificial sequence
<220> FEATURE:
<223> OTHER INFORMATION: synthetic peptide

<400> SEQUENCE: 6

Gln Gln Tyr Ser Asn Tyr Pro Leu Thr
1               5

```
<210> SEQ ID NO 7
<211> LENGTH: 8
<212> TYPE: PRT
<213> ORGANISM: artificial sequence
<220> FEATURE:
<223> OTHER INFORMATION: synthetic peptide

<400> SEQUENCE: 7

Gly Phe Thr Phe Ser Ser Tyr Ala
1               5

<210> SEQ ID NO 8
<211> LENGTH: 8
<212> TYPE: PRT
<213> ORGANISM: artificial sequence
<220> FEATURE:
<223> OTHER INFORMATION: synthetic peptide

<400> SEQUENCE: 8

Ile Ser Gly Ser Gly Gly Ser Thr
1               5

<210> SEQ ID NO 9
<211> LENGTH: 10
<212> TYPE: PRT
<213> ORGANISM: artificial sequence
<220> FEATURE:
<223> OTHER INFORMATION: synthetic peptide

<400> SEQUENCE: 9

Val Arg Gly Gly Ala Leu Gly Phe Asp Asn
1               5                   10

<210> SEQ ID NO 10
<211> LENGTH: 9
<212> TYPE: PRT
<213> ORGANISM: artificial sequence
<220> FEATURE:
<223> OTHER INFORMATION: synthetic peptide

<400> SEQUENCE: 10

Thr Ser Asn Ile Gly Ser Asn Val Val
1               5

<210> SEQ ID NO 11
<211> LENGTH: 3
<212> TYPE: PRT
<213> ORGANISM: artificial sequence
<220> FEATURE:
<223> OTHER INFORMATION: synthetic peptide

<400> SEQUENCE: 11

Tyr Asp Asp
1

<210> SEQ ID NO 12
<211> LENGTH: 11
<212> TYPE: PRT
<213> ORGANISM: artificial sequence
<220> FEATURE:
<223> OTHER INFORMATION: synthetic peptide

<400> SEQUENCE: 12

Ser Ala Trp Asp Asp Ser Leu Asn Ala Trp Val
1               5                   10
```

METHODS FOR TREATING CHOLESTATIC LIVER FIBROSIS

CROSS REFERENCE TO RELATED APPLICATIONS

This application is a continuation-in-part of and claims the benefit of priority to U.S. Ser. No. 13/450,400, filed Apr. 18, 2012, which claims the benefit of priority to U.S. Provisional Application Ser. No. 61/476,556, filed Apr. 18, 2011, all of which are incorporated herein by reference in their entireties, including all figures.

STATEMENT OF GOVERNMENT SUPPORT

This invention was made with government support under grant nos. AA011999 and DK099205 awarded by the National Institutes of Health. The government has certain rights in the invention.

FIELD OF THE INVENTION

The present invention is in the field of therapeutics and diagnostics related to antifibrotic therapy in animals, such as humans.

BACKGROUND OF THE DISCLOSURE

Hepatic fibrosis is the outcome of many chronic liver diseases, including cholestatic liver injury (primary sclerosing cholangitis (PSC), primary biliary cirrhosis (PBC), secondary biliary cirrhosis (SBC)) and hepatotoxic injury (hepatitis B virus (HBV), hepatitis C virus (HCV), alcoholic liver disease and non-alcoholic steatohepatitis (NASH)) (1). Hepatic fibrosis results from deregulation of wound healing with accumulation of extracellular matrix (ECM), including collagen type I, leading to scar formation. Several early events play an important role in the pathogenesis of liver fibrosis, including damage to hepatocytes, release of TGF-β1, the major fibrogenic cytokine, recruitment of inflammatory cells, induction of reactive oxygen species (ROS), and activation of ECM producing myofibroblasts, which are not present in the normal liver (1, 37). Activation of myofibroblasts is a critical step in liver fibrosis, and, therefore, myofibroblasts represent a primary target for antifibrotic therapy.

Fibrogenic myofibroblasts are cells responsible for collagen production and making the tissues fibrotic, the process associated with tissue destruction in organs capable of developing fibrosis, such as heart, lung, liver, kidney and skin diseases. Chronic liver injury of any etiology produces fibrosis as a result of deregulation of the normal healing process with massive accumulation of extracellular matrix (ECM), including type I collagen (ColI)(1). Myofibroblasts are $ColI^+$ α-smooth muscle actin $(α-SMA)^+$ cells that produce the ECM scar in fibrosis. One of the most important concepts in clinical and experimental liver fibrosis is reversibility. Removal of the etiological source of the chronic injury in patients (e.g. HBV, HCV, biliary obstruction, or alcohol) and in rodents ($CCl_4$ or bile duct ligation) produces regression of liver fibrosis and is associated with decreased cytokine and ECM production, increased collagenase activity, and the disappearance of myofibroblasts (1, 2). During regression of fibrosis, some myofibroblasts undergo senescence (3) and apoptosis (2). However, the number of apoptotic myofibroblasts and the fate of the remaining myofibroblasts in the recovering liver is unknown.

The cells of origin of hepatic myofibroblasts are unresolved, and perhaps the fibrosis induced by different types of liver injury results from different fibrogenic cells. Hepatic myofibroblasts may originate from bone marrow-derived mesenchymal cells and fibrocytes, but only a small contribution of bone marrow (BM)-derived cells to the myofibroblast population has been detected in experimental liver fibrosis (48, 57-58). Another potential source of myofibroblast is epithelial-to-mesenchymal transition (EMT), in which epithelial cells acquire a mesenchymal phenotype and may give rise to fully differentiated myofibroblasts. However, recent cell fate mapping studies have failed to detect any hepatic myofibroblasts originating from hepatocytes, cholangiocytes, or epithelial progenitor cells (1, 59-63). Thus, the major sources of myofibroblasts in liver fibrosis are the endogenous liver mesenchymal cells, which consist of portal fibroblasts and hepatic stellate cells.

Hepatic stellate cells (HSCs), the liver pericytes that store retinoids, are a major source of myofibroblasts in hepatotoxic liver fibrosis (4). Liver injury results in activation of quiescent HSCs (qHSCs), which proliferate and undergo phonotypical and morphological changes characteristic of myofibroblasts. Removal of the injurious agent results in the clearance of activated HSCs (aHSCs) by the cytotoxic action of natural killer cells (1), and is linked to upregulation of ligands of NK cell receptor NKG2D, MICA and ULBP2, in senescent aHSCs (3). Although never demonstrated in vivo, studies in culture suggest that aHSCs can revert to a more quiescent phenotype (5), characterized by expression of adipogenic genes and loss of fibrogenic gene expression (5).

Portal fibroblasts normally comprise a small population of the fibroblastic cells that surround the portal vein to maintain integrity of portal tract. They were first described as "mesenchymal cells not related to sinusoids", and since then were called "periductular fibroblasts" or "portal/periportal mesenchymal cells" (64) and implicated by association in the pathogenesis of cholestatic liver injury. In response to chronic injury, portal fibroblasts may proliferate, differentiate into α-SMA-expressing myofibroblasts, and synthesize extracellular matrix (64) (65-67).

The contribution of portal fibroblasts (PFs) to liver fibrosis of different etiologies is not well understood, mainly because of difficulties in isolating PFs and myofibroblasts. The most widely used method of PF isolation from rats is based on liver perfusion with enzymatic digestion followed by size selection (68). Cell outgrowth from dissected bile segments is still used to isolate mouse PFs, and after 10-14 days in culture PFs undergo progressive myofibroblastic activation (69). The disadvantage of this technique is that it requires multiple passaging and prolong culturing (64). A more physiological method of PF culturing in a precision-cut liver slice (PCLS) is designed to maintain cell-cell and cell-matrix interactions and mimic natural microenvironment of PFs, but does not enable the study of purified PFs (70). Therefore, only a few markers of PFs are available to identify PFs in the myofibroblast population, including gremlin, Thy1, fibulin 2, IL-6, elastin, the ecto-AT-Pase nucleoside triphosphate diphosphohydrolase-2 (NTPD2), and cofilin 1. In addition, the lack of desmin, cytoglobin, α2-macroglobulin, neural proteins (glial fibrillar acidic protein (GFAP), p75, synaptophysin), and lipid droplets distinguishes PFs from HSCs (1, 56, 71-74).

SUMMARY OF THE INVENTION

The disclosure provides therapeutic methods. An embodiment of the disclosure provides a method for reducing one or more symptoms of fibrosis of parenchymal organs, such as, without limitation, liver fibrosis, renal fibrosis, skin fibrosis, and/or pulmonary fibrosis in a subject by administering to a subject a therapeutic amount of a compound or compounds that upregulate an inactivation-associated gene product, for example, Hspa1a/b gene in an activated cell, such as a hepatic stellate cells (aHSC) to produce an inactivated cell, e.g., an inactivated hepatic stellate cell (iHSC) or compounds that inhibit the activity or expression of mesothelin.

Disclosed herein is a method for reducing one or more symptoms of fibrosis in a subject by administering to the subject a therapeutic amount of one or more compounds that upregulate one or more of Hspa1a/b gene, PPARα, PPARγ, HSP70, HSP40, Hyaluronan synthase 1, GATA2, C/EBPa, BMPS, septin 4, Bambi, cathepsin S and H, neural proteins: synaptogyrin 1, synaptotagmin XIII, GFAP, transcription factors: Spi-C transcription factor (spi/PU.1 related), Spi-B transcription factor (spi-1/PU.related), PU.1-IRF, IRF-1 and 3 and 5, ISRE, Stat1, Pax5, Mafk2, ISGF3-g1; BL34 regulator of G-protein signaling 1, Rnd1-Rho family GTPase, in an activated fibrogenic myofibroblast cell or fibrogenic myofibroblast-like cell in an amount sufficient to decrease or inhibit the fibrosis.

Compounds used in the method can be selected from a PPARα agonist, PPARγ agonist, Hsp70 upregulator, HSP40 upregulator, Hspa1a/b upregulator, Hyaluronan synthase 1 upregulator or GATA2 upregulator.

In an embodiment of the method, the compound or compounds administered upregulate PPARγ, PPARα and/or Hspa1a/b.

In some embodiments of the method, PPARα agonists, and/or PPARγ agonists are used in combination with one or more Hsp70 upregulator, HSP40 upregulator, Hspa1a/b upregulator, Hyaluronan synthase 1 upregulator or GATA2 upregulator.

In some embodiments of the method the PPARα agonist is fenofibrate, WY14643, gemfibrozil, or ciprofibrate.

In some embodiments, the PPARγ agonist is thiazolidinediones, or 15-deoxy-delta (12, 14)-prostaglandin J2.

In other embodiments, the HSP70 and HSP40 upregulator is 17-allyamino-demthoxygeldanamycin.

In still other embodiments, the Hspa1a/b upregulator is taurolidine or tumor necrosis factor receptor apoptosis inducing ligand.

Disclosed herein are methods for treating fibrosis associated with the expression of mesothelin in a subject in need of treatment, comprising administering to said subject a therapeutic amount of an agent that comes into contact with a cell expressing mesothelin in an amount sufficient to treat the fibrosis. In an aspect of this embodiment, the agent is an antibody or antibody fragment that binds to mesothelin. In other aspects, the antibody or antibody fragment is a conjugate. In some aspects, the conjugate is an immunotoxin. In other aspects, the agent is a small molecule, inhibitory RNA, such as, without limitation, siRNA, or shRNA, ribozyme, peptide, or antisense that inhibits mesothelin expression and/or mesothelin function.

In some embodiments the fibrosis is fibrosis of the lung, liver, heart, kidney, skin, gastrointestinal tract or a combination thereof.

In some embodiments disclosed herein, the agent is administered to subjects with cholestatic liver fibrosis and/or biliary atresia.

Disclosed herein are methods for treating a condition associated with the expression of mesothelin in a subject, comprising obtaining a sample from a subject; determining if the sample contains cells that are Mesothelin$^+$; wherein if the sample contains cells that are Mesothelin$^+$ the subject is administered an agent that inhibits the activity of mesothelin and/or the expression of mesothelin. In some aspects of this method, the sample is analyzed for cells that also have at least one portal fibroblast marker selected from Vitamin A$^-$, Collagen$^+$, Thy1.1$^+$, and Elastin$^+$. In some aspects of this method, the sample is analyzed for Vitamin and then for cells that also have one or more of Mesothelin$^+$, Collagen$^+$, Thy1.1$^+$, and Elastin$^+$. In some aspects of this method, the determination of a portal fibroblast marker is done using flow cytometry. In some embodiments of this method, the condition treated is fibrosis, such as fibrosis of the lung, liver, heart, kidney, skin, gastrointestinal tract or a combination thereof. In other embodiments of the method, the condition treated is cholestatic liver fibrosis and/or biliary atresia. In an aspect of the method, the agent is an antibody or antibody fragment that binds to mesothelin. In other aspects, the antibody or antibody fragment is a conjugate. In some aspects, the conjugate is an immunotoxin. In other aspects the agent is a small molecule, inhibitory RNA, such as, without limitation, siRNA, or shRNA, ribozyme, peptide, or antisense that inhibits mesothelin expression and/or mesothelin function.

In still other aspects, the inhibition of mesothelin can inhibit and/or attenuate activation of Portal Fibroblasts in patients undergoing liver resection or in pediatric patients awaiting surgery to correct biliary atresia.

The methods described herein can be used to treat a fibrotic condition such as a fibrotic condition of the lung, liver, heart, kidney, skin, gastrointestinal tract or a combination thereof.

In other embodiments, the method can be used to treat a fibrotic condition of the liver chosen from fatty liver disease, steatohepatitis, primary and secondary biliary cirrhosis, cirrhosis, alcohol induced liver fibrosis, biliary duct injury, biliary fibrosis, hepatic fibrosis associated with hepatitis infection, autoimmune hepatitis, non-alcoholic fatty liver disease or progressive massive fibrosis.

In an embodiment of the method, the agents, compound or compounds induce inactivation of fibrogenic myofibroblast or fibrogenic myofibroblast-like cells. In an aspect of this embodiment, the fibrogenic myofibroblast-like cell is a hepatic stellate cell or portal fibroblast.

In another embodiment of the disclosure, the agents, compound or compounds of the method are given in combination with other antifibrotics, corticosteroids, anti-inflammatories, immunosuppressants, chemotherapeutic agents, anti-metabolites, and/or immunomodulators.

In another embodiment of the disclosure, the agent, compound or compounds of the method are given in combination with one or more of the following: adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI262570, glycyrrhizin (monoammonium glycyrrhizinate, glycine, L-cysteine monohydrochloride, interferon gamma-1b, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, or warfarin.

The invention also provides diagnostic methods. In one embodiment, the invention provides a method for detecting myofibroblasts in a sample, for example, hepatic stellate cells (HSCs) by determining the presence of at least one myofibroblast marker, for example, detecting an HSC marker selected from vitamin A$^+$, Collagen$^+$, Desmin$^+$, GFAP$^+$, CD146$^+$.

In another embodiment of the diagnostic method, the invention provides a method for detecting portal fibroblasts (PFs) in a sample by determining the presence of at least one PF marker selected from Vitamin A$^-$, Collagen$^+$, Thy1.1$^+$, and Elastin$^+$, Mesothelin$^+$.

In still another embodiment of the diagnostic method, the invention provides a method for distinguishing portal fibroblasts (PFs) and Hepatic Stellate Cells (HSCs) in a sample by determining at least one of following:
 a) the presence of at least one HSC marker selected from vitamin A+, Collagen$^+$, Desmin$^+$, GFAP$^+$, CD146$^+$, and
 b) the presence of at least one PF marker selected from Vitamin A$^-$, Collagen$^+$, Thy1.1$^+$, and Elastin$^+$, Mesothelin$^+$.

An embodiment of the diagnostic method is the utilization of flow cytometry.

The disclosure additionally provides in one embodiment a method for diagnosing liver fibrosis in a subject by determining at least one of the following
 a) determining, in a liver sample that contains fibrogenic myofibroblasts from a subject, the presence of portal fibroblasts (PFs) and Hepatic Stellate Cells (HSCs), and
 b) determining the level of at least one of said portal fibroblasts (PFs) and of said Hepatic Stellate Cells (HSCs) in a liver sample, and
 c) determining the ratio of portal fibroblasts (PFs) to Hepatic Stellate Cells (HSCs) in the liver sample.

The method for diagnosing liver fibrosis can also include the step of determining the contribution of myofibroblasts of other origins, such as CD45$^+$ Collagen$^+$ fibrocytes.

Another embodiment disclosed herein are drug screening methods that use the disclosed animal models, culture methods, identified markers and/or upregulated or downregulated gene expression of fibroblasts, such as portal fibroblasts and hepatic stellate cells for identifying agents and or compounds that can inactivate, inhibit, reduce, kill, and/or change the status of fibroblasts from an active form to an inactive form.

DESCRIPTION OF THE DRAWINGS

FIG. 2 shows genetically labeled aHSCs persist after 1 mo recovery. A. Livers from Collagen-α2(I)$^{Cre-YFP}$ mice (no injury n=4; CCl$_4$-treated n=8; recovered 1 mo n=10) were co-stained for YFP, GFAP, Desmin, α-SMA. Genetically labeled HSCs were identified after 1 mo. recovery by YFP$^+$ expression in Desmin$^+$ or GFAP$^+$ cells. The number of YFP$^+$ HSCs is calculated relative to total HSCs (100%, merge 1, p<0.05 comparing CCl$_4$ and recovery groups). Nuclei are shown (DAPI, merge 2). B. HSCs (Vitamin A$^+$) from Collagen-α2(I)$^{Cre-YFP}$ mice (no injury n=4; CCl$_4$-treated n=6; recovered 1 mo n=6) were analyzed by flow cytometry. Genetically labeled aHSC and iHSCs were identified by simultaneous Vitamin A$^+$ and YFP$^+$ expression. Dot plots are shown, p<0.01 (comparing YFP$^+$ aHSC and YFP$^+$ iHSCs). C. Genetically labeled GFP$^+$ HSCs persist in the livers of tamoxifen-inducible Col-α2(1)$^{ER-Cre-GFP}$ after 1 mo. of recovery from CCl$_4$. To avoid genetic labeling of HSCs during development, tamoxifen-inducible Col-α2(1)$^{ER-Cre-GFP}$ mice were generated by crossing Col-α2(1)$^{ER-Cre}$ mice×Rosa26$^{flox-Stop-mTRed-flox-mGFP}$ mice (here labeled as Rosa26$^{f/f-mTRed}$ mice), treated with CCl$_4$ (2 mo), and genetic pulse-labeling of aHSCs was induced by daily tamoxifen administration during the last week of CCl$_4$ treatment, following by 1 month of reversal of liver fibrosis. Genetically labeled HSCs were visualized by immunostaining for membrane-tagged GFP$^+$ (and simultaneous loss of mTRed$^-$ expression, merge 1), DAPI-stained nuclei (merge 2), are taken with ×20 objective. The number of genetically labeled GFP$^+$ HSCs is calculated as percent of Desmin$^+$ HSCs (100%, merge 3). Genetic labeling of 35±6% aHSCs was achieved in response to CCl$_4$. 14±4% of GFP$^+$ iHSCs persisted in the liver after 1 mo recovery (p<0.05, CCl$_4$ and recovery groups are compared), confirming that CCl$_4$-activated HSCs (and their progeny) remain in the liver after regression of fibrosis.

FIG. 4 shows genetically labeled HSCs obtain a new "inactivated" phenotype after 1 mo. of recovery. A. Microarray analysis: Vitamin A$^+$ HSCs were sort purified from Col-α2(I)$^{Cre-YFP}$ mice that were untreated (n=6), fibrotic (n=6), 7 days of recovery (n=3), and 1 mo of recovery (n=6). YFP$^+$ and YFP$^-$ HSCs were then subjected to the whole mouse genome microarray. Representative cell number is shown for each HSC group. B. YFP$^+$ iHSCs (1 mo recovery) downregulate mRNAs of fibrogenic genes, and upregulate PPARγ, Bambi but not other "quiescent" HSC genes (Adfp, Adipor1, GFAP). The results are relative mRNA level (average of normalized values/multiple probes/gene) obtained using Agilant microarray, *p<0.01, **p<0.001. C. Gene expression profile clustering analysis identifies similarity between the different HSC phenotypes. The correlation coefficient was used to compare the qHSCs (1.00) gene expression pattern with YFP$^+$ iHSCs (0.76), and aHSCs (0.63) expression patterns. D. Expression of signature genes was determined for YFP$^+$ iHSCs (1 mo) and YFP$^+$ HSCs (7 days recovery, 7 d), and fold induction (compared to YFP$^+$ aHSCs) is shown for each group.

FIG. 12 shows GFP⁺ HSCs persist in the liver of Col-α2 (I)$^{ER-Cre-GFP}$ after 1 mo of recovery from CCl₄. A. Livers Col-α1(I)$^{ER-Cre-GFP}$ mice were stained with anti-GFP antibody. Fluorescent micrographs, images are taken using ×10 objective. B. Livers from Col-α1(I)$^{ER-Cre-GFP}$ mice were stained for Desmin or α-SMA and analyzed by confocal microscopy using ×60 objective using pseudocolors, ns—non-specific. Genetically labeled inactivated HSCs were identified after 1 mo recovery by GFP⁺ expression in SMA⁻Desmin⁺ cells.

FIG. 16 shows HSCs (1 mo. recovery) acquire a new phenotype distinct from aHSCs and qHSCs. A. HSCs were isolated from Collagen-α1(I)-GFP/β-actin-RFP double transgenic mice, uninjured or after recovery (7 days or 1 mo) from CCl₄, and injected intrahepatically (2.2×10⁵ cells) into 1 day old Rag2$^{-/-}$γc$^{-/-}$ pups. One month later mice were gradually subjected to CCl₄ injury. Engraftment of qHSCs and HSCs 7 d and 1 mo. recovery was evaluated in each individual mice by the presence of RFP⁺GFP⁺ cells and corresponded to 50%, 78% and 80% (p<0.05), respectively. The number of activated HSCs was estimated in livers and corresponded to high (+++), intermediate (++) and low (+) and very low (±).B. HSCs were isolated from Collagen-α1 (I)$^{Cre-YFP}$ mice, uninjured or after 2 weeks recovery from CCl₄-injury, and injected intrahepatically into CCl₄-treated wild type mice (n=3/group). Mice were subjected for additional 2 weeks of CCl₄, and livers were analyzed for the presence of YFP⁺Desmin⁺ HSCs by fluorescent microscopy. YFP⁺ cells were detected in all mice, due to low engraftment the results are statistically non-significant.

FIG. 17 shows genetically labeled YFP⁺ HSCs decrease collagen-α1(I)-GFP expression after 1 mo of recovery. A. Col-α1(1)$^{Cre-YFP}$ mice were crossed with Col-GFP mice (no injury n=3; CCl₄ n=4; 1 mo recovery n=4) and livers were analyzed for YFP and GFP expression. GFP was visualized by fluorescence. YFP⁺/GFP⁺ were visualized by immunostaining with anti-GFP Ab using DAB method. The number of positive cells is calculated as percent of Desmin⁺ cells (100%, not shown). The staining is performed on the same section, images are shown using ×20 objective. B. Genetically labeled YFP⁺ HSCs decrease collagen-α1(I)-GFP expression after 1 mo of recovery. Col-α1(1)$^{Cre-YFP}$ mice were crossed with Col-GFP mice. HSCs were isolated from livers by gradient centrifugation (no injury n=3; CCl₄ n=3, 2 w recovery n=3; 1 mo recovery n=3). Vitamin A⁺ HSCs were analyzed by flow cytometry for expression of YFP and GFP. Representative histograms are shown (representative dot plots are shown in C). The results demonstrating expression of Col-GFP and YFP in HSCs are shown as mean fluorescent intensity (mfi)±SEM, p<0.01. C. Representative dot plot are shown for HSCs isolated after CCl₄ or injury or after 2 weeks recovery from fibrosis. HSCs were isolated by gradient centrifugation, live cells (P1) were analyzed for Vitamin A expression. Vitamin A+ HSCs (P2) were analyzed by flow cytometry for expression of YFP and GFP (Q1-4).

FIG. 18 shows Analysis of gene expression profile of inactivated HSCs during recovery from fibrosis. A. Heat map: Genes upregulated (yellow) and downregulated (blue) are shown for distinct HSC groups. The gene expression pattern of YFP+ HSCs (7 days recovery) was compared to YFP+ aHSCs. Specific genes upregulated or downregulated in YFP+ HSCs (7 days recovery) versus YFP+ aHSCs were grouped in four clusters. B. YFP+ HSCs after 7 days recovery were characterized by Gene Ontology biological process annotations. YFP+ iHSCs (1 mo. recovery) downregulate mRNAs of Plexin C1 and Rxra, and upregulate C/EBPa. The results are relative mRNA level (average of normalized values/multiple probes/gene) obtained using Agilant microarray, $*p<0.01$, $**p<0.001$. Spp1—secreted phosphoprotein 1, Pdgfc—platelet-derived growth factor C, Bmp 5—bone morphogenic protein 5, Rxra—retinoid X receptor α, Ppara—peroxisome proliferator activated receptor α, Ece 1—endothelin converting enzyme 1, Insig 1—insulin induced gene 1. C. Expression of PPARγ, Hsp1a/b and MHCII was detected in iHSCs (1 mo recovery) using immunocytochemistry. Cell morphology (BF) and nuclei (DAPI) are also shown. Micrographs are taken with ×40 objective. D. Pathways upregulated in YFP+ iHSCs (1 mo.) are shown according to KEGG pathway functional enrichment analysis. iHSCs are characterized by the unique expression of 423 signature genes. Upregulated genes are marked with red stars for each pathway. The following pathways were identified for YFP+ iHSCs (1 mo.): Chemokine/cytokine signaling (21 genes, $p<5.4e^{-8}$); Cell adhesion (11 genes, $p<9.6e^{-4}$); TLR signaling pathway (9 genes, $p<7.7e^{-4}$); Antigen presentation (7 genes, $p<9.5e^{-3}$). E. Pathways induced in YFP+ HSCs (7 d) are shown according to KEGG pathway functional enrichment analysis. The following pathways were identified for YFP+ HSCs (7 d): ECM receptor interaction (5 genes, $p<1.3e^{-2}$); Signaling pathways in cancer (20 genes, $p<6.0e^{-3}$). Signaling pathways involved in ECM-receptor interaction and proliferation were strongly activated, including loss of growth inhibitory effects of TGF-β, reduced apoptosis due to p53 inhibition, activation of Wnt/β-catenin signaling pathway, and induction of pro-survival heat shock proteins.

FIG. 19 shows the role of heat shock proteins Hspa1a/b in survival of HSCs during recovery from fibrosis. A. Increased expression of Hspa1a/b mRNA in YFP+ HSCs after 7 days recovery was confirmed by RT-PCR, $*p<0.01$. B. Hspa1a/b$^{-/-}$ HSCs lack expression of Hsp1a/b, as shown by immunostaining of HSCs isolated from Hsp1a/b–/– and wild type mice. Micrographs are taken with ×20 objective. C. Apoptosis was induced in Hsp1a/b$^{-/-}$ and wild type HSCs by glyotoxin (25 nM) for 4 h, or by TNF-α(20 ng/ml)+Actinomycin (0.2 μg/ml) for 18 h. Cell morphology (BF), Vitamin A and apoptotic cells (TUNEL+ staining) are shown using ×10 objective.

FIG. 20 shows mesothelin is a new marker of activated portal fibroblasts. A. Using the Whole genome mouse microarray, the gene expression profile of activated portal fibroblasts was assessed and compared to CCl$_4$- and BDL-activated HSCs. Expression of mRNA of genes uniquely upregulated in aPFs is listed as "Signature genes". Expression of PF-specific genes previously identified is shown in red. The new genes identified in our study is shown in green. The data is mRNA (fold induction), $p<0.0001$. B. Expression of aPF-specific new genes was confirmed by RT-PCR and compared to other liver specific cells: Kupffer cells (KC), Endothelial cells (EC), BDL-activated PFs, BDL and CCl4-activated HSCs. Expression of mesothelin, asporin, basonuclin, calcitonin-a, uroplakin-1b mRNA was specifically induced only in activated PFs. C. Mesothelin is a marker of activated PFs. Liver tissue from non-injured, BDL- and CCl$_4$-injured wild type mice was stained with anti-Mesothelin Ab (Abcam). Upregulation of specific staining was detected in BDL-injured mice (versus CCl$_4$-injured mice). D. Human liver tissues were obtained from patients with hepatitis C, diagnosed with clinical and pathological stages of liver fibrosis (F1) and cirrhosis (F4), or no fibrosis (F0), and analyzed by immunohistochemistry for expression of human mesothelin and Sirius Red staining. Representative images are shown using ×10 objectives. Expression of mesothelin was associated with fibrotic lesions.

DESCRIPTION OF THE INVENTION

Figure 1:
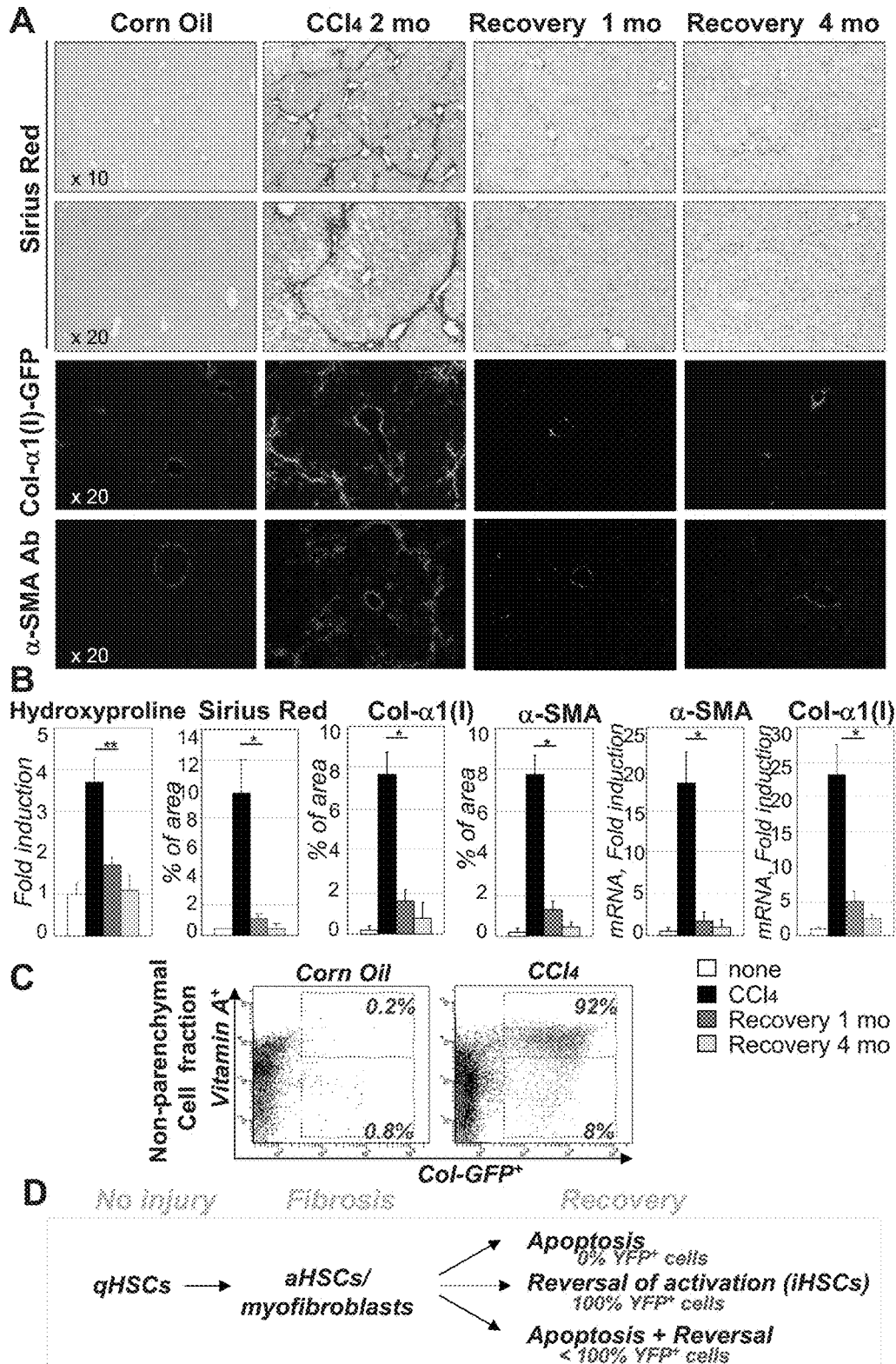
FIG. 1 shows regression of liver fibrosis is accompanied by loss of myofibroblasts. A. A comparison of the livers of Col-GFP mice that were untreated, CCl$_4$-treated (2 mo.), or recovered from CCl$_4$ (1 mo and 4 mo) with respect to GFP expression, Sirius Red staining and α-SMA immunohistochemistry. Representative bright field and fluorescent micrographs are shown using ×10 and ×20 objectives. B. Quantification of same four groups in (A) with respect to hydroxyproline content, Sirius Red staining, α-SMA immunofluorescence, GFP expression, collagen-α1(I) mRNA level, and α-SMA mRNA level, *p<0.01, **p<0.05. C. HSCs (Vitamin A$^+$) constitute >90% of myofibroblasts (Vitamin A$^+$GFP$^+$), as detected by flow cytometry of the non-parenchymal cell fraction from CCl$_4$-treated (2 mo) Col-GFP mice (n=3). D. CCl$_4$ induces activation of qHSCs into aHSCs/myofibroblasts. Cre-loxP based genetic labeling marks the fate of collagen Type I-expressing aHSCs/myofibroblasts (see FIG. 6). During recovery from CCl$_4$-liver fibrosis, aHSCs may 1) apoptose (no genetically labeled YFP$^+$ HSCs will remain in the liver), 2) inactivate (all YFP$^+$ cells survive) or 3) some apoptose and some inactivate (YFP$^+$ iHSCs will number <100% of aHSCs).

The present disclosure relates to methods for diagnosing and treating a fibrotic condition in a subject. The subject can be any animal that exhibits fibrotic processes, preferably a mammalian subject. Mammalian subjects include, without limitation, humans, non-human primates, dogs, cats, and horses and mice.

As used herein, the term "subject" refers to an animal, typically a human (i.e., a male or female of any age group, e.g., a pediatric patient (e.g., infant, child, adolescent) or adult patient (e.g., young adult, middle-aged adult or senior adult) or other mammal, such as a primate (e.g., cynomolgus monkey, rhesus monkey); other mammals such as rodents (mice, rats), cattle, pigs, horses, sheep, goats, cats, dogs; and/or birds, that will be or has been the object of treatment, observation, and/or experiment. When the term is used in conjunction with administration of an, agent, compound or drug, then the patient has been the object of treatment, observation, and/or administration of the compound or drug.

"Treating," "treat," and "treatment" as used herein, refers to partially or completely inhibiting or reducing the fibrotic condition which the subject is suffering. In one embodiment, this term refers to an action that occurs while a patient is suffering from, or is diagnosed with, the fibrotic condition, which reduces the severity of the condition, or retards or slows the progression of the condition. Treatment need not result in a complete cure of the condition; partial inhibition or reduction of the fibrotic condition is encompassed by this term.

As used herein, "fibrotic condition" refers to a disease or condition involving the formation and/or deposition of fibrous tissue (or scar), e.g., excessive connective tissue builds up in a tissue and/or spreads over or replaces normal organ tissue (reviewed in, e.g., Wynn, Nature Reviews 4:583-594 (2004) and Abdel-Wahab, O. et al. (2009) Annu. Rev. Med. 60:233-45, incorporated herein by reference). In certain embodiments, the fibrotic condition involves excessive collagen mRNA production and deposition, (mostly collagen Type I). In certain embodiments, the fibrotic condition is caused, at least in part, by injury, e.g., chronic injury (e.g., an insult, a wound, a toxin, a disease). In certain embodiments, the fibrotic condition is associated with an inflammatory, an autoimmune or a connective tissue disorder. However, inflammation, damage to the blood vessels, does result in fibrosis. Activation of fibrogenic myofibroblasts is the main cause of fibrosis. For example, myofibroblasts are absent in normal tissue of non-parenchymal organs. In turn, chronic inflammation in a tissue can lead to activation of fibrogenic myofibroblasts (from different sources) in that tissue. Exemplary fibrotic tissues include, without limitation, liver tissue, lung tissue, heart tissue, kidney tissue, skin tissue, gut tissue, peritoneal tissue, bone marrow, and the like.

The term "or" is used herein to mean, and is used interchangeably with, the term "and/or", unless context clearly indicates otherwise.

Exemplary fibrotic conditions that can be treated or prevented using the methods of the invention include, without limitation, a fibrotic condition of the lung, liver, heart, vasculature, kidney, skin, gastrointestinal tract, bone marrow, or a combination thereof.

Exemplary fibrotic conditions that can be diagnosed according to the methods of the present invention include, without limitation, any parenchymal fibroses, including acute and chronic forms of pulmonary fibrosis, interstitial lung disease, human fibrotic lung disease, liver fibrosis, cardiac fibrosis, kidney fibrosis.

In certain embodiments, the fibrosis of the liver or hepatic fibrosis is chosen from one or more of: fatty liver disease, steatohepatitis (e.g., nonalcoholic steatohepatitis (NASH), cholestatic liver disease, primary biliary cirrhosis (PBC), biliary fibrosis, cirrhosis, alcohol induced liver fibrosis, biliary duct injury, infection or viral induced liver fibrosis, congenital hepatic fibrosis, autoimmune hepatitis, or cholangiopathies (e.g., chronic cholangiopathies).

In certain embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins such as arsenic), alpha-1 antitrypsin deficiency, hemochromatosis, Wilson's disease, galactosemia, or glycogen storage disease. In certain embodiments, the hepatic fibrosis is associated with an inflammatory disorder of the liver.

It has been previously shown that myofibroblasts, such as hepatic stellate cells (HSCs) senescence and apoptose during recovery from fibrosis. Until now, apoptosis of HSCs has not been quantified; and, therefore, it was not known that some HSCs survive and revert their phenotype. In an embodiment disclosed herein, Applicants have discovered that induction of HSCs inactivation represents a new strategy for antifibrotic therapy.

As used herein "myofibroblasts" are characterized immunophenotypically by a spindle or stellate shape, pale eosinophilic cytoplasm, expression of abundant pericellular matrix and fibrotic genes (vimentin, α-smooth muscle actin (α-SMA), non-muscle myosin, fibronectin) (33). Ultrastructurally, myofibroblasts are defined by prominent rough endoplasmic reticulum (rER), a Golgi apparatus producing collagen, peripheral myofilaments, fibronexus (no lamina) and gap junctions (33). Myofibroblasts are implicated in wound healing and fibroproliferative disorders (34-36). Studies of fibrogenesis conducted in different organs strongly suggest that resident myofibroblasts are the primary source of ECM (37). Several sources of myofibroblasts have been identified: liver resident cells (hepatic stellate cells (HSCs), and portal fibroblasts (PFs)); cells originated by mesenchymal transition (EMT or EndMT) and BM-derived cells (fibrocytes and mesenchymal stem cells) (1, 37, 46-47). In experimental liver fibrosis, activated hepatic stellate cells (aHSCs) and activated portal fibroblasts (aPFs) comprise >80% of the collagen producing cells 1, suggesting that aHSCs and aPFs are the major source of myofibroblasts. In response to fibrogenic stimuli, such as TGF-β1, myofibroblasts in all tissues express α-SMA, secrete ECM (fibronectin, collagen type I and III), obtain high contractility and change phenotype (production of the stress fibers) (38). Classical myofibroblasts differentiate from a mesenchymal lineage and, therefore, lack expression of lymphoid markers such as CD45 or CD34. Sustained injury may trigger (trans) differentiation of myofibroblasts from other cellular sources, including HSCs 1.

HSCs are perisinusoidal cells that normally reside in the Disse space and contain numerous retinoid and lipid droplets (39, 40). Under physiological conditions, HSCs exhibit a quiescent phenotype and express neural markers, such as GFAP, synamin, synaptophysin 1, and nerve growth factor receptor p75 (41, 42), secrete HGF, and store vitamin A (43). HSCs are also implicated in phagocytosis and antigen presentation (44, 45). In response to injury, quiescent HSCs lose vitamin A, acquire contractility and activate into collagen type I- and SMA-expressing myofibroblasts. Although the mechanism of HSC activation has been comprehensively studied, insights into the origin of HSCs are new (46, 47). It has been proposed that HSCs are liver resident cells and may originate from a common hepatic precursor cell (48, 49). However, similar expression of neural markers suggests that HSCs and astrocytes arise from a common progenitor during embryonic development (37, 1).

As used herein, the articles "a" and "an" refer to one or to more than one (e.g., to at least one) of the grammatical object of the article.

Disclosed herein is a diagnostic method to distinguish between different types of liver fibroses using flow cytometry to analyze and purify different subsets of fibrogenic myofibroblasts, such as resident hepatic stellate cells and portal fibroblasts (PFs) associated with a specific liver fibroses. For example, activated hepatic stellate cells were found to be the primary fibrogenic myofibroblast in $CCl_4$ induced liver fibrosis; whereas, activated portal fibroblasts were found to be the predominate fibrogenic myofibroblast in cholestatic liver injury. Thus, in another embodiment, Applicants have discovered that the identification of specific subsets of fibrogenic myofibroblasts in response to different kinds of fibrogenic injury allows one to study the composition of collagen producing cells for each type of fibrogenic injury and provides a definitive target for antifibrotic therapy as well as other studies such as drug screening etc.

Portal fibroblasts are spindle-shaped cells that are present in most types of tissues, particularly connective tissues. These cells are of mesenchymal origin and express elastin, and vimentin, but not desmin or α-SMA. Fibroblasts participate in the turnover of ECM under normal conditions (38, 50-52). Fibroblasts and myofibroblasts derived from portal myofibroblasts are distinct from HSCs in that they express Thy-1 (a glycophosphatidylinositol-linked glycoprotein of the outer membrane leaflet described in myofibroblasts of several organs (53, 54)), do not store retinoids, and do not express neural markers. Induced mostly by cholestatic liver injury, portal fibroblasts proliferate (though much slower than HSCs (55)) and deposit collagen (e.g. type I) around biliary tracts (56). In response to bile duct ligation (BDL) model of cholestatic injury in mice, PFs proliferate, differentiate into α-SMA-expressing myofibroblasts, and synthesize extracellular matrix.

Activated Portal Fibroblasts (aPFs) play a pivotal role in the pathogenesis of cholestatic liver fibrosis (64, 66), and, therefore, based on the data disclosed herein, aPFs are indicated as primary targets for anti-fibrotic therapy in patients with cholestatic liver injury. Under physiological conditions, PFs comprise a small population of cells that surround the portal vein to maintain integrity of the portal tract (64). Only a few markers are available to identify PFs in the myofibroblast population, including gremlin, Thy1 (56), fibulin 2 (56), IL-6, elastin (72), the ecto-AT-Pase nucleoside triphosphate diphosphohydrolase-2 (NTPD2) (73), and cofflin 1 (74). In addition, the lack of desmin, cytoglobin, α2-macroglobulin (56), neural proteins (glial fibrillar acidic protein (GFAP), p'75, synaptophysin, $p75^{NGFr}$)) and lipid droplets distinguish PFs from HSCs (1, 64, 75). Identification of additional PF markers will advance our understanding of the pathogenesis of liver fibrosis. Disclosed herein are newly identified aPF-specific markers, including mesothelin.

Mesothelin, a glycosylphosphatidylinositol-linked glycoprotein, is upregulated in malignant mesotheliomas (76) and mediates intracellular adhesion and metastatic spread (77). In adult mice, mesothelin is expressed only in the mesothelial lining of parenchymal organs (78, 79). $Msln^{-/-}$ mice have been generated, and exhibit no obvious abnormalities. Lineage tracing studies at early embryogenesis have linked expression of mesothelin to precursors of fibroblasts and smooth muscle cells (FSMCs) (79). In contrast to embryonic mesothelium (79), adult mesothelin-expressing cells reside solely in the mesothelial layer lining parenchymal organs and serose cavities (78) in a dormant state, and do not proliferate until injury or stress (79). However, recent studies suggested that in response to injury, aPFs originate from hepatic mesothelium (19, 80, 81).

Mesothelin is also highly expressed in several species of malignant tumors, such as mesothelioma as well as ovarian and pancreatic cancers. Previous studies have implicated mesothelin in mediation of cellular interaction and metastatic dissemination. Due to strong induction in different types of cancer, mesothelin is considered as a tumor-associated antigen, which serves as a prognostic marker of disease progression, and became a therapeutic target for anti-cancer therapy.

Here it is demonstrated that expression of mesothelin is highly upregulated in aPFs in response to bile duct ligation (BDL), and mesothelin exhibit an expression pattern compared to Thy1 and Elastin staining. The data disclosed herein suggest that mesothelin is a unique marker of activated PFs. Because aPFs play a critical role of development of cholestatic liver fibrosis, these data demonstrate that mesothelin is a target for anti-fibrotic therapy. Consistently, mesothelin knockout (ko) mice grow and develop normally and exhibit no visible abnormalities. However, in response to cholestatic liver injury, such as BDL, mesothelin ko mice develop less fibrosis than the wild-type (wt) littermates. Meanwhile, Mesothelin ko mice and wt littermates develop similar levels of fibrosis in response to toxic liver injury (carbon tetrachloride, $CCl_4$), which predominantly activates Hepatic Stellate Cells (>89%, FIG. 23A).

Mesothelin as a Target for Anti-Fibrotic Therapy.

Figure 24:
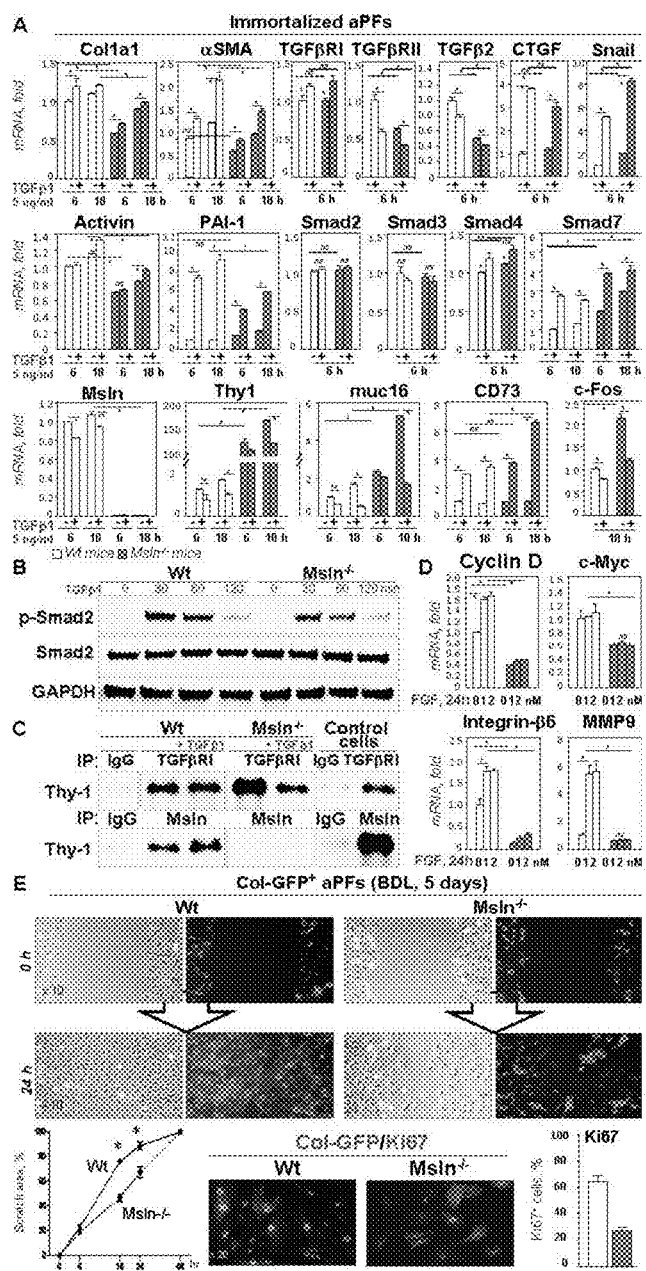
FIG. 24 Characterization of Msln function in aPFs. A. Immortalized wt and Msln$^{-/-}$ aPFs were serum starved (24 h), stimulated with TGF-β1 (5 ng/ml; 6 and 18 h), and analyzed by qPCR, *p<0.01, **p<0.05. B. Western blot of TGF-β1-stimulated immortalized wt and Msln$^{-/-}$ aPFs probed with anti-phospho-Smad2, -Smad2, GAPDH Abs. C. Immunoprecipitation (IP) with anti-TGFβRI Ab (but not with non-specific IgG) pulled down Thy-1 from lysate of wt and Msln$^{-/-}$ aPFs and RFL-6 CD90.2 cell line (overexpressing Thy-1, labeled as control cells, upper panel). IP with anti-Msln Ab (MBL, but not with IgG) pulled down Thy-1 from lysated of wt (but not Msln$^{-/-}$) aPFs and LMP cell line (shown to express Msln, control cells, lower panel). Western blot, n=3. D. Immortalized wt and Msln$^{-/-}$ aPFs were stimulated with FGF (1 and 2 nM, 24 h) and analyzed by qPCR. E. Scratch assay. Primary aPFs were isolated from wt or Msln$^{-/-}$ mice after BDL (5 d). Msln$^{-/-}$ PFs exhibited a defect in migration activity (*p<0.05), which correlated with reduced proliferation of Msln$^{-/-}$ PFs in the scratch area, as shown by Ki-67 staining (*p<0.05).

The functions of Mesothelin (Msln)-deficient and wild type aPFs were compared. It was found that $Msln^{-/-}$ aPFs exhibit a defect in proliferation, migration and mounting fibrogenic responses to TGF-β1 (FIG. 24). Therefore, these data indicate that inhibition of mesothelin expression will strongly attenuate development of liver fibrosis caused by cholestatic liver injury. Targeting of mesothelin by, without limitation, anti-mesothelin Abs and antibody fragments, immunotoxins targeted to mesothelin, such as by attachment to antibodies, antagonists of mesothelin (small molecules), siRNA, shRNA, peptides, antisense, ribozymes etc. can be used to inhibit or attenuate development of liver fibrosis and treat patients awaiting liver surgery or transplantation. For example, this has a particular significance for pediatric patients who are born with biliary atresia but cannot be immediately operated on. Administration of Mesothelin-blocking agents (for example, without limitation, antibodies, antibody fragments, immunotoxins targeted to mesothelin, small molecules, etc.) can attenuate development of cholestatic liver fibrosis and liver damage while these patients are awaiting surgery. Further, administration of Mesothelin-blocking agents (antibodies, small molecules, etc.) can become an alternative (or supplemental) treatment to already existing treatment strategies.

Due to expression on many types of cancer and mesotheliomas, Mesothelin has been considered as a target for anti-cancer therapy. Thus all tools developed for cancer's associated with expression of mesothelin are applicable to the embodiments described herein such as, without limitation, therapy with anti-mesothelin Abs, immunotoxins attached to antibodies that target mesothelin, antagonists of mesothelin (small molecules). These therapies can be used to inhibit activation of Portal Fibroblasts and attenuate development of cholestasis-induced liver fibrosis.

Antibodies and antibody fragments, including antigen binding fragments and humanized antibodies, useful for the methods disclosed herein are described in U.S. Pat. Nos. 8,206,710, 8,460,660, 8,425,904, 6,153,430, and PCT Publication No. WO/1997/025068. Anti-mesothelin antibodies and conjugates are described in U.S. Pat. No. 8,435,494, PCT Publication Nos. WO2010/053559, WO2012/154530, WO2012/087962 and EP2655418. Antibodies and antibody fragments, including antigen binding fragments and humanized antibodies, useful for the methods disclosed herein comprise antibodies comprising: CDRs 1, 2, and 3 of the $V_H$ chain (i.e., SEQ ID NOS:1, 2 and 3, respectively) and CDRs 1, 2, and 3 of the $V_L$ chain (i.e., SEQ ID NOS:4, 5 and 6, respectively); or, CDRs 1, 2, and 3 of the $V_H$ chain (i.e., SEQ ID NOS:15, 16, 17, respectively) and CDRs 1, 2 and 3 of the $V_L$ chain (i.e., SEQ ID NOS:18, 19 and 20, respectively). In alternative embodiments, the $V_H$ chain and the $V_L$ chain are linked by a peptide linker to form a scFv, or the $V_H$ chain and the $V_L$ chain have one or more cysteine residues engineered into a framework region to permit formation of a disulfide bond linking the $V_H$ chain and the $V_L$ chain together. Peptides useful for blocking mesothelin are described in U.S. Pat. No. 8,623,828. Antisense directed to mesothelin are described in PCT Publication No. WO/1997/025068. The use of inhibitory RNA are described in U.S. Publication No 2013/0259926, Wang et al. Plos One (2012) 7(4): e33214, and Melaiu et al., (2014) Plos One 9(1): e85935. Examples of small molecule inhibitors of mesothelin are described in Bharadwaj et al. (2011) J. of Surgical Research, 165(2):303. All of these papers, patents and patent applications are incorporated herein by reference.

Another embodiment described herein is the detection of mesothelin in patients suspected of and/or having cholestatic liver disease for use as a prognostic marker of the severity of liver fibrosis and activation of Portal Fibroblasts.

As described herein, gene expression microarray was used to identify unique markers of portal fibroblasts. These markers include: Calcitonin α (Calca), Glycoprotein m6a (Gpm6a), Uroplakin 1β, Basonuclin 1 (Bnc1), Mesothelin (msln), Frizzled-related protein 4 (Sfrp4), Proteoglycan 4 (Prg4), Asporin (aspn), Mycin 16 (Myc16), IL-18R1, Myosin light peptide7 (Myl7), Vitrin (Vit), Glipican 3 (Gpc3), CD200, Apolipoprotein D (ApoD), IL-25R, Dermokin (Dmkn), Vanin (Vnn1), Thrombospondin 4 (Thbs4), Integrin β4 (Itgb4), CD55. These markers are upregulated in activated Portal Fibroblasts but not in activated Hepatic Stellate cells (or other hepatic cells) or other cells in the liver (FIG. 20).

Data disclosed herein indicates that mesothelin is an important molecule that regulates activation of Portal Fibroblasts, and that mesothelin is a reliable marker to detect activated Portal Fibroblasts, which can be used for diagnostics of cholestatic liver fibrosis. Mesothelin is not only a marker of Portal Fibroblasts, but also a molecule that plays a critical role in activation of Portal Fibroblasts and development of cholestatic liver fibrosis. Studies disclosed herein indicate that mesothelin-deficient Portal Fibroblasts and mesothelin knockout mice demonstrated that mesothelin-deficient Portal Fibroblasts have a defect in activation, collagen production, response to TGF-β1, proliferation, and migration. Although mesothelin knockout mice grow and develop normally and have no visible abnormalities, they exhibited a dramatic difference in development of liver fibrosis compared with the wild type mice in response to cholestatic liver injury. The data disclosed herein suggest that mesothelin plays a critical role in injury and stress, but is dispensable during embryonic development and adulthood under homeostatic conditions.

Deletion of mesothelin in mice results in attenuation of cholestatic liver fibrosis, but not carbon-tetrachloride ($CCl_4$)-induced toxic liver fibrosis. The data suggest that mesothelin is critical for cholestatic liver fibrosis which requires activation of Portal Fibroblasts. This high specificity to liver fibrosis of cholestasis-induced liver injury, makes mesothelin an attractive target for anti-fibrotic therapy.

An embodiment disclosed herein is to target mesothelin (and Mesothelin myofibroblasts) to inhibit activation of fibrogenic myofibroblasts in cholestatic liver fibrosis in patients/subjects in need of such treatment. Another embodiment disclosed herein is the treatment of pediatric patients with biliary atresia with an agent that inhibits the activity or expression of mesothelin or uses mesothelin to target an immunotoxin to a mesothelin expressing myofibroblast. Administration of mesothelin-blocking agents will target only activated Portal Fibroblasts since mesothelin has very limited expression in adult mouse or human body (mesothelin expression was detected in serose lining of parenchymal organs and peritoneum), and is upregulated in response to chelestatic liver injury. Consistent with this, mesothelin knockout mice have no visible abnormalities, suggesting that mesothelin regulates activation, proliferation, migration of fibrogenic Portal Fibroblasts in adult mice in response to injury or stress (but seems to play no role under physiological conditions during development or adulthood). We also propose that similar mechanisms are critical for fibrogenesis of other parenchymal organs, such as, without limitation, heart, and skin.

In still another embodiment, Applicants disclose the use of agents, compounds, or drugs, such as small molecules, nucleic acids, proteins or antibodies to target subsets of myofibroblasts associated with different types of fibroses. For example, activated HSCs may be targeted by agents or compounds that upregulate Hspa 1a/b and other signature genes described herein.

As used herein, the terms "drug," "agent," "compound," and "therapeutic agent" are used interchangeably, and may include, without limitation, small molecule compounds, biologics (e.g., antibodies, proteins, protein fragments, fusion proteins, glycoproteins, etc.), nucleic acid agents (e.g., antisense, RNAi/siRNA, and microRNA molecules, etc.), vaccines, etc., which may be used for therapeutic and/or preventive treatment of a disease (e.g., liver fibrosis).

Compounds useful for treating fibrosis by inducing inactivation of a specific subset of fibrogenic myofibroblasts include PPARα agonists, such as fenofibrate, WY14643, gemfibrozil, and Ciprofibrate; PPARγ agonists, such as thizolidinediones, 15-deoxy-delta (12,14)-prostaglandin J2; compounds that induce HSP70, for example, 17-allyamino-demethoxygeldanamycin; compounds that induce Hyaluronan synthase 1 induction, for example, adiponectin; compounds that induce GATA2 activation, and compounds that induce Hspa1a/b. e.g., taurolidine, tumor necrosis factor receptor apoptosis inducing ligand (TRAIL), anti-mesothelin antibodies and antibody fragments, immunotoxins targeted to mesothelin, inhibitory RNA, ribozymes, peptides that block mesothelin, small molecules that inhibit the activity of mesothelin and antisense molecules that inhibit mesothelin expression or activity.

Other genes that can be targeted for antifibrotic therapy to induce inactivation of hepatic stellate cells include compounds or agents that downregulate Ssp1 and/or Pdgfc; agents or compounds that upregulate C/EBPa, BMPS, septin 4, Bambi, Hsp40, Cathepsin S and H, neural proteins: synaptogyrin 1, synaptotagmin XIII, GFAP, transcription factors:Spi-C transcription factor (spi/PU.1 related), Spi-B transcription factor (spi-1/PU.related), PU.1-IRF, IRF-1 and 3 and 5, ISRE, Stat1, Pax5, Mafk2, ISGF3-g1, BL34 regulator of G-protein signaling 1, Rnd1-Rho family GTPase 1;

The term "upregulate" as used herein means that agent, compound or drug causes increased protein/peptide product in the target cell.

Using genetic labeling of activated HSCs (aHSCs)/myofibroblasts, Applicants demonstrate herein that some aHSCs escape cell death and revert to an inactivated phenotype (inactivated hepatic stellate cells (iHSCs)) that is similar to, but distinct from the original quiescent HSCs, including their ability to more rapidly reactivate into myofibroblasts. Thus, this newly-identified cell sub-population called is thought to be responsible for recurrent liver fibrosis. This approach for identifying iHSCs and understanding their phenotypic makeup is applicable to study fibrosis of other organs and provides an approach to identify new targets for antifibrotic therapy.

An embodiment of the invention is to induce inactivation of activated HSCs (aHSCs) to iHSCs and mitigate liver fibrosis, or prevent its recurrence.

Previously it had been thought that reversal of fibrosis is accompanied by senescence and/or apoptosis of the myofibroblasts, including aHSCs, which are responsible for the fibrosis. However, it was unknown if aHSCs myofibroblasts can escape cell death and revert to an inactive phenotype during regression of fibrosis. In an embodiment of the disclosure, Applicants disclose methods to track the cells in animals (e.g., mice and humans) involved in the diseased state.

By using a transgenic mouse system, Applicants demonstrate that different myofibroblast activation pathways are responsible for different types of liver fibrosis. For example, a majority of liver fibrosis involve mostly HSCs.

Other types of liver fibrosis, such as those that occur by blocking the common bile duct, involve both portal fibroblasts (PFs) and HSCs, however PFs play a more important role at the onset of the disease. An embodiment disclosed herein is a method to determine the most effective antifibrotic thereby by determining whether the type of liver fibrosis is caused principally by HSCs or by PFs.

Disclosed herein are specific markers that are useful for cell sorting. Myofibroblasts are aSMA$^+$ Collagen Type I$^+$ cells that are absent from the normal uninjured liver, rapidly emerge in fibrotic liver to produce the fibrous scar, and completely disappear with regression of liver fibrosis (1, 2). In hepatotoxic-induced liver fibrosis (such as CCl$_4$ or intragastric alcohol feeding), quiescent hepatic stellate cells (GFAP$^+$Desmin$^+$SMA$^-$Col$^-$ qHSCs) undergo activation to become the major source of myofibroblasts (GFAP$^+$ Desmin$^+$aSMA$^+$Col$^+$ aHSCs). Disclosed herein are the use of genetic markers to address the fate of these aHSCs/myofibroblasts during regression of liver fibrosis.

Applicants show herein that survival of iHSCs requires the upregulation of pro-survival signals, such as induction of heat shock proteins (22). Two members of Hsp70 family of heat shock proteins, Hspa1a and Hspa1b (22), that play a protective role against stress-induced apoptosis (23), were strongly and transiently upregulated in HSCs after 7 days of reversal of fibrosis (when apoptosis of other aHSCs is highest) compared with the aHSCs in fibrotic liver. An embodiment disclosed herein is treating fibrosis with agents that upregulate Hspa1a/b and other heat shock proteins which are critical for transition of activated fibrogenic myofibroblasts to inactive myofibroblasts.

Pharmaceutical Compositions, Dosage and Administration

In some embodiments, the above-described methods comprise providing agents or compounds that upregulate, for example PPARα, PPARγ, Hspa1a/b or downregulate gene products, for example, Ssp1, and Pdgfc found by Applicants to be important for inducing inactivation of fibrotic cells in vivo.

In some embodiments, the above-described methods comprise providing the agents or compounds in a pharmaceutical composition.

Pharmaceutical compositions can be formulated for administration in solid or liquid form, including those adapted for the following: oral administration, for example, drenches (e.g., aqueous or non-aqueous solutions or suspensions), tablets (e.g., those targeted for buccal, sublingual, and systemic absorption), capsules, boluses, powders, granules, pastes for application to the tongue; parenteral administration, for example, by subcutaneous, intramuscular, intravenous or epidural injection such as, for example, a sterile solution or suspension, or sustained-release formulation; topical application, for example, as a cream, ointment, or a controlled-release patch or spray applied to the skin; intravaginally or intrarectally, for example, as a pessary, cream or foam; sublingually; ocularly; transdermally; pulmonarily; or nasally.

Pharmaceutically acceptable excipients include any and all fillers, binders, surfactants, disintegrants, sugars, polymers, antioxidants, solubilizing or suspending agents, chelating agents, preservatives, buffering agents and/or lubricating agents, or combinations thereof, as suited to the particular dosage form desired and according to the judgment of the formulator. Remington's Pharmaceutical Sciences, Sixteenth Edition, E. W. Martin (Mack Publishing Co., Easton, Pa., 1980) discloses various pharmaceutically acceptable excipients used in preparing compositions and known techniques for the preparation thereof. Except insofar as any conventional carrier medium is incompatible with the compounds disclosed herein, such as by producing any undesirable biological effect or otherwise interacting in a deleterious manner with any component of the composition, its use is contemplated to be within the scope of this invention. In general, the compositions are prepared by uniformly and intimately bringing into association the compounds or agents described above with one or more excipients and then, if necessary, shaping the product.

When the agent or compound is administered to humans or animals it can be given per se or as a pharmaceutical composition containing, for example, about 0.1 to 99%, or about 10 to 50%, or about 10 to 40%, or about 10 to 30%, or about 10 to 20%, or about 10 to 15% of the agent or compound in combination with a pharmaceutically acceptable excipient.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

Actual dosage levels of the agent or compound in the pharmaceutical compositions can be varied so as to obtain an amount of the active ingredient which is effective to achieve the desired therapeutic response for a particular subject, composition, and mode of administration, without being toxic to the subject.

The selected dosage level will depend upon a variety of factors including, for example, the activity of the particular agent or compound employed, the route of administration, the time of administration, the rate of excretion or metabolism, the rate and extent of absorption, the duration of the treatment, other drugs, compounds or materials used in combination with the agent or compound, the age, sex, weight, condition, general health and prior medical history of the subject, and other similar factors well known in the medical arts.

In general, a suitable daily dose of a compound or agent will be that amount which is the lowest dose effective to produce a therapeutic effect. Such an effective dose will generally depend upon the factors described above. Generally, oral, intravenous and subcutaneous doses of the agent or compound for a subject, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to about 500 mg per day, or about 0.1 mg to about 500 mg per day.

"Therapeutically effective amount," or "therapeutic effect," as used herein, refers to a minimal amount or concentration of an agent, compound and/or drug that, when administered alone or in combination, is sufficient to provide a therapeutic benefit in the treatment of the condition, or to delay or minimize one or more symptoms associated with the condition. The term "therapeutically effective amount" can encompass an amount that improves overall therapy, reduces or avoids symptoms or causes of the condition, or enhances the therapeutic efficacy of another therapeutic agent. The therapeutic amount need not result in a complete cure of the condition; partial inhibition or reduction of the fibrotic condition is encompassed by this term.

In some embodiments, the agent or compound prevents the condition or can be used at prophylactically effective amount.

As used herein, unless otherwise specified, the terms "prevent," "preventing" and "prevention" refers to an action that occurs before the subject begins to suffer from the condition, or relapse of such condition. The prevention need not result in a complete prevention of the condition. Partial prevention or reduction of the fibrotic condition is encompassed by this term.

As used herein, unless otherwise specified, a "prophylactically effective amount" of an agent, compound and/or drug, when administered alone or in combination, prevent the condition, or one or more symptoms associated with the condition, or prevent its recurrence. The term "prophylactically effective amount" can encompass an amount that improves overall prophylaxis or enhances the prophylactic efficacy of another prophylactic agent. The prophylactic amount need not result in a complete prevention of the condition; partial prevention or reduction of the fibrotic condition is encompassed by this term.

The subject receiving the treatment can be any animal in need, including primates (e.g. humans), equines, cattle, swine, sheep, poultry, dogs, cats, mice and rats.

The agent or compound can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The agent or compound can be administered orally, intravenously, intraperitoneally, topically, transdermally, intramuscularly, subcutaneously, intranasally, sublingually, or by any other route.

Combination Therapies

The agents or compounds described above can be administered in combination with one or more therapeutic agents. Exemplary therapeutic agents include, but are not limited to, antifibrotics, corticosteroids, anti-inflammatories, immunosuppressants, chemotherapeutic agents, anti-metabolites, and immunomodulators.

By "in combination with," it is not intended to imply that the therapeutic agent and agent or compound must be administered at the same time and/or formulated for delivery together, although these methods of delivery are within the scope of the invention. The agent or compound can be administered concurrently with, prior to, or subsequent to, one or more other additional agents. In general, each therapeutic agent will be administered at a dose and/or on a time schedule determined for that particular agent. In will further be appreciated that the therapeutic agent utilized in this combination can be administered together in a single composition or administered separately in different compositions. The particular combination to employ in a regimen will take into account compatibility of the antifibrotic agent or compound with the agent and/or the desired therapeutic effect to be achieved.

In general, it is expected that additional therapeutic agents employed in combination be utilized at levels that do not exceed the levels at which they are utilized individually. In some embodiments, the levels utilized in combination will be lower than those utilized individually. The determination of the mode of administration and the correct dosage for each agent or combination therapy is well within the knowledge of the skilled clinician.

In embodiments where two agents are administered, the two agents can be administered concurrently (i.e., essentially at the same time, or within the same treatment) or sequentially (i.e., one immediately following the other, or alternatively, with a gap in between administration of the two). In some embodiments, the antifibrotic agent or compound is administered sequentially (i.e., after the first therapeutic).

Suitable therapeutics for use in combination with the compounds for inducing inactivation of fibrogenic myofibroblasts for treatment of liver fibrosis includes, without limitation, adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI262570, glycyrrhizin (monoammonium glycyrrhizinate, glycine, L-cysteine monohydrochloride, interferon gamma-1b, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, and combinations thereof. Included in the embodiments disclosed herein is the concept that the embodiments and aspects of the embodiments may be described with transition phrases such as "comprising", "consisting", "consisting essentially of" and equivalents of such terms such as, without limitation, "having" and the like.

The invention now being generally described, it will be more readily understood by reference to the following examples, which are included merely for purposes of illustration of certain aspects and embodiments of the present invention, and are not intended to limit the invention.

EXAMPLES

Methods
Mice:
Expression of collagen Type I in real time was studied using reporter Col-GFP mice (25). Cell fate mapping of aHSCs was studied using collagen-α2(I)$^{Cre}$ (26) and collagen-α1(I)$^{Cre}$ and tamoxifen-inducible collagen-α2(I)$^{ER-Cre}$ crossed to Rosa26$^{flox-Stop-flox-YFP}$ mice (or Rosa26$^{flox-mTRed-Stop-flox-mGFP}$ mice, Jackson Labs). GFAP$^{Cre}$ mice are used to determine the total number of HSCs.

Liver Fibrosis:
Liver fibrosis was induced in mice by intragastric gavage with carbon tetrachloride, CCl$_4$ (at 16×1:4 dilution in 100 µl of corn oil) over 2 months (8), or intragastric ethanol feeding combined with Western diet (for 2 months)(27). Reversal of liver fibrosis was studied 1 month after CCl$_4$ cessation, and 7 weeks after withdrawal from alcohol feeding. Recurrent injury in Col-GFP mice was induced for 1 mo with CCl$_4$ (8×1:4). Liver injury in Rag$^{-/-}$γc$^{-/-}$ and Hspa1a/b$^{-/-}$ mice was gradually induced with CCl$_4$ (4×1:16; 2×1:8; 2×1:4) for 1 month. Collagen content is estimated by Hydroxyproline, Sirius Red staining. For PF studies Liver injury was induced in mice by intragastric gavage with carbon tetrachloride CCl$_4$ (1:4 dilution in corn oil, 60 µl×14 injections) or ligation of the common bile duct (3 weeks)

Adoptive Transfer of HSCs into Rag$^{-/-}$γc$^{-/-}$ Mice.
Primary HSCs were isolated from Collagen-α1(I)-GFP/β-actin-RFP double transgenic mice, uninjured or after cessation of CCl$_4$-induced injury (7 days or 1 mo) and adoptively transferred (2.2×10$^5$ cells) into 1 day old Rag2$^{-/-}$γc$^{-/-}$ pups by intrahepatic injection. One month later mice were gradually subjected to CCl$_4$-induced liver injury.

Isolation of Non-Parenchymal Cell Fraction and Primary HSCs:
Livers are perfused and digested using pronase/collagenase and gradient centrifugation method, as previously described (8). Freshly isolated HSCs were analyzed by flow cytometry, or cultured in DMEM (Gibco-BRL)+10% FCS, 2 mM L-glutamine+antibiotics. For PF studies Livers were perfused and digested using pronase/collagenase method. Singe-cell suspensions were centrifuged at 50 g for 5 minute to pellet the hepatocyte fraction. The remaining non-parenchymal cell fraction supernatant was collected and contained hepatic myofibroblasts (HSCs, portal fibroblasts and others), Kupffer cells, BM inflammatory cells and hepatic endothelial cells (HEC). aPFs and aHSCs were isolated using cell sorting for Col-GFP$^+$Vit.A$^-$ and Col-GFP$^+$Vit.A$^+$ cells. KC and EC were isolated by gradient centrifugation (15% Nycodenz) following by magnetic sorting with anti-CD11b and anti-CD31 antibodies, respectively (Miltenyi Biotec).

Flow Cytometry:
Flow cytometry was based on simultaneous detection of collagen-α1(I)-GFP and Vitamin A (autofluorescent signal detected by UV laser in Col-GFP mice. Phenotyping of the non-parenchymal fraction isolated from liver injured Col-GFP mice was performed on Canto (BD Bioscience Flow Cytometry Systems, BD). Activated myofibroblasts were visualized by GFP expression (488 nm) using argon laser, and Vitamin A$^+$ cells were visualized by autofluorescent signal (405 nm) detected by violet laser. Thy1.1-PE antibody (eBioscience) was used to distinguish PFs from HSCs. Cell sorting was performed on a MoFlo (Beckman Colter). Activated myofibroblasts were visualized by GFP expression (488 nm) using LYT-2005 laser (iCYP Visionary Bioscience Inc), and Vitamin A$^+$ cells were visualized by autofluorescent signal (350 nm) detected by UV laser (JDSU-Excyte).

Immunofluorescence and Immunohistochemistry.
Formalin-fixed frozen livers or isolated cells (fixed in 5% Paraformaldehyde in PBS) were stained with anti-desmin Ab (Thermo Scientific), anti-GFAP (Dako), anti-GFP Ab (Abcam), anti-SMA Ab (Abcam), anti-MHC II Ab, PECAM-1 (eBioscience), anti-PPARγ (Santa Cruz), anti-Hspa1a/b Ab (gift of Dr. Dillman) or isotype controls. Nuclei are stained with DAPI. Immunohstochemistry is performed using DAB staining (Vector). For PF studies Immunohstochemistry was performed using DAB staining (Vector), and counterstaining with Hematoxilin, Isolated cells were fixed in 5% Paraformaldehyde in PBS and stained with anti-Mesothelin antibody using MOM kit (Vector).

Generation of Transgenic Col-α1(I)$^{Cre}$ Mice.
Collagen-α1(I)$^{Cre}$ (Col-α1(I)$^{Cre}$) transgenic mice express Cre under the control of collagen-α1(I) promoter/enhancer. The transgenic construct was generated using pGL3(R2.1) basic Vector (Promega, Madison). Collagen-α1(I) promoter/enhancer was inserted into the plasmid using Kpn I and Bgl II restriction enzymes. Cre was inserted into EcoRI-EcoRI site. The transgenic construct was excised with Kpn I and Sal I unique restrictions enzymes and microinjected into fertilized C57BL/6J×CBA F1 hybrid embryos, which were implanted in pseudo-pregnant Swiss Webster foster mothers. The offspring (founders) were genotyped by PCR of genomic DNA for primers detecting Cre. All animal experiments were approved by the UCSD Institutional Animal Care and Use Committee.

Intragastric Ethanol Feeding Model of Liver Fibrosis, and Withdrawal from Ethanol Feeding.

Col-α1(I)$^{Cre-YFP}$ male and female (13 wks old) mice were first fed ad libitum "Western diet", a solid diet high in cholesterol and saturated fat (HCFD:1% w/w cholesterol, 21% Cal lard, 17% Cal corn oil) for 2 weeks. The mice were then operated for implantation of gastric catheters for intragastric feeding of liquid high fat diet (36% Cal corn oil) plus ethanol or isocaloric dextrose at 60% of daily caloric intake for 8 weeks for males and 10 weeks for females (27-29). During this intragastric feeding period, the mice continued to consume ad libitum HCFD for missing 40% of calories. Ethanol dose was increased from 19 to 32 g/kg/day. Similar level of fibrosis was achieved in males and females. Withdrawal from alcohol began by replacing HCFD with regular chow and gradually decreasing the ethanol dose within 7 days. The catheter was then cut off just above the dorsal exit site, and the animals were allowed to recover from alcoholic liver fibrosis for 7 weeks prior to sacrificing and isolation of hepatic stellate cells.

Adoptive Transfer of Primary HSCs into the Wild Type Mice.

Figure 6:
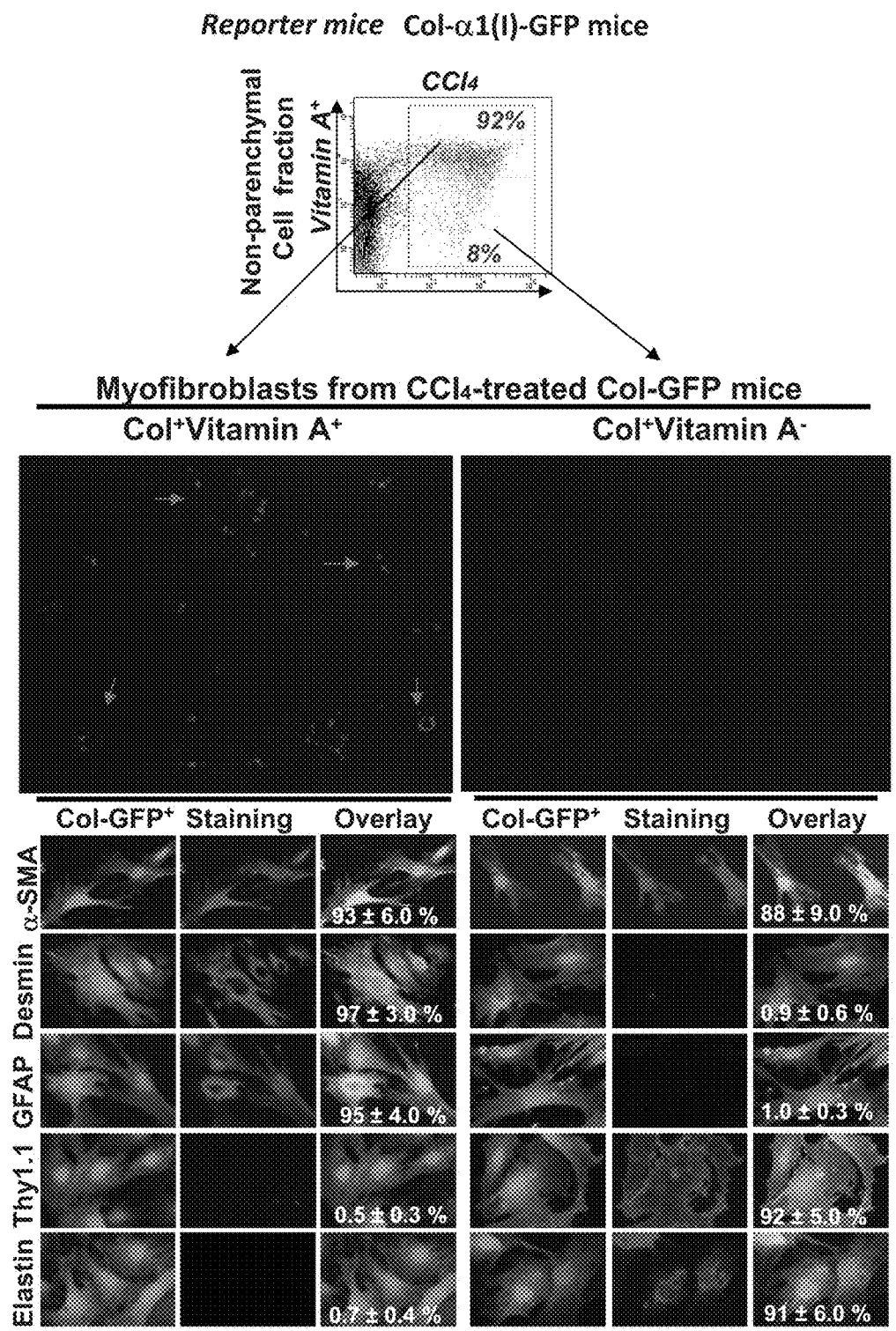
FIG. 6 shows HSCs are the major source of activated myofibroblasts in response to CCl$_4$-induced liver injury. A nonparenchymal fraction was isolated from CCl$_4$-treated Col-GFP mice. Activated myofibroblasts were identified by Col-GFP expression and sort purified. GFP+ myofibroblasts were then sort purified into two fractions: Vitamin A$^+$ and Vitamin K. Vitamin A$^+$GFP$^+$ and Vitamin A$^-$GFP$^+$ myofibroblasts were plated and cell composition was analyzed. Expression of Vitamin A was confirmed by fluorescent microscopy. Phenotyping of GFP$^+$ myofibroblasts by immunocytochemistry confirmed that >95% of Vitamin A$^+$GFP$^+$ express markers of HSCs (GFAP, Desmin), while >90% of Vitamin A$^-$GFP$^+$ express markers of portal fibroblasts. aHSCs (Vitamin A$^+$) constitute >90% of myofibroblasts (Vitamin A$^+$GFP$^+$), as detected by flow cytometry of the non-parenchymal cell fraction from CCl$_4$-treated (2 mo) Col-GFP mice (n=3).

Primary HSCs were isolated from Collagen-α1(I)$^{Cre-YFP}$ mice, uninjured or 2 weeks after cessation of $CCl_4$-induced injury and adoptively transferred (intrahepatically) into the wild type C57Bl6 male mice (12 w old, males, n=3/group), pre-treated with $CCl_4$ (4×1:4 dilution). HSCs from a single donor were transferred into one recipient mouse. Following the transfer, mice continued to receive $CCl_4$ (4×1:4 dilution) for 2 weeks to induce liver injury (see. FIG. 6B).

Whole Mouse Genome Gene Expression Microarray: The gene expression profile of HSCs was studied using WHOLE MOUSE GENOME MICROARRAY™ (Agilent). For this purpose, Vitamin A+YFP+ and Vitamin A+YFP− HSCs were sort purified from Collagen-a2(Ifre-YFP mice (8 fold) with no injury, after $CCl_4$ (2 mo.), and after 7 days or 1 mo recovery from $CCl_4$. In addition, Vitamin A+opp+ qHSCs were sort purified from Collagen-al(I)-GFP mice at day 14 postnataly. mRNA was purified using RNEASY™ columns (Qiagen, Valencia, Calif.), 160 ng of purified RNA per sample was labeled using the LRILAK PLUS™, two color low RNA input Linear Amplification kit and hybridized to a WHOLE MOUSE GENOME MICROARRAY™ 4×44K 60 mer slide according to the manufacturer's instructions (Agilent, Santa Clara, Calif.). The gene expression profile of BDL-(20 days) activated HSCs and PFs was compared to CCl4-activated HSCs was studied using WHOLE MOUSE GENOME MICROARRAY™ (Agilent). mRNA was purified using RNEASY™ columns (Qiagen, Valencia, Calif.), 160 ng of purified RNA per sample was labeled using the LRILAK PLUS, two color low RNA input Linear Amplification kit and hybridized to a WHOLE MOUSE GENOME MICROARRAY™ 4×44K 60 mer slide according to the manufacturer's instructions (Agilent, Santa Clara, Calif.). Slides were scanned using the Agilent GZ505B™ Scanner and analyzed using the GENE SPRING SOFTWARE™ (Agilent). Hierarchical clustering of gene expression values was performed using Cluster3.0 (30)) using the correlation coefficient as the similarity metric, and average linkage when merging nodes during tree building. Clustering was performed on genes expressed in at least one condition (>9 log 2 intensity value) to remove absent genes and genes exhibiting a standard deviation greater than 0.75 among log 2 intensity values to remove genes with constant expression. Hierarchical clustering results were visualized using Java Tree View (31)). Differentially regulated genes were defined as those with significant absolute expression (>9 log 2 intensity value) and exhibiting 2-fold compared to the maximal value in all other samples. Gene ontology and KEGG pathway functional enrichment analysis was performed using DAVID (32)).

Quantitative RT-PCR: Total RNA was isolated from purified HSCs using RNeasy columns (Qiagen, Valencia, Calif.), or total RNA was isiolated from the non-parenchymal fraction, hepatocyte fraction, or purified Coi+Vitamin A+ and Col+Vitamin A− cells using RNeasy columns (Qiagen, Valencia, Calif.). First strand cDNA was synthesized using SUPERSCRIPT III™ and random hexamers (Invitrogen, Carlsbad, Calif.). Samples were run in 20 ul reactions using an AB1 7300™ (Applied Biosystems, Foster City, Calif.). SYBR Green oligonucleotides were used for detection and quantification of genes. Gene expression levels were calculated after normalization to the standard housekeeping gene 18S using the CT method as described by the manufacturer (Invitrogen, Carlsbad, Calif.), and expressed as relative mRNA levels compared with control. The results are represented as average±SEM, p<0.0001.

Apoptosis of aHSCs. Apoptosis was induced in serum starved Hsp1a/b$^{-/-}$ and wild type HSCs by glyotoxin (25 nM for 4 h) or TNF-α (20 ng/ml for 18 h)+Actinomycin (0.2 μg/ml) (13, 14). Cell apoptosis was accessed by TUNEL$^+$ staining (Roche) and immunostaining for cleaved caspase-3 (Cell technologies. Inc.).

Laser capture micro dissection (LCM) and RNA extraction: Livers from sham-, CCl4- and BDL-injured mice were snap-frozen in FSC 22™ Frozen Section Media (Leica Microsystems) and stored at −80° C. Transverse sections (10 μm) were cut with a cryostat at −20° C. Cryosections were mounted on membrane-coated slides. A Leica LMD7000™ system (Leica Microsystems) was used to cut periportal or centrilobular area on sections. Microdissected sections were collected in the lid of a 0.5 ml microtube containing RLT buffer from the RNEASY™ (Qiagen). Total RNA was extracted using the same kit following the manufacturer's instructions.

Example 1—Regression of Liver Fibrosis is Accompanied by Loss of Myofibroblasts

A study was designed to determine the fate of aHSCs/myofibroblasts (α-SMA$^+$ColI$^+$ cells) during regression of hepatic fibrosis. For this purpose, reporter Col-GFP mice, expressing collagen-α1(I) promoter/enhancer-driven GFP, were subjected to $CCl_4$-induced liver injury for 2 months. After cessation of the toxic agent, mice recuperated for 1 or 4 months, and regression of liver fibrosis was evaluated by measuring collagen deposition and myofibroblast number (FIG. 1A-B). $CCl_4$-treated mice developed severe fibrosis with activated myofibroblasts (FIG. 1A-B), that decreased markedly after 1 mo. and 4 mo. of recovery. After 1 mo recovery, hydroxyproline levels and expression of fibrogenic genes collagen-α1(I) and α-SMA were significantly decreased, compared with $CCl_4$ treated mice (7.8±1.2% Col-GFP and 8±1.5% α-SMA, FIG. 1B), confirming that $CCl_4$-activated myofibroblasts disappear during recovery from liver fibrosis. Thus, Col-GFP mice undergo regression of liver fibrosis so that 1 month of recovery is appropriate to study the fate of aHSCs/myofibroblasts.

Example 2-Hepatic Stellate Cells are the Major Source of $CCl_4$-Activated Myofibroblasts The contribution of aHSCs to liver myofibroblasts in $CCl_4$-treated Col-GFP mice was determined using flow cytometry of the isolated non-parenchymal liver cell fraction, which contains aHSCs/myofibroblasts, inflammatory cells, and endothelial cells (8). Myofibroblasts were identified by Col-GFP expression, and HSCs were identified by Vitamin A expression (1, 4, 8) (detected at 405 nm as an autofluorescent signal quenched by a violet laser, FIG. 1C and FIG. 6). 92±3% of GFP$^+$ cells co-expressed Vitamin A, demonstrating that aHSCs represent the major population of fibrogenic myofibroblasts in $CCl_4$-injured liver, as predicted by previous qualitative studies (9). Therefore, aHSCs can be genetically labeled based on specific upregulation of type I collagen expression (FIG. 7) in $CCl_4$-induced liver fibrosis, since other cellular sources do not make a significant contribution to the myofibroblast population.

Collagen-GFP mice were also subjected to cholestatic (BDL) liver injury. Using this model activation of portal fibroblasts (PFs) prevailed over HSC in response to BDL. Moreover, BDL-induced PFs correlated with their increased activation (versus HSCs) and expression of fibrogenic genes ($\alpha$-SMA, collagen-$\alpha$1(I), TIMP-1, TGF-$\beta$1). Fibrogenic properties exhibited by BDL-induced PFs were comparable to that in $CCl_4$-induced HSCs.

Example 3-Some aHSCs Apoptose During Regression of Liver Fibrosis

Figure 8:
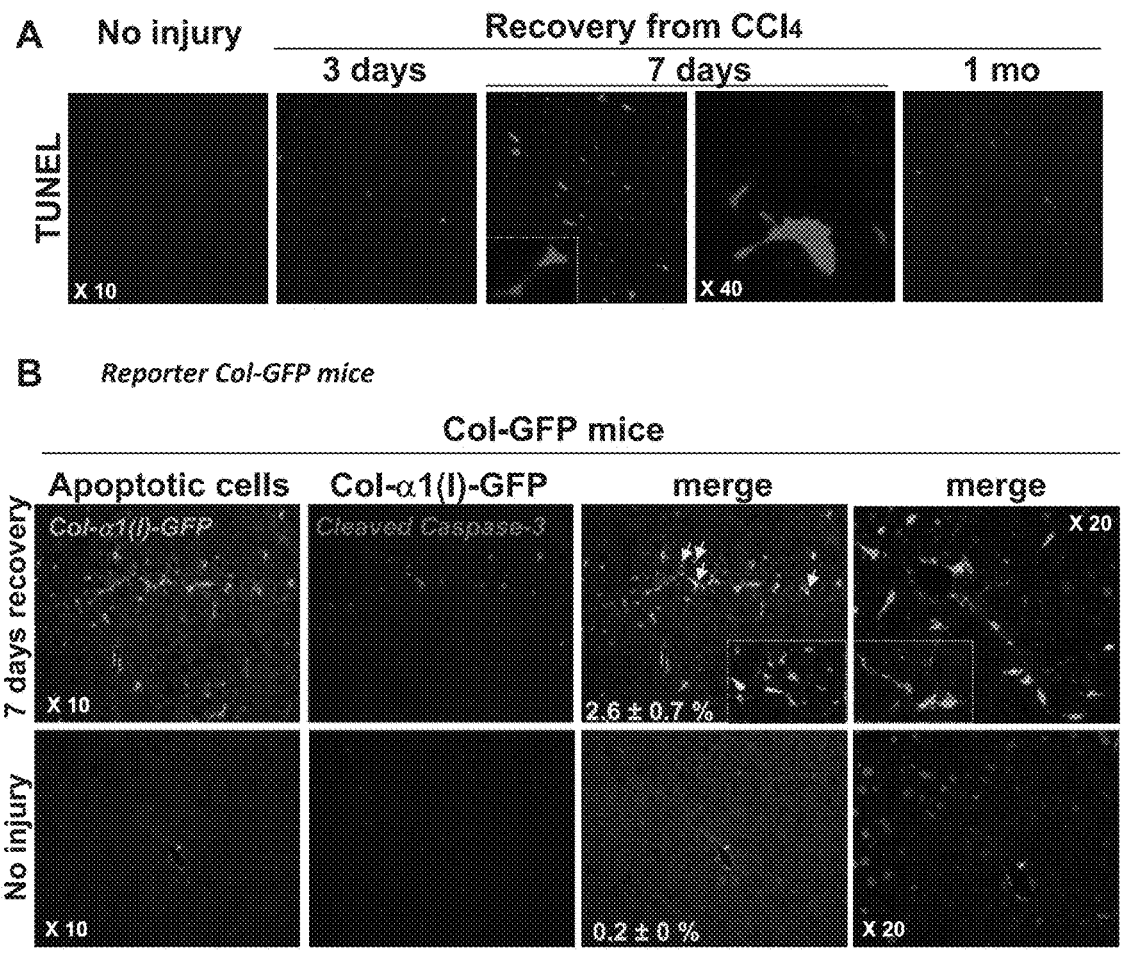
FIG. 8 shows some activated HSCs apoptose during recovery from liver fibrosis. A. Apoptotic TUNEL$^+$ (594 nm, Roche) cells were detected at the highest level after 7 days of recovery from CCl$_4$. Fluorescent micrographs are visualized using ×10 objective and ×40 objectives. B. Apoptotic aHSCs were identified by co-localization of immunostaining for cleaved caspase-3 in GFP$^+$ myofibroblasts in livers from Col-GFP mice, after 7 days of recovery from CCl$_4$ compared to uninjured mice (p<0.05). Fluorescent micrographs are shown using ×10, 20 and 40 objectives.

The disappearance of aHSCs/myofibroblasts during regression of liver fibrosis may result from either cell death by senescence (3) and apoptosis (2), inactivation (iHSCs), or both (FIG. 1D). Apoptosis of HSCs during regression of liver fibrosis is well documented (2). In agreement, we detected apoptotic aHSCs/myofibroblasts (2.6±0.7%) by co-localization of cleavable caspase-3$^+$ and GFP$^+$ cells in the livers of Col-GFP mice 7 days after $CCl_4$ cessation, when apoptosis of hepatic cells was highest (FIG. 8). Overall, early (7 days) recovery from liver fibrosis is accompanied by apoptosis of some aHSCs/myofibroblasts.

Figure 7:
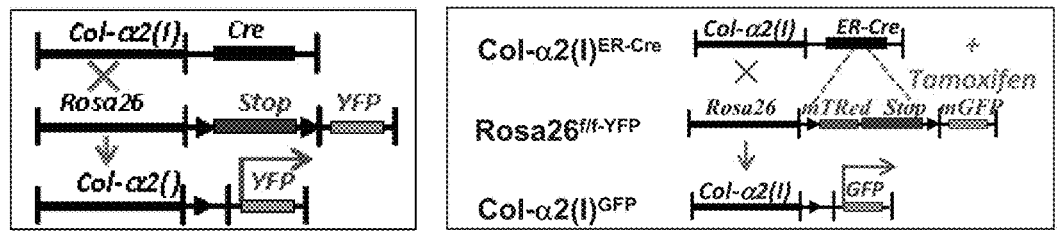
FIG. 7 shows genetic labeling of aHSCs in Col-$\alpha$2(I)$^{YFP}$ mice. Col-$\alpha$2(I)$^{YFP}$ mice were generated by crossing Collagen-$\alpha$2(I)$^{Cre}$ mice with Rosa26$^{fl/fl-YFP}$ mice. Upon activation of collagen promoter (during development or in response to CCl$_4$) Cre-LoxP recombination occurred and resulted in permanent labeling of aHSCs and their progeny by YFP expression.

Example 4—Genetically Labeled aHSCs/Myofibroblasts Persist in the Liver after 1 Mo of Recovery from $CCl_4$ To determine if some liver myofibroblasts survive the regression of fibrosis, Col-$\alpha$2(I)$^{Cre-YFP}$ mice (Collagen-$\alpha$2 (I)$^{Cre}$×Rosa26$^{flox-Stop-flox-YFP}$ mice, see FIG. 7) were treated with $CCl_4$ (2 mo), allowed to recover (1 mo) and then were analyzed for the persistence of genetically labeled YFP$^+$ cells (FIG. 2A). HSCs were identified by expression of GFAP and Desmin, and aHSCs/myofibroblasts were detected by expression of $\alpha$-SMA. 98±2% of HSCs were activated (expressed YFP) in response to $CCl_4$ treatment, and YFP expression was detected in 94±4% of myofibroblasts ($\alpha$-SMA$^+$). Although myofibroblasts had completely disappeared in livers after 1 mo recovery, YFP$^+$ cells surprisingly persisted. In particular, expression of YFP was detected in 38±8% of Desmin$^+$ and 41±5% of GFAP$^+$ cells, consistent with being HSCs that had been previously activated (FIG. 2A).

The immunoshistochemistry (FIG. 2A) and flow cytometry (FIG. 2B) of gradient purified HSCs from Col-$\alpha$2(I)$^{YFP}$ mice identified three HSC phenotypes 1) quiescent (qHSCs, Vitamin A$^+$YFP$^-$ $\alpha$-SMA$^-$), 2) activated (aHSCs, Vitamin A$^+$YFP$^+$$\alpha$-SMA$^+$), and 3) inactivated (iHSCs, Vitamin A$^+$YFP$^+$$\alpha$-SMA$^-$). After recovery from fibrosis, 56±4% of HSCs co-expressed YFP$^+$ and Vitamin A$^+$, indicating that these iHSCs had a history of Type I expression but reverted to an inactivated phenotype (FIG. 2B).

Figure 9:
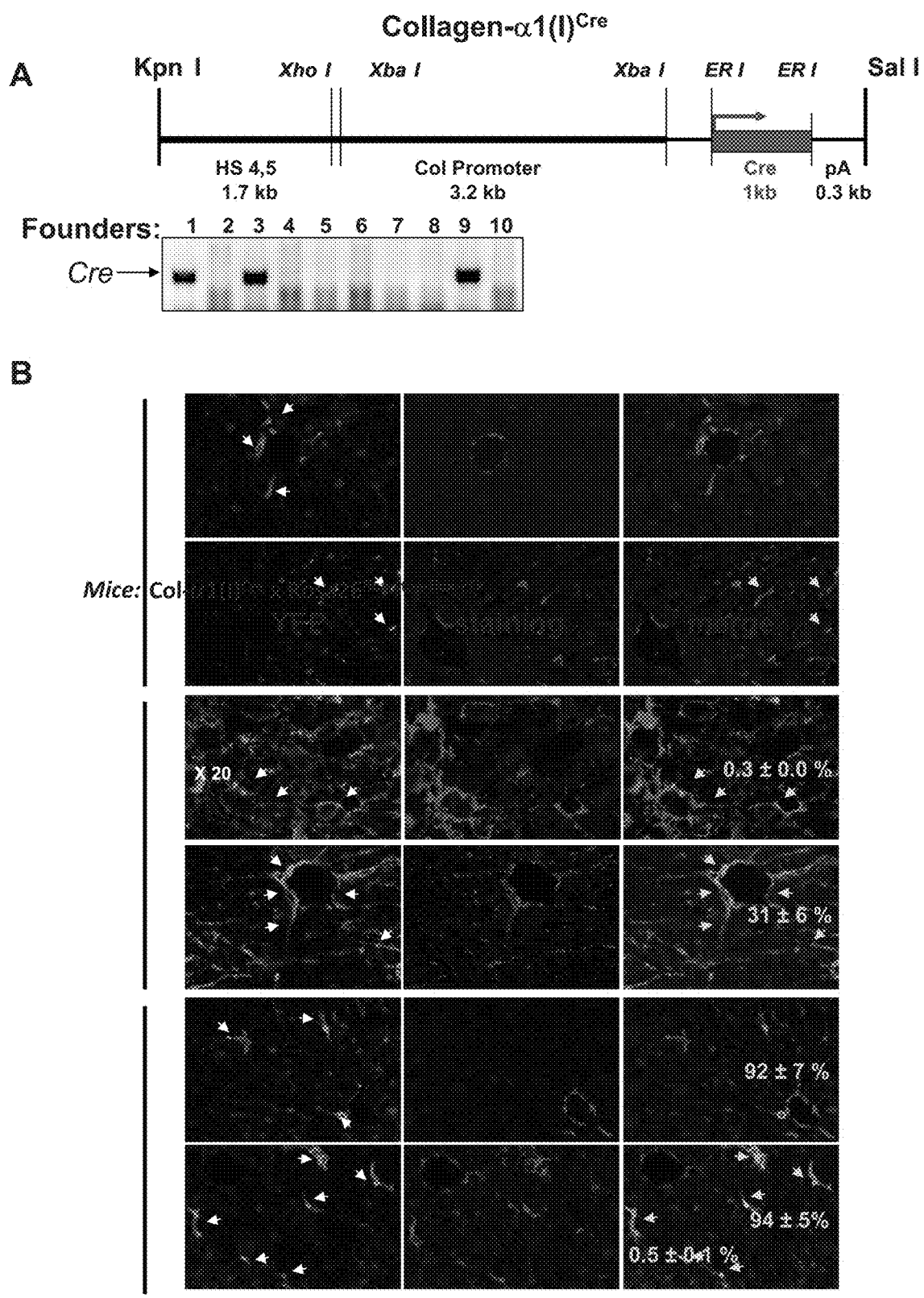
FIG. 9 shows genetically labeled YFP$^+$Desmin$^+$SMA$^-$ HSCs persist in livers of Collagen-$\alpha$1(I)$^{Cre-YFP}$ mice after 1 mo recovery from CCl$_4$. A. Generation of collagen-$\alpha$1(I)$^{Cre}$ mice. Transgenic construct consists of collagen-$\alpha$1(I) enhancer (1.7 kb) and promoter (3.2 kb), Cre gene (1 kb) and polyA site (0.3 kb). PCR of the genomic DNA has identified three founders. Founder N3 was used for this study. B. Livers from Collagen-$\alpha$1(I)$^{Cre-YFP}$ mice (no injury n=4; CCl$_4$-treated n=10; recovered 1 mo n=10) were co-stained for YFP, GFAP, Desmin and $\alpha$-SMA. Genetically labeled HSCs were identified after 1 mo recovery by YFP$^+$ expression in Desmin$^+$ or GFAP$^+$ cells. The number of YFP$^+$ HSCs is relative to total HSCs (100%, in yellow). p<0.04 (comparing CCl$_4$ and recovery groups). C. Livers from Col-$\alpha$1 (I)$^{Cre-YFP}$ mice were co stained for YFP and Desmin (or $\alpha$-SMA), and analyzed by confocal microscopy using ×60 objective. Genetically labeled inactivated HSCs were identified after 1 mo. recovery by YFP$^+$ expression in SMA$^-$ Desmin$^+$ cells. D. Livers from Col-$\alpha$1(I)$^{Cre-YFP}$ mice were co-stained for YFP and $\alpha$-SMA, and analyzed by fluorescent microscopy using ×20 objective. Genetically labeled inactivated HSCs were identified after 4 mo. recovery as YFP$^+$ SMA$^-$ cells. E. Vitamin A$^+$ HSCs from Col-$\alpha$1(I)$^{Cre-YFP}$ mice (no injury n=3; CCl$_4$-treated n=3; recovered 1 mo. n=3) were analyzed by flow cytometry. Genetically labeled HSC were identified by Vitamin A$^+$ and YFP$^+$ expression. Dot plots are shown, p<0.01 (comparing YFP$^+$ aHSC and YFP$^+$ iHSCs). F. Genetically labeled inactivated HSCs locate to the peri-sinusoidal space of Disse after 1 month recovery from CCl$_4$-induced fibrosis. Immunostaining for YFP and PECAM-1 was performed on formalin-fixed livers from Col-$\alpha$1(I)$^{Cre-YFP}$ mice and analyzed using ×20 objective. Nuclei are visualized by DAPI. Immunohistochemistry was performed on formalin-fixed livers from Col-$\alpha$1(I)$^{Cre-YFP}$ mice and analyzed using ×20 objective. YFP$^+$ cells are visualized by staining with anti-GFP Ab and DAB, and counterstaining with Hematoxilin.
Figure 9:
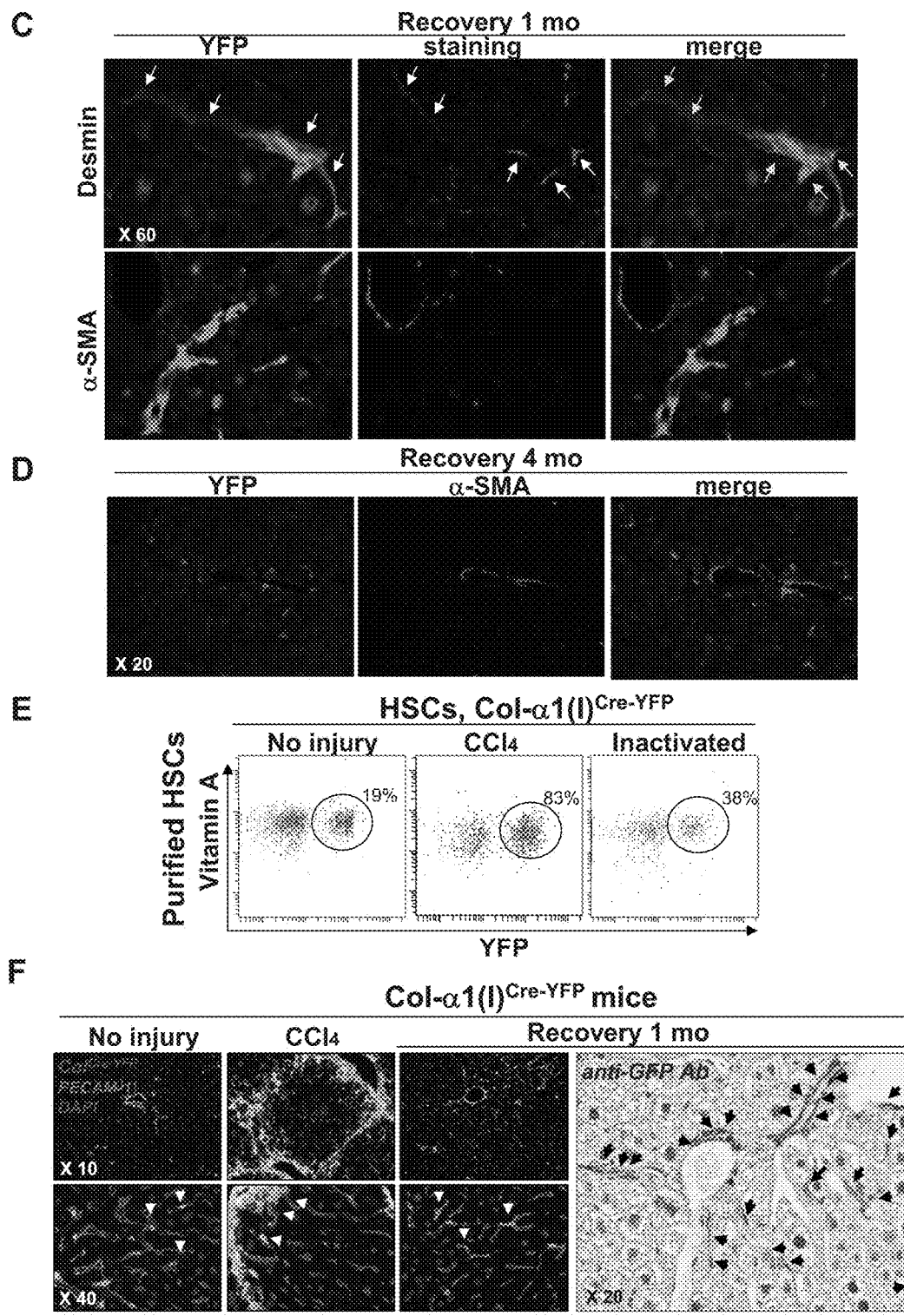

Collagen-$\alpha$2(I) and -$\alpha$1 (I) form a triple helix to produce collagen Type I and are co-expressed in aHSCs/myofibroblasts (10). To provide independent confirmation of the above findings, we used Col-$\alpha$1(I)$^{Cre-YFP}$ mice, generated by crossing collagen-$\alpha$1(I)$^{Cre}$ mice (FIG. 9A) with Rosa26$^{flox-Stop-flox-YFP}$ mice. As expected, $CCl_4$ treatment of Col-$\alpha$1(1)$^{Cre-YFP}$ mice produced aHSCs (Desmin$^+$YFP$^+$$\alpha$-SMA$^+$ cells; FIG. 9B-C). While $\alpha$-SMA$^+$ myofibroblasts were no longer detected in livers after 1 mo recovery, 37±9% of Desmin$^+$ HSCs still expressed YFP. In fact, genetically labeled YFP$^+$ HSCs persisted after 4 mo recovery (FIG. 9D). Similarly, flow cytometry demonstrated that 38±7% of YFP$^+$ Vitamin A$^+$ HSCs expressed YFP after 1 mo recovery, compared to 83±6% of YFP$^+$Vitamin A$^+$ aHSCs in fibrotic liver (FIG. 9E). In the recovered liver, these iHSCs resided in the peri-sinusoidal space of Disse and exhibited a stellate shape (FIG. 9F).

Example 5—HSCs Transiently Express Collagen Type I During Development

Figure 10:
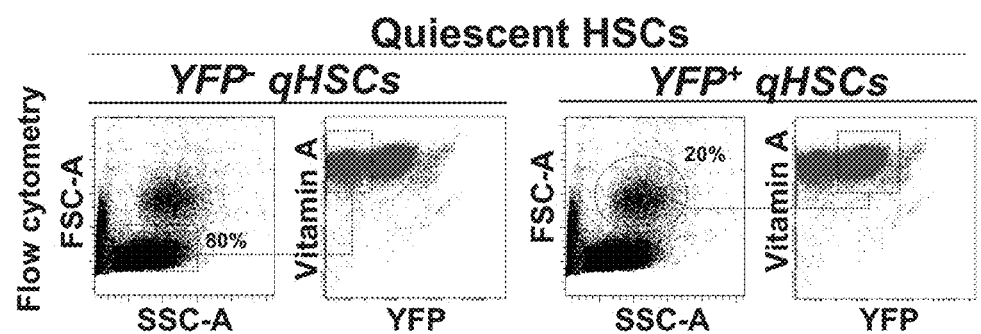
FIG. 10 shows some quiescent HSCs have a history of collagen expression during development. Quiescent HSCs were isolated from livers of Col-$\alpha$2(I)$^{Cre-YFP}$ mice (8 weeks old, n=3) and analyzed by flow cytometry. Genetically labeled Vitamin A$^+$YFP$^+$ HSCs (20%) were detected in HSC fraction (100%), and exhibited larger size and higher granularity, as demonstrated using forward (FSC-A) and side (SSC-A) scatter. Representative dot plots are shown.
Figure 11:
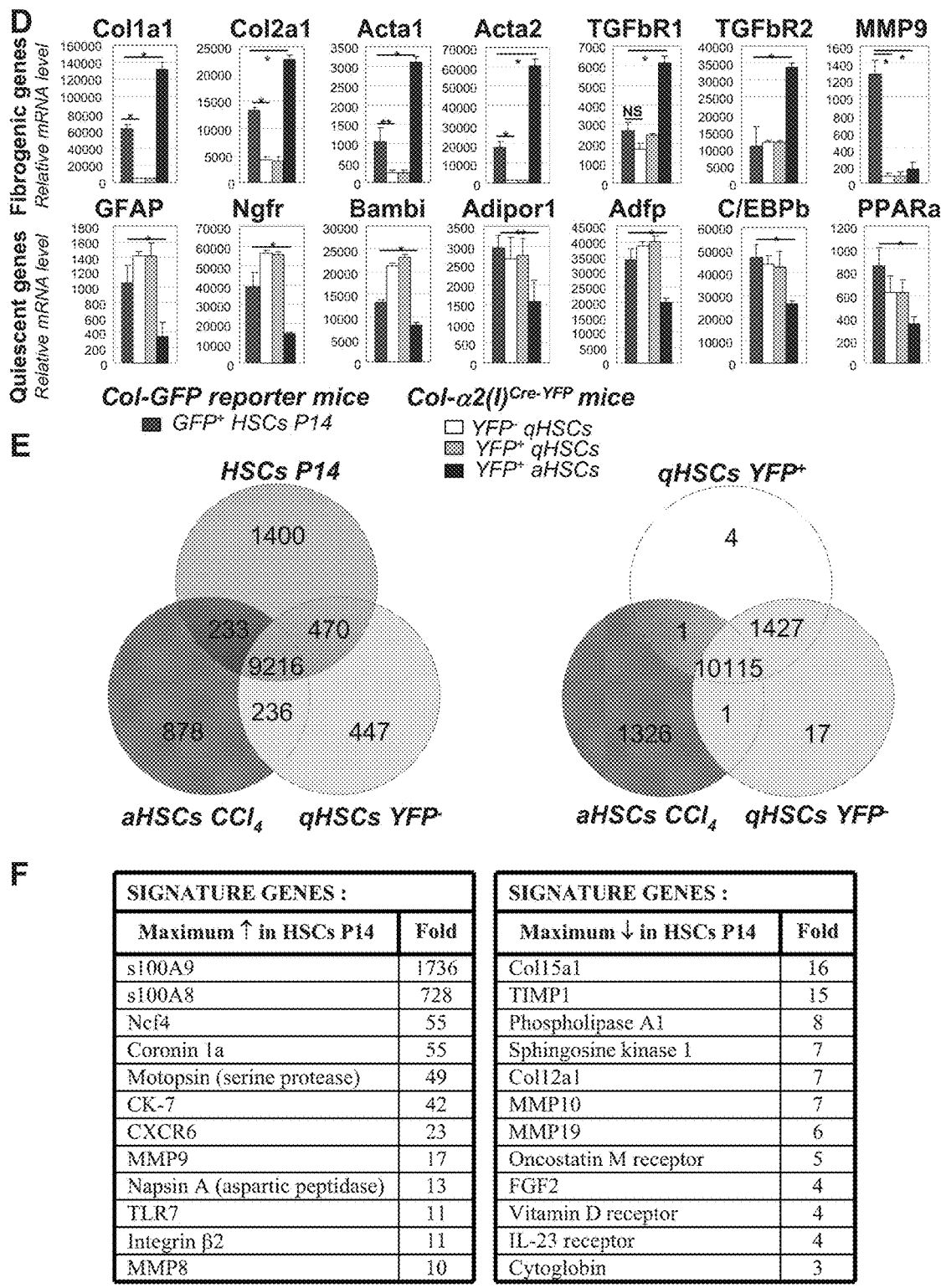
FIG. 11 shows that some HSCs transiently express collagen Type I during development. A. Livers from Col-GFP mice were obtained at day 16.5 of embryonic development (E16.5, n=5), and postnatally at day 1 (P1, n=4) and day 14 (P14, n=5), and compared to livers from adults (8 weeks old, uninjured or CCl$_4$-treated). GFP$^+$ cells were detected in livers of E16.5-P14 mice (but not in uninjured adult mice), and were scattered throughout the acini (fluorescent micrographs, ×10 objective). In contrast to CCl$_4$-treated adult mice, the Col-GFP mice at E16.5-P14 did not have fibrosis (Sirius Red staining, bright field micrographs, taken using ×10 objective). The number GFP$^+$ cells were minimal (or absent) at E12.5 and P25 (not shown). CV-central vein. B. Livers from Col-GFP mice at P14 were stained for HSC markers. 46±8% of all Desmin$^+$ (100%) HSCs/myofibroblasts expressed GFP. Similarly, 49±6% of GFAP$^+$ HSCs/ myofibroblasts expressed GFP$^+$. Expression of $\alpha$-SMA was only detected around blood vessels in 3±1.5% of GFP$^+$ cells. Fluorescent micrographs, images are taken using ×20 and ×60 objectives. C. HSCs were isolated from livers of Col-GFP mice using cell sorting for Vitamin A$^+$ and GFP$^+$ cells (n=4). Expression of GFP was detected in 38±4% of Vitamin A$^+$ cells. Representative dot plots are shown. Sort purified Vitamin$^+$GFP$^+$ cells were plated for 18 h and stained for HSC markers. Vitamin$^+$GFP$^+$ cells expressed Desmin and GFAP. Fluorescent micrographs, ×40 objective. D. Microarray analysis: Vitamin A⁺GFP⁺ HSCs (P14) were sort purified from Col-GFP mice, and their gene expression profile was analyzed by the whole mouse genome microarray. Vit.A⁺GFP⁺ qHSCs (P14) were compared to 1) qHSCs with a history of collagen expression (YFP⁺, n=3) from uninjured Collagen-α2(I)$^{Cre-YFP}$ mice; 2) qHSCs with no history of collagen expression (YFP⁻, n=3); and 3) aHSCs (YFP⁺, n=6) from CCl₄-treated Collagen-α2(I)$^{Cre-YFP}$ mice. HSCs (P14) expressed collagen Type I and α-SMA at levels higher than in qHSCs but lower than in aHSCs. The results are relative mRNA level (average of normalized values/multiple probes/gene) obtained by Agilant microarray, *p<0.01, **p<0.001. E. Venn diagrams of the cell group-enriched genes that exhibited >2 fold up-regulation as compared to other groups. Vit.A⁺GFP⁺ HSCs (P14) are compared to YFP⁻ qHSCs and YFP⁺ aHSCs (left diagram). In addition, YFP⁻ and YFP⁺ qHSCs are compared to each other and to YFP⁺ aHSCs. The numbers of genes without group-specific expression are shown in the middle areas. F. Expression of signature genes (upregulated or downregulated) in Vit.A⁺ GFP⁺ HSCs (P14) was determined in comparison with the average value of gene expression in qHSCs and aHSCs, and fold induction is shown for each group.

Detection of YFP$^+$ qHSCs in Col-$\alpha$2(1)$^{Cre-YFP}$ and Col-$\alpha$1(I)$^{Cre-YFP}$ in adult livers prior to injury (FIG. 2B, FIGS. 9E & 10) may reflect transient collagen gene expression activating Cre during development. To prove this hypothesis, expression of collagen-$\alpha$1(I) in real time was examined in livers of Col-GFP mice during embryogenesis (FIG. 10). Indeed, transient expression of collagen-$\alpha$1(I)-GFP was detectable in HSCs, identified by Vitamin A, Desmin and GFAP expression, between embryonic E16.5—postnatal day 14 (P14, FIG. 11A). At postnatal day 14, 46±8% of HSCs upregulated collagen-$\alpha$1(I)-GFP in real time but lacked $\alpha$-SMA expression (FIG. 11B). These GFP$^+$ HSCs did not exhibit characteristics of myofibroblasts (FIG. 11C-D), but were more similar to qHSCs than to aHSCs (FIG. 11E-F).

The fate of embryonic collagen$^+$ HSCs was examined in adult Col-$\alpha$2(1)$^{Cre-YFP}$ mice (8 w old). Consistent with our findings, YFP$^+$ qHSCs with a history of collagen expression and YFP$^-$ qHSCs had identical gene expression profiles characteristic of a quiescent phenotype (FIG. 11E).

Example 6—Tamoxifen-Induced Genetic Labeling of aHSCs/Myofibroblasts in Adult Mice Confirmed their Persistence in the Liver after 1 Mo of Recovery from $CCl_4$ Tamoxifen-inducible Col-$\alpha$2(I)$^{ER-Cre-GFP}$ mice were generated by crossing Col-$\alpha$2(I)$^{ER-Cre}$ mice× Rosa26$^{flox-mTRed-Stop-flox-mGFP}$ mice (FIG. 7). Genetic labeling of HSCs was achieved in adult $CCl_4$-treated Col-$\alpha$2(1)$^{Er-Cre-GFP}$ mice by daily tamoxifen administration during the last week of $CCl_4$ treatment (FIG. 12A). Genetically labeled aHSCs were visualized by loss of mTRed expression and gain of GFP expression upon Cre-loxP recombination. 35±6% of Desmin$^+$ HSCs expressed GFP after $CCl_4$, and 14±4% of HSCs were still GFP$^+$ after 1 mo. recovery (FIG. 2C), confirming that $CCl_4$-activated HSCs (and their progeny) persist in the liver after regression of fibrosis. Consistently, GFP+ iHSCs expressed Desmin, but not α-SMA (FIG. 12B). Thus, three independent transgenic mice demonstrated that aHSCs/myofibroblasts revert to an inactive phenotype during regression of fibrosis.

Example 7—Livers Recovering from Fibrosis have Fewer HSCs

Figure 13:
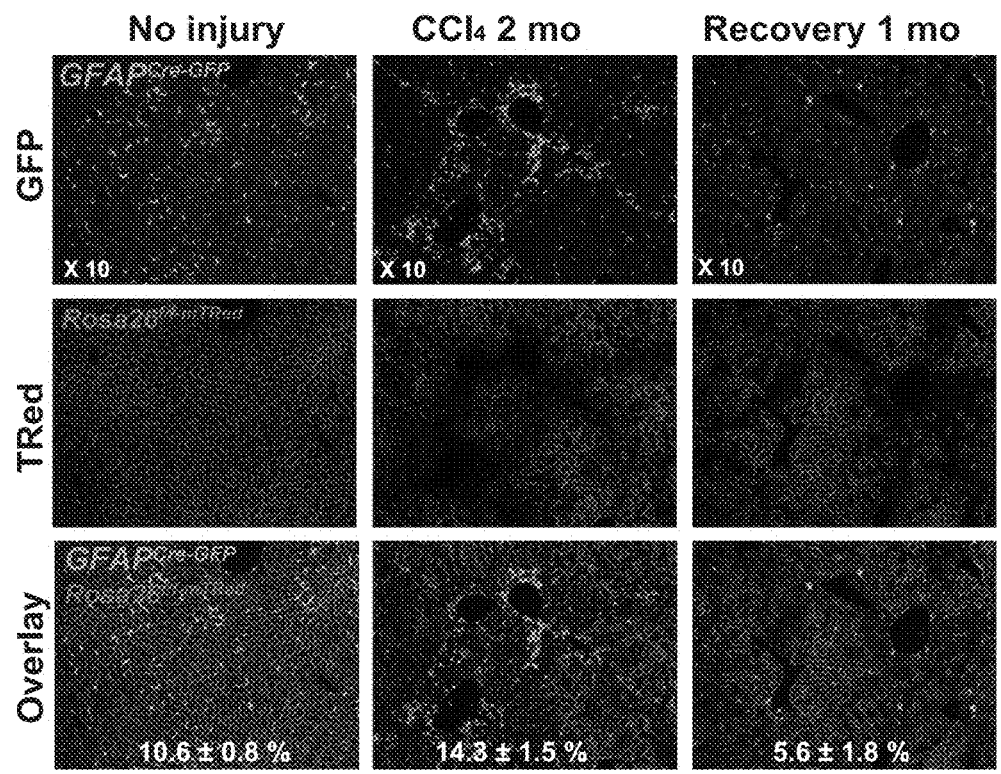
FIG. 13 shows recovery from liver fibrosis is associated with a reduced number of HSCs. A. GFAP$^{Cre-GFP}$ mice were generated by crossing GFAP$^{Cre}$ mice with Rosa26$^{flox-mTred-Stop-flox-mGFP}$ mice (here labeled as Rosa26$^{f/f-mTRed-mGFP}$ mice). Livers from GFAP$^{Cre-GFP}$ mice (no injury n=3; CCl₄-treated n=5; recovered 1 mo n=5) were analyzed by fluorescent microscopy, and genetically labeled HSCs were visualized as membrane tagged GFP⁺ (mTRed⁻) cells. The number of GFP⁺ HSCs is expressed relative to total liver cells (100%, in white). B. Quantification of genetically labeled HSCs in liver sections. The number of genetically labeled HSCs with a history of collagen expression (Col-α2(I)$^{Cre-YFP}$ & Col-α1(I)$^{Cre-YFP}$ mice), or all HSCs (GFAP$^{Cre-GFP}$ mice) is calculated as percent of total DAPI liver cells (100%).

To quantify the number of HSCs during fibrosis and its regression, we generated GFAP$^{Cre-GFP}$ mice (GFAP$^{Cre}$ mice×Rosa26$^{flox-Stop-mTRed-flox-mGFP}$ mice, FIG. 13A). In uninjured mice, qHSCs were distributed throughout the hepatic acinus and represented 10.6±0.8% of total liver cells. CCl$_4$ induced HSC activation, proliferation (14.3±1.5% of total liver cells), and accumulation of aHSCs in the pericentral area. One month after recovery, the number of HSCs was reduced (5.6±1.8% of total liver cells), and the distribution of HSCs was again similar to qHSCs. Based on immunostaining for GFAP after recovery from fibrosis in Col-α2(I)$^{Cre-YFP}$ and Col-α1(I)$^{Cre-YFP}$ mice (FIG. 2B, FIG. 9E), iHSCs constitute 2% of total liver cells in the recovered liver (FIG. 13B).

Figure 14:
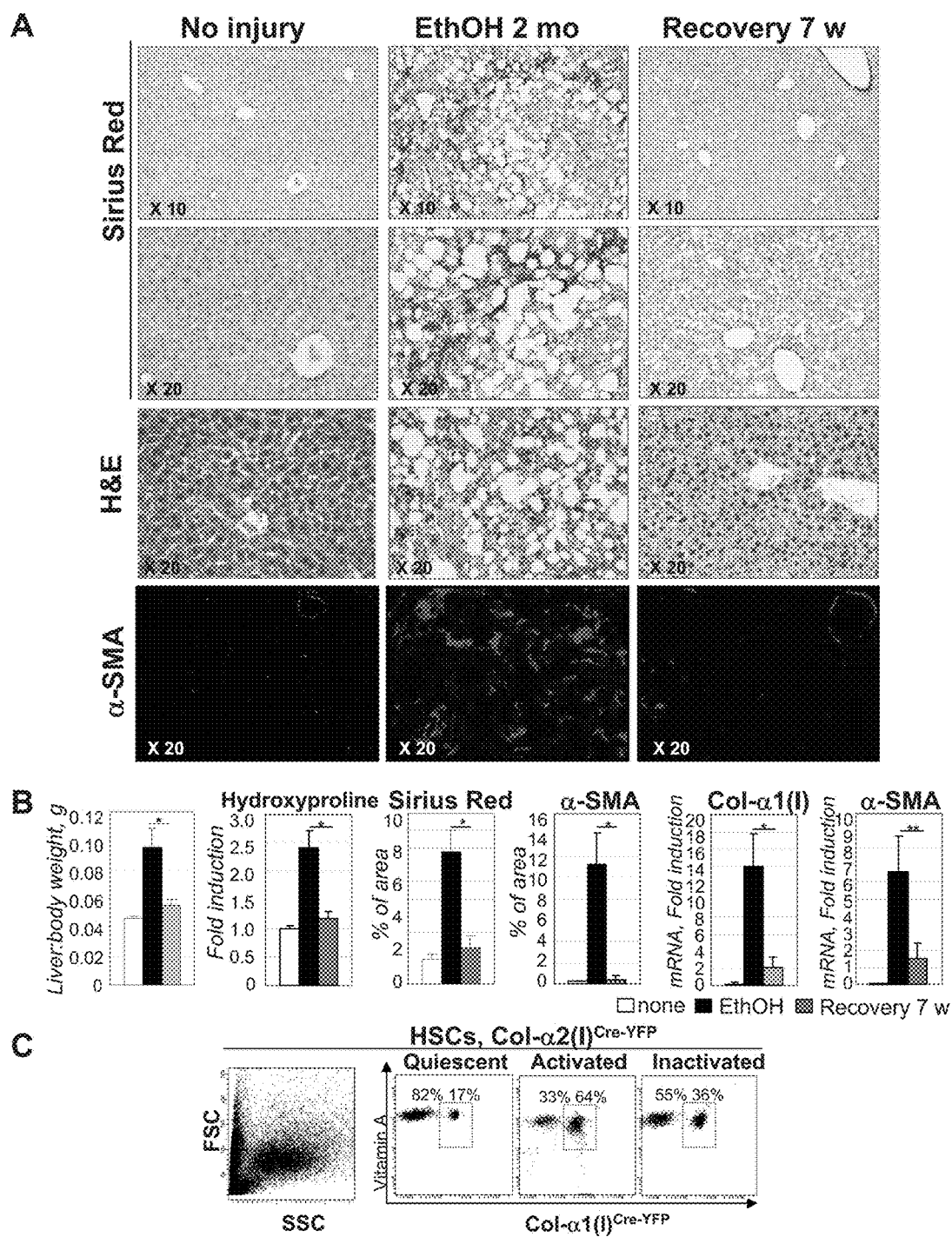
FIG. 14 shows genetically labeled YFP⁺Desmin⁺SMA⁻ HSCs persist in livers of Collagen-α2(I)$^{Cre-YFP}$ mice 7 weeks after withdrawal from alcohol-injury. A. A comparison of the livers of Col-α2(I)$^{Cre-YFP}$ mice (Col-α2(I)$^{Cre}$ mice×Rosa26$^{flox-Stop-flox-YFP}$ mice) that were untreated (n=4), alcohol-fed (EtOH, 2 mo, n=4), or withdrawn from alcohol-feeding (7 weeks, n=8) with respect to YFP expression, Sirius Red staining, H&E and α-SMA immunohistochemistry. Representative bright field and fluorescent micrographs are shown using ×10 and ×20 objectives. B. Quantification of same four groups in (A) with respect to ratio liver weight/body weight, hydroxyproline content, Sirius Red staining, α-SMA immunofluorescence, GFP expression, collagen α1(I) mRNA level, and α-SMA mRNA level, *p<0.001, **p<0.005. C. Genetically labeled HSCs/myofibroblasts are detected in livers of mice recovered from alcohol-induced liver fibrosis. HSCs (Vitamin A⁺) from Collagen-α2(I)$^{Cre-YFP}$ mice (no injury n=4; CCl₄-treated n=6; recovered 1 mo n=6) were analyzed by flow cytometry. Genetically labeled aHSC and iHSCs were identified by simultaneous Vitamin A⁺ and YFP⁺ expression. Dot plots are shown, p<0.01 (comparing YFP⁺ aHSC and YFP⁺ iHSCs). D. Livers from Collagen-α2(I)$^{Cre-YFP}$ mice (no injury n=4; intragastric alcohol feeding (EtOH) n=4; recovery 7 weeks n=8) were co-stained for YFP, GFAP, Desmin, α-SMA. Genetically labeled HSCs were identified after recovery from fibrosis by YFP⁺ expression in Desmin⁺ or GFAP⁺ cells. The number of YFP⁺ HSCs is calculated relative to total HSCs (100%; alcohol-fed and recovery groups are compared, p<0.05). E. HSCs from Col-α2(1)$^{Cre-YFP}$ mice were isolated after alcohol induced liver injury (EtOH; 2 mo.) or after 7 weeks recovery, cultured for 18 h, and analyzed for expression of Desmin, α-SMA, and synemin in genetically labeled YFP⁺ HSCs. Representative images are taken using ×40 objective.

Example 8—Genetically Labeled aHSCs/Myofibroblasts Persist in the Liver after 7 Weeks of Recovery from Alcohol-Induced Liver Fibrosis It was determined if survival of aHSCs/myofibroblasts occurs during regression of alcohol induced liver fibrosis. Liver fibrosis (and steatosis) was induced in Col-α2(I)$^{Cre-YFP}$ mice (Collagen-α2(I)$^{Cre}$× Rosa26$^{flox-Stop-flox-YFP}$ mice) by intragastric alcohol feeding for 2 months (FIG. 14A-B). Liver fibrosis (and steatosis) regressed in these mice 7 weeks after withdrawal from ethanol feeding. Flow cytometry demonstrated that genetic labeling (YFP+) was achieved in 64±5% of myofibroblasts, and persisted in 36±4% of Vitamin A+YFP HSCs upon recovery from fibrosis (FIG. 14C). These findings were confirmed by immunohistochemistry (FIG. 14D-E). YFP expression persisted in 38±7% of Desmin+ HSCs/myofibroblasts following regression of liver fibrosis after withdrawal from ethanol, despite the disappearance of myofibroblasts (α-SMA expressed in 1.4±1% of YFP HSCs/myofibroblasts, FIG. 14D). Thus, two models of regression of liver fibrosis demonstrate survival of iHSCs.

Figure 3:
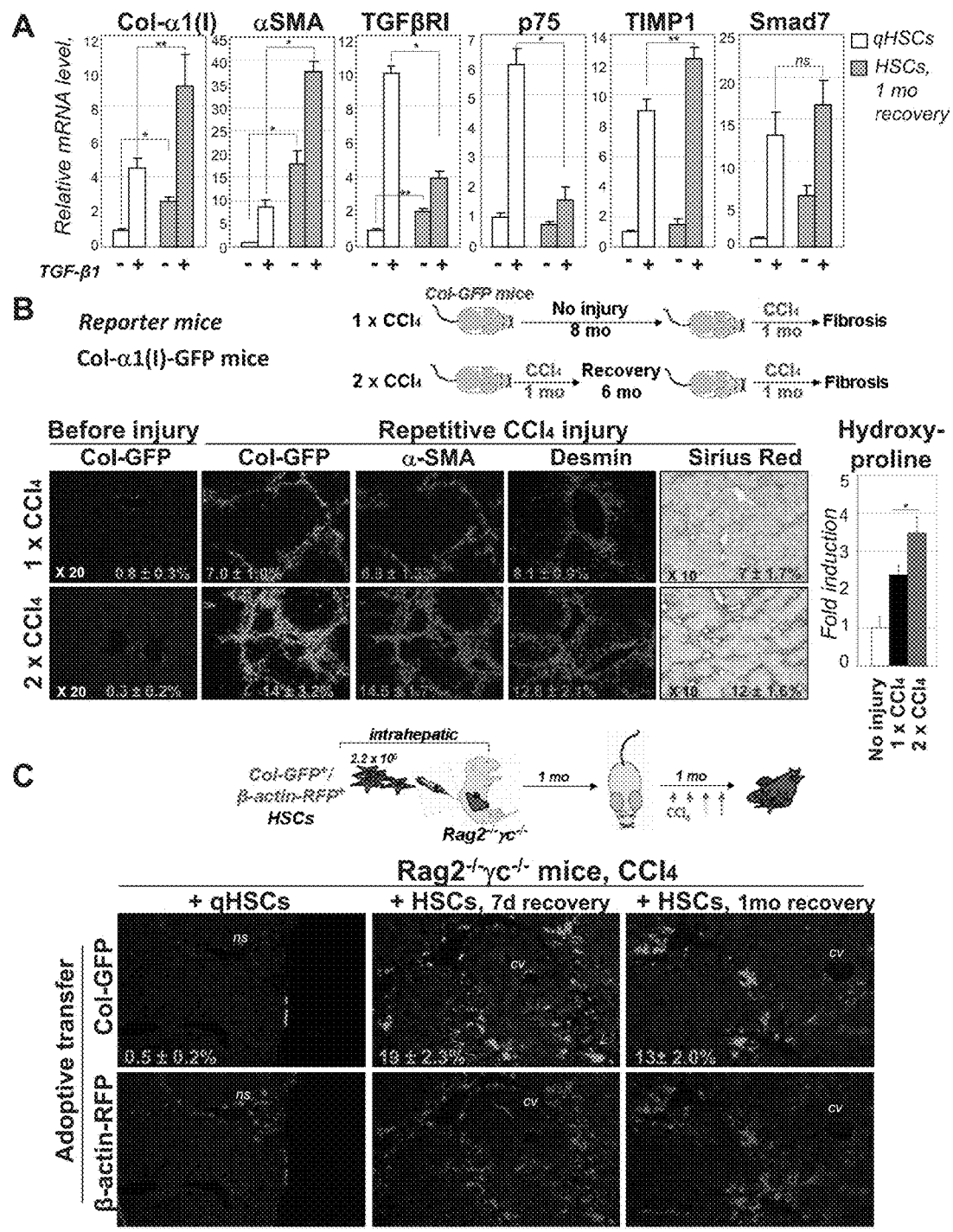
FIG. 3 shows HSCs (1 mo recovery) acquire a new phenotype distinct from qHSCs. A. HSCs from Col-α1(1)$^{Cre-YFP}$ mice, uninjured or after 1 mo. recovery, were cultured for 48 h±TGF-β1 (2 ng/ml, for 6 h), and analyzed by RT-PCR for expression of fibrogenic and neural genes, *p<0.01, **p<0.05. B. CCl$_4$-treated Col-GFP mice (2×CCl$_4$; n=4) recuperated for 6 mo., then subjected to recurrent CCl$_4$-injury. Development of liver fibrosis in these mice was compared to littermates treated with CCl$_4$ only the second time (1×CCl$_4$, n=4) by Sirius Red. The number of aHSCs was estimated by fluorescent microscopy for Desmin and α-SMA (p<0.05, using ×20 objective). Total collagen deposition was measured by Hydroxyproline assay, *p<0.01. C. HSCs were isolated from Collagen-α1(I)-GFP/β-actin-RFP mice, uninjured or after recovery (7 days or 1 mo) from CCl$_4$ injury, and transferred intrahepatically (2.2× 10$^5$ cells) into 1 day old Rag2$^{-/-}$γc$^{-/-}$ pups. Following CCl$_4$-injury, the number of RFP$^+$GFP$^+$ engrafted qHSCs, HSCs after 7 days and 1 mo. was calculated relative to number of total HSCs (detected by Desmin).
Figure 15:
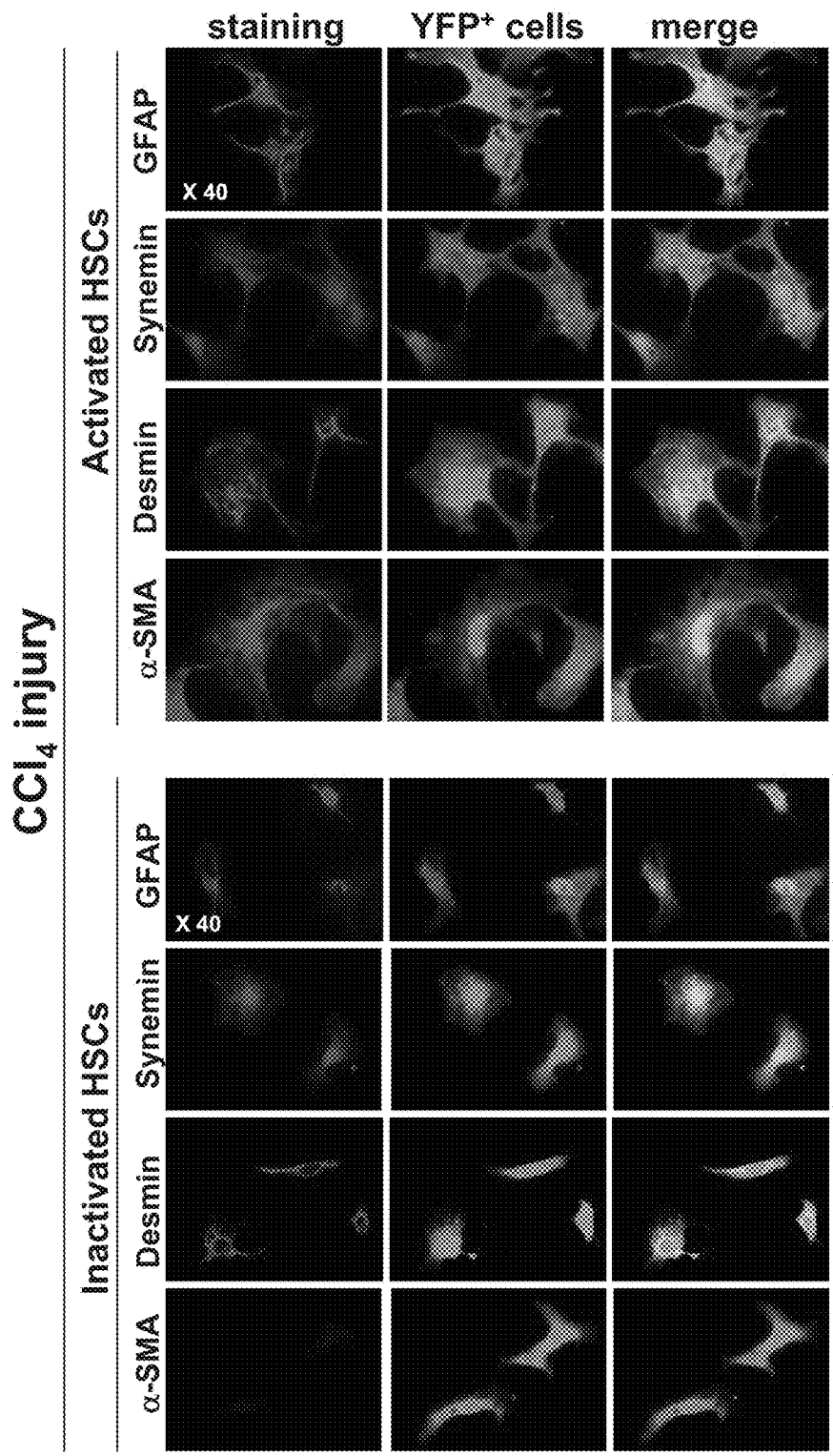
FIG. 15 shows purified iHSCs exhibit a similar phenotype as qHSCs. HSCs from Col-α1(1)$^{Cre-YFP}$ mice were isolated after CCl₄-injury (2 mo.) or after 1 mo recovery, cultured for 18 h, and genetically labeled YFP⁺ iHSCs were analyzed by fluorescent microscopy for expression of HSC marker Desmin, α-SMA, and neural marker synemin. Representative images are taken using ×40 objective.

Example 9—iHSCs Demonstrate an Increased Response to Repeated Fibrogenic Stimuli Purified iHSCs had a similar phenotype as qHSCs (Desmin+, GFAP+, Synemin+, α-SMA−, FIGS. 14E & 15). However, expression of myofibroblast-specific genes (Col-α1(I), α-SMA, TIMP-1) was induced more strongly in cultured TGF-β1-treated iHSCs than in qHSCs (FIG. 3A). In concordance, Col-GFP mice subjected to two rounds of CCl$_4$ injury separated by a 6-month interval to allow complete recovery (2×CCl$_4$) developed more severe fibrosis than littermates treated with one round of CCl$_4$ (1×CCl$_4$, FIG. 3B). Thus, culture and in vivo data indicated that iHSCs with a history of activation are more effectively activated than qHSCs.

Example 10-Adoptively Transferred HSCs (1 Mo Recovery), but not qHSCs, Contribute to Liver Fibrosis in Mice To test this hypothesis, HSCs were isolated from Col-GFP+/β-actin-RFP+ mice that were uninjured or after recovery from CCl$_4$-induced fibrosis (7 days, 1 month), and adoptively transferred into livers of the newborn Rag2$^{-/-}$γc$^{-/-}$ mice (11) (FIG. 3C). One month later, these Rag2$^{-/-}$γc$^{-/-}$ mice were subjected to CCl$_4$-injury, and fibrotic livers were analyzed for the presence of GFP+RFP+ HSCs. Highest engraftment (70-78%) was achieved in mice transplanted with HSCs after 7 d or 1 mo recovery (versus qHSCs, 50%; FIG. 16A). Unlike qHSCs, which were mostly scattered under the capsule or in liver parenchyma and constituted only 0.5±0.2% of total HSCs, HSCs from the recovering livers were incorporated into the myofibroblast population in recipient mice, and contributed 19±2.3% and 13±2.0% of total HSCs, respectively (FIG. 3C). Moreover, despite poor engraftment, comparable results were observed in CCl$_4$-treated wild type mice adoptively transferred with qHSCs or HSCs (2 w recovery) from Col-α1(I)$^{Cre-YFP}$ mice (FIG. 16B). Taken together, iHSCs are primed to differentiate into myofibroblasts more rapidly in response to recurrent stimuli.

Example 11—Inactivated HSCs Gradually Down Regulate Collagen-α1(I)

To further characterize iHSCs, Col-al (Ifre-YFP mice were crossed with Col-GFP mice, and genetically labeled HSCs (YFP+) were analyzed for expression of collagen-(α1 (I)) in real time (GFP+, FIG. 17). Following CCl$_4$ treatment (2 mo, FIG. 17A), all YFP+ HSCs expressed GFP. After 1 mo. recovery from fibrosis, YFP+ HSCs had decreased GFP expression. Similar results were obtained by flow cytometry (FIG. 17B-C), which allowed simultaneous detection of Vitamin A, YFP and GFP expression (12) in isolated HSCs. As expected, qHSCs lacked GFP expression and HSCs expressed GFP in response to CCl$_4$ (87±5%, FIG. 17B). Following a 2 week recovery from CCl$_4$, decreased GFP expression was observed in 75±3% of HSCs, of which 92±4% still expressed YFP. The mean fluorescent intensity (mfi) of GFP expression was strongly reduced in YFP+ HSCs at this time (approximately 4×10$^3$ mfi, compared to aHSCs : : : 6×10$^4$ mfi; FIG. 17B). GFP expression (approximately 1×10$^3$ mfi) decreased further in 42±4% of HSCs after 1 mo recovery and correlated with the number of YFP+ iHSCs (55±3%). Thus, inactivation of HSCs occurs gradually and steadily during recovery from CCl$_4$-induced fibrosis. Interestingly, 45% of HSCs after 1 mo. recovery had no history of collagen expression (YFP−), and represent new qHSCs (FIG. 17B).

Example 12—iHSCs Acquire a New Phenotype Distinct from qHSCs

To assess changes in global gene expression, inactivated YFP HSCs (iHSCs, 1 mo recovery) were evaluated by the whole mouse genome microarray and compared to qHSCs, aHSCs and HSCs after 7-days recovery (FIG. 4A). We confirmed that YFP iHSCs downregulated fibrogenic genes (Col-1α1, Col-1α2, Col-1α1, α-SMA, TGFβRI and TIMP1) during recovery from fibrosis, but failed to obtain a quiescent phenotype (upregulated PPARγ and Bambi, but not other quiescence-associated genes Adfp, Adipor1, or GFAP (5), FIG. 4B). Unsupervised clustering of gene expression profiles revealed that YFP+ iHSCs (1 mo.) exhibit an intermediate profile between that of qHSCs and YFP+ HSCs (7 days recovery), but share more similarity to qHSCs than aHSCs (FIG. 4C-D). Similar results were obtained using correlation coefficient analysis comparing expression profiles to qHSCs (FIG. 4C), and unsupervised clustering of gene-specific expression profiles (FIG. 18A-C).

Figure 5:
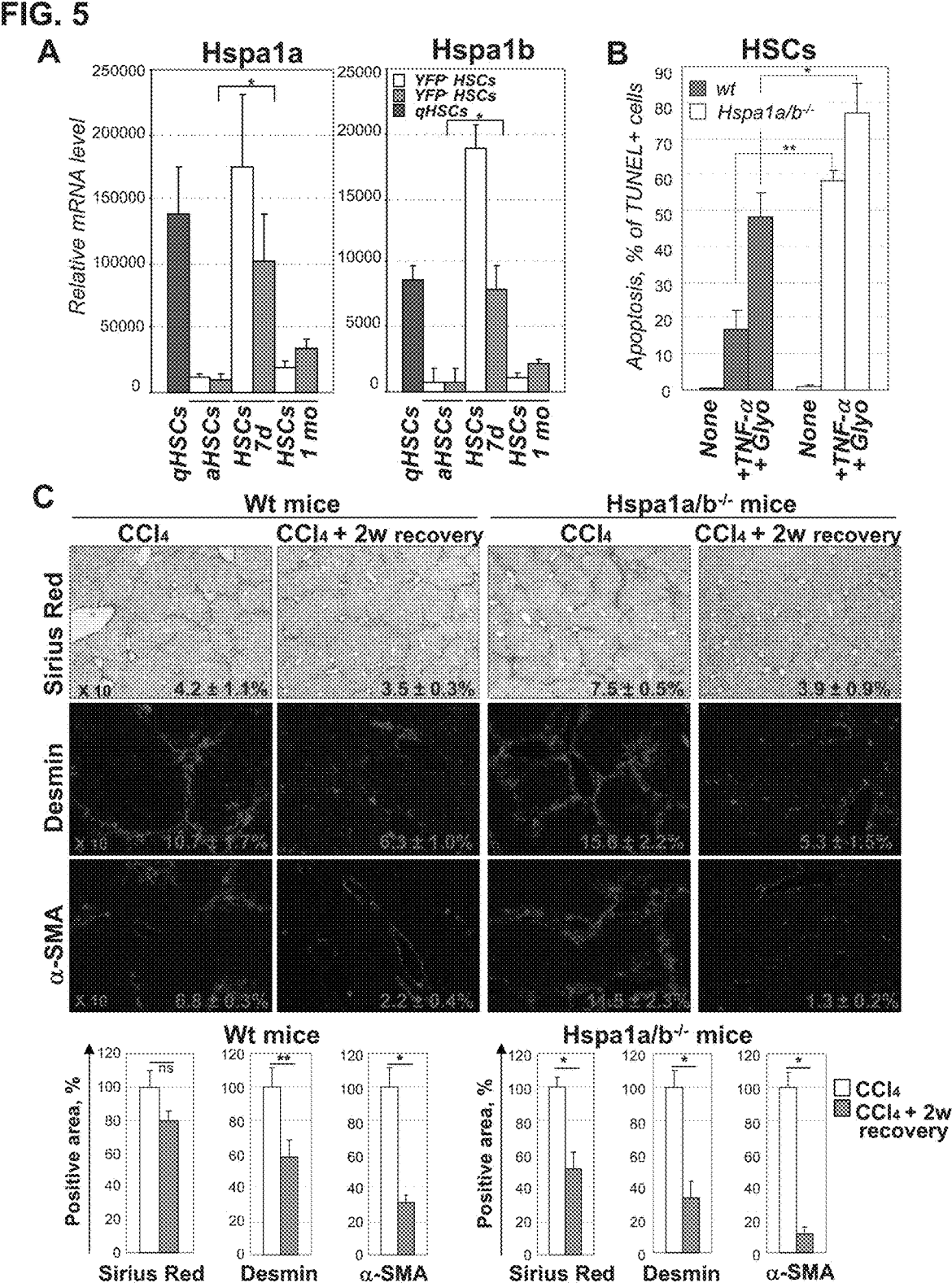
FIG. 5 shows genetically labeled YFP$^+$ HSCs upregulate pro-survival Hsp1a/b genes at 7 days of recovery. A. Upregulation of pro-survival Hsp1a/b genes in YFP$^+$ HSCs at 7 days of recovery. The results are expressed as relative mRNA levels (average of normalized values/multiple probes/gene, *p<0.001) obtained by Agilant microarray. B. Apoptosis was induced in Hspa1a/b$^{-/-}$ and wild type HSCs by glyotoxin (25 nM for 4 h) and TNF-$\alpha$(20 ng/ml)+ Actinomycin (0.2 µg/ml) for 18 h. Cell morphology (BF), Vitamin A and apoptitic cells (TUNEL$^+$ staining) are shown using ×10 objective. C. Hspa1a/b$^{-/-}$ and wt mice were gradually subjected to CCl$_4$-injury and recovered for 2 weeks, livers were analyzed by Sirius Red, staining for Desmin and $\alpha$-SMA (positive areas are indicated). Regression of fibrosis and disappearance of fibrogenic myofibroblasts during recovery were calculated in comparison with CCl$_4$-treatment (100%) and shown as percent of Sirius Red, Desmin and $\alpha$-SMA positive areas, *p, 0.01, **p<0.05.

Example 13—Activation of Hspa1a/b May Promote Survival of iHSCs at Day 7 of Recovery from Liver Fibrosis To understand how YFP$^+$ iHSCs escape apoptosis, we examined the signaling pathways in YFP$^+$ HSCs after 7 days recovery (FIG. 18B, 18E). In particular, expression of the anti-apoptotic Hspa1a/b genes was strongly but transiently induced these HSCs (FIG. 5A, FIG. 19A, to the levels comparable to qHSCs), but was dramatically downregulated in aHSCs and HSCs after 1 mo recovery (FIG. 5A, FIG. 19A).

We examined if Hspa1a/b would impact survival of cultured HSCs. For this purpose, HSCs were isolated from CCl$_4$-treated Hspa1a/b$^{-/-}$ and wild type mice (FIG. 19B), and cultured 5 days on plastic. Hspa1a/b$^{-/-}$ HSCs had a rounded shape and exhibited growth retardation (cell number ratio ko: wt—1:1.7, FIG. 19C). Moreover, Hspa1a/b$^{-/-}$ HSCs were more susceptible to glyotoxin-(13) and TNF-α-induced apoptosis (14) (FIG. 5B and FIG. 19C). Therefore, upregulation of Hspa1a/b genes may promote survival of iHSCs during recovery from fibrosis.

Example 14-Resolution of CCl$_4$-Induced Fibrosis is Expedited in Hspa1a/b$^{-/-}$ Mice It was hypothesized that the loss of survival signals in Hspa1a/b$^{-/-}$ HSCs would result in increased clearance of aHSCs after recovery from CCl$_4$-induced fibrosis. To test this, Hspa1a/b$^{-/-}$ and wild type mice were subjected to CCl$_4$-induced liver injury. As expected, Hspa1a/b$^{-/-}$ mice developed more severe fibrosis (probably due to increased hepatocyte death)(15) than the wild type littermates (FIG. 5C). However, after stopping CCl$_4$ treatment, regression of liver fibrosis was strongly accelerated in Hspa1a/b$^{-/-}$ mice compared to wild type mice (decreased 49% vs. 20% by Sirius red staining respectively). Hspa1a/b$^{-/-}$ livers also had a greater loss of α-SMA$^+$Desmin$^+$ aHSCs compared to wild type mice (decreased 68% vs. 40% of Desmin$^+$ positive area, respectively, FIG. 5C). Thus, Hspa1a/b is required so that iHSCs persist in the recovering liver.

Example 15—Expression of Mesothelin is Upregulated in PFs in Response to Injury

Expression level of selected genes was compared in aPF, aHSCs and other cell types in the liver, and confirmed specific upregulation of asporin, basonuclin 1, calcitonen-α, uroplakin 1β in aPFs (FIG. 20A-D). Hence, expression of mesothelin was detected only in isolated PF, and was clearly absent in aHSCs, KC, EC, and most closely correlated with the expression level of mesothelin in the whole liver. Expression of mesothelin was then examined in BDL- and CCl$_4$-induced liver tissues. Very few mesothelin$^+$ cells were identified in livers of CCl$_4$-treated mice. In contrast, mesothelin was widely expressed in livers of BDL-treated mice, and showed expression pattern similar to Thy1 and elastin. Moreover, expression of mesothelin was detected in fibrotic lesions in patients with secondary biliary fibrosis. These data indicate that mesothelin may serve as a marker of PFs.

Example 16-BDL and CCl$_4$ Liver Injury Activate Myofibroblasts

Figure 21:
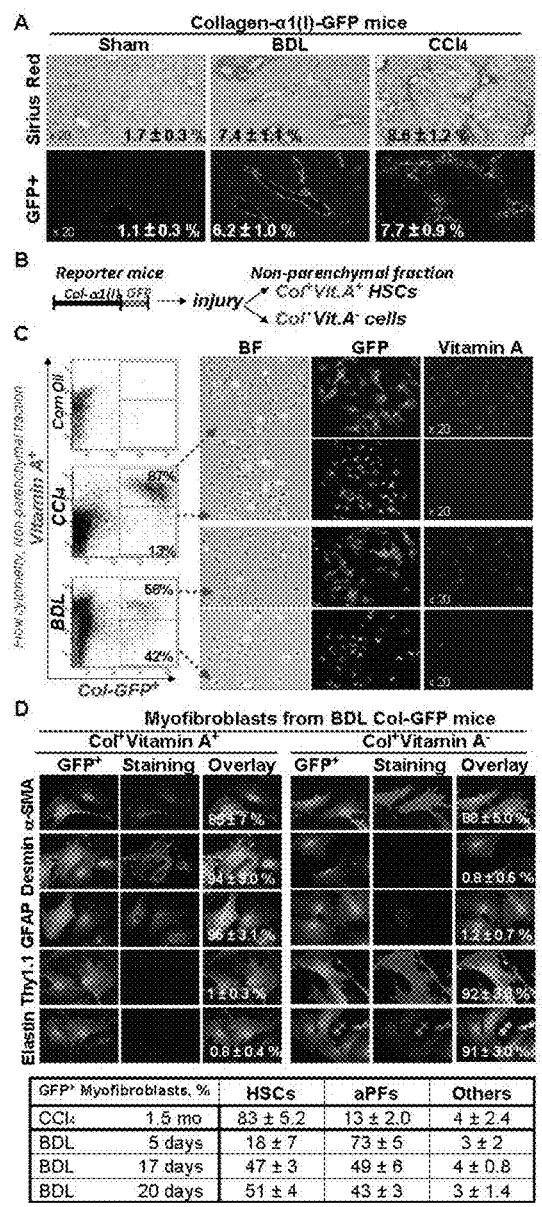
FIG. 21 Isolation of aPFs and aHSCs from BDL- and CCl$_4$-injured Col-GFP mice. A. CCl$_4$ (1.5 mo)- and BDL- (17 d) mice developed liver fibrosis. Sirius Red staining, fluorescent microscopy for collagen-GFP. B. Strategy to isolate aPFs by flow cytometry: Col-GFP+ myofibroblasts were identified by GFP, and fractionated to Vit.A+ and Vit.A− cells. C. FACS of non-parenchymal fraction from uninjured, BDL and CCl$_4$ Col-GFP mice: GFP+ and Vitamin A+ cells are shown, dot plots, $p<0.03$. GFP+Vit.A+ and GFP+Vit.A− cells are sort purified and analyzed by light and fluorescent microscopy for GFP and Vit.A (×20 objective). D. Immunophenotyping has identified GFP+Vit.A+ and GFP+Vit.A− cells as aHSCs and aPFs, respectively. For each fraction, the percent of stained cells is shown (compared to total cells, 100%). Immunocytochemistry-based quantification of GFP+ myofibroblasts (100%) in CCl$_4$ and BDL fibrosis, $p<0.05$ FIG. 22 Characterization of aPFs. A. A Global Gene expression profile of BDL (17 d)-activated GFP+Vit.A− aPFs was compared to BDL- and CCl$_4$-activated GFP+ Vit.A+ aHSCs. B. Expression level of Col1a1 mRNA in BDL-(5 d)-aPFs is comparable to that in CCl$_4$-aHSCs, but is much higher than in BDL-aHSCs, $p<0.01$. C. Response to cytokines was compared in BDL-aPFs and CCl$_4$-aHSCs. Both aHSCs and aPFs responded to TGF-β1 (5 ng/ml). D. Upper panel, BDL-aPFs (but not BDL-aHSCs or CCl$_4$-aHSCs) responded to TCA (1200 nmol/ml) by upregulation of Col1a1; and to IL-25 (100 ng/ml) by upregulation of IL-13, $p<0.05$. Lower panel, IL-13 (100 ng/ml)-stimulated qHSCs by inducing CTCF, Col1a1, a-SMA mRNA $*p<0.01$, $**p<0.02$. E. Expression of signature genes was determined for BDL-aPFs. Previously identified PF-specific genes (red). Fold induction (compared to the highest value observed in BDL or CCl$_4$-activated HSCs) is shown. F. Expression of Msln was compared by qPCR in aPFs and other cells, $p<0.05$. G. aPFs and aHSCs were isolated from BDL (17 d) Col-GFP mice. Expression of Msln was detected only in aPFs (but not in GFAP+ aHSCs) and co-localized with Elastin (TE-7) and Thy-1 staining, $p<0.05$. H. Livers from BDL- or CCl$_4$-injured mice (n=10/group). Expression of Msln was detected in BDL-mice, but not in sham-mice. Only a few Msln+ cells were detected in CCl$_4$-mice, $p<0.003$.

Col-GFP mice23 were subjected to BDL (17 d) or CCl$_4$ (1.5 mo, FIG. 21A). All hepatic myofibroblasts in these mice were visualized by GFP expression 23, 34, 35, 57. Development of liver fibrosis was confirmed by Sirius Red staining, and correlated with increased Col1a1 (fold increase 6.1±0.3 and 7.6±0.4 in BDL, CCl$_4$ vs sham mice).

Isolation of aPFs and iHSCs by Cell Sorting.

Our strategy to determine the composition of hepatic myofibroblasts in BDL- and CCl$_4$-injured Col-GFP mice was based on fractionation of aHSCs (GFP$^+$VitaminA$^+$) and myofibroblasts of other origin (GFP$^+$VitaminA$^-$, FIG. 21B-C) from the non-parenchymal cell faction containing GFP$^+$ myofibroblatsts (57). While collagen-α1(I)-GFP is expressed in all activated myofibroblasts, only HSCs contain Vitamin A (Vit.A) droplets (1, 57). Although HSCs downregulate Vitamin A upon activation (aHSCs), expression of Vitamin A is still detected in in vivo aHSCs by flow cytometry and fluorescent microscopy (57, 58) FIG. 21C). As quantified by flow cytometry, activated myofibroblasts (GFP$^+$ cells, 100%) were detected only in injured mice. CCl$_4$-activated myofibroblasts contained 87±6% GFP+ Vit.A$^+$ and 13±3% GFP$^+$Vit.A$^-$ cells, while BDL (17 d)-activated myofibroblasts consisted of 56±4% GFP+Vit.A$^+$ and 42±5% GFP+Vit.A$^-$ cells, demonstrating that the composition of myofibroblasts varies depending on the etiology of liver injury. GFP$^+$Vit.A$^+$ and GFP$^+$Vit.A$^-$ cells were sort purified, plated, and expression of GFP±Vit.A was confirmed by fluorescent microscopy (FIG. 21C). Immunophenotyping (FIG. 21D) revealed that all GFP cells expressed the myofibroblast marker αSMA. BDL-activated GFP$^+$Vit.A$^+$ myofibroblasts were identified as Desmin$^+$ GFAP$^+$ aHSCs, while GFP$^+$Vit.A myofibroblasts were stained positive for the established aPF markers Thy-1 (93±4.0%) and elastin (86±3.4%), but lacked markers of HSCs (GFAP, Desmin, CD146) and of myeloid cells (CD11b, F4/80, CD68). Only a small number of GFP$^+$Vit.A$^-$ cells expressed fibrocyte-like markers CD45 (3.1±0.1%, FIG. 21D). (Similar results were obtained when the non-parenchymal fraction was sorted for GFP$^+$NGFR$^+$ and GFP$^+$ Thy-1$^+$ cells, which identified as Vit.A$^+$ aHSCs and Vit.A$^-$ aPFs, respectively, data not shown).

Example 17—Gene Expression Profiling of aPFs Versus CCl$_4$-aHSCs and BDL-aHSCs

Figure 22:
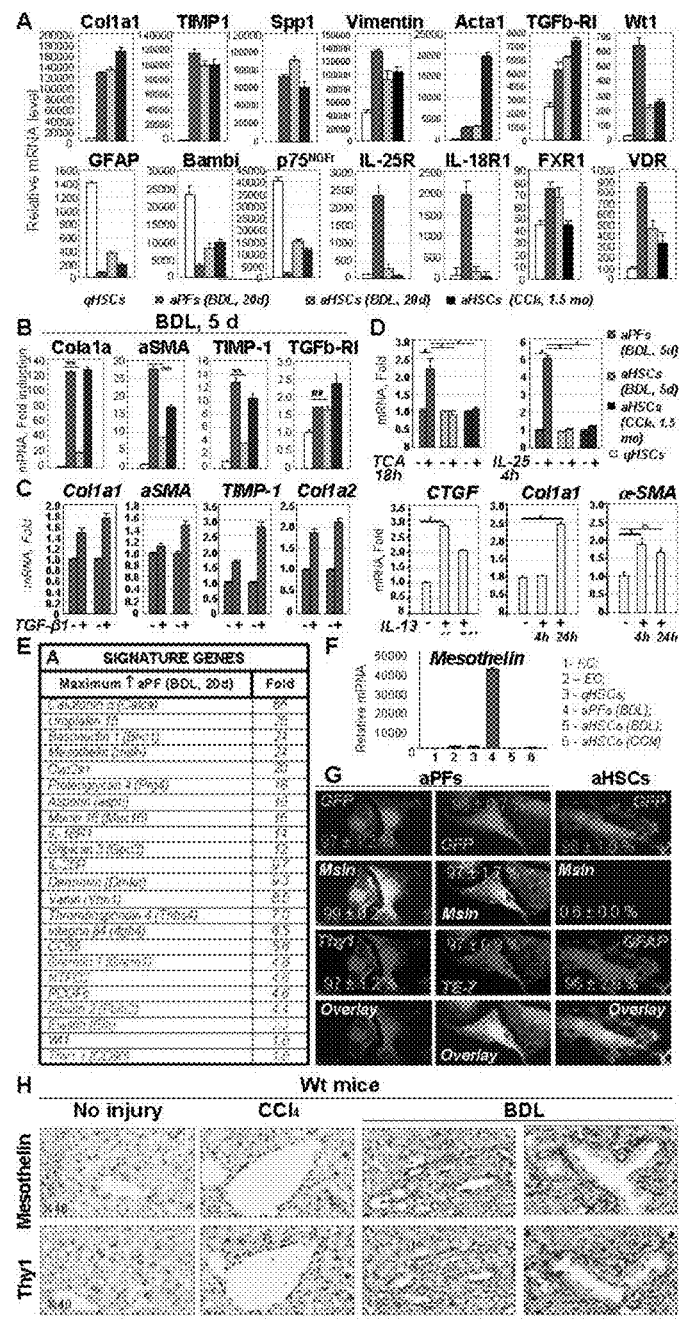

The gene expression profile of BDL (17 days)-activated aPFs was compared to BDL (17 days)-activated aHSCs and CCl$_4$ (1.5 mo)-activated aHSCs (FIG. 22A). Using a threshold defining confident detection of gene expression, we confirmed that aPFs exhibited a myofibroblast phenotype, sharing mRNA expression of 8981 genes with aHSCs. These genes included Colla(1), Col1a2, Col2a1, TIMP-1, Sppl, TGF/J-RI, and Vimentin, that were induced in aPFs to a level comparable to BDL- and CCl$_4$-activated aHSCs. As expected, GFAP and Bambi mRNAs were highly expressed in qHSCs. aPFs had an additional 694 unique genes (see below).

Functional Properties of BDL-Derived aPFs Differ from aHSCs.

Our data indicate that aPFs and aHSCs exhibit similar levels of activation in response to BDL (17 d, FIG. 22A). To further characterize the fibrogenic properties of aPFs, earlier time points of BDL were examined. After 5 days of BDL (FIG. 22B), expression levels of Col1a1, αSMA, and TIMP1 mRNA were much higher in aPFs than in aHSCs, suggesting that the activation of PFs precedes the activation of HSCs in BDL injury. For example, Col1a1 was 120-fold induced in aPFs over the level in qHSCs, compared to 20-fold induction in aHSCs. Next, we assessed how aPFs and aHSCs responded to fibrogenic stimuli in vitro. As expected, the fibrogenic cytokine TGF-β1 had similar effects on aPF and aHSC (FIG. 22C). However, only aPFs responded to the bile acid TCA, with increased Col1a1 mRNA expression (↑2.2 fold induction over control aPFs), suggesting that TCA may directly mediate PF activation (FIG. 22D). Furthermore, only aPFs responded to IL-25 stimulation by induction of IL-13 (similar to IL-13 induction by IL-25-treated macrophages (82) and fibroblasts (83)). IL-13 stimulated activation of HSCs in vitro (FIG. 22D) (84, 85) by inducing CTCF mRNA (after 4 h) and Col1a1, αSMA, and TIMP1 mRNA (24 h) in aHSCs, suggesting that aPFs facilitate HSC activation.

Unique Genes that Distinguish aPFs from aHSCs.

Based on the Whole mouse genome microarray, aPFs expressed genes that distinguish them from BDL- or $CCl_4$-activated aHSCs which we identified as "signature genes" for aPFs (FIG. 22E). In concordance with previous studies (74, 86), we confirmed that aPFs express Thy-1, elastin, Gremlin 1, Fibulin 2, and NTPD2 (these markers were reported to discriminate between aPFs and aHSCs) (64, 87). In addition, we identified that aPFs uniquely expressed calcitonin α (fold induction ↑48 over the highest value in BDL-aHSCs or $CCl_4$-aHSCs), mesothelin (↑28), uroplakin 1β (↑22), basonuclin 1 (↑18), asporin (↑14), proteoglycan 4 (↑14), and CD200 (↑11). Some of these genes (including basonuclin 1, glycoprotein m6a, uroplakin 3b and 1b, mesothelin, IL-18R, and calcitonin) were reported as signature genes of murine hepatic mesothelial (88) and epicardial cells (89), supporting the theory that PFs originate from mesothelial cells (90, 19). Expression of mesothelin, in Thy-1$^+$ aPFs but not in qHSCs, aHSCs, endothelial cells (EC), Kupffer cells (KC), or cholangiocytes was confirmed by qPCR (FIG. 22F), immunocytochemistry of isolated aPFs and aHSCs (FIG. 22G), and immunofluorescence of BDL- (vs $CCl_4$)-injured wt mice (FIG. 22H). Since expression of mesothelin was detected only in isolated aPFs but not in other cellular fractions, suggesting that Msln expression is restricted to aPFs, we further studied the role of Msln in liver fibrosis.

Mesothelin Knockout Mice are Resistant to Cholestatic, but not Hepatotoxic, Liver Fibrosis.

Figure 23:
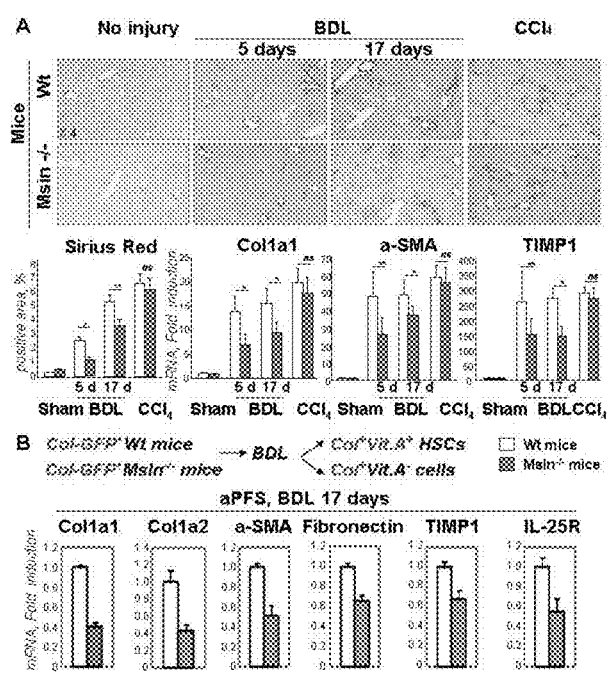
FIG. 23. Msln$^{-/-}$ mice are protected from BDL- (but not CCl$_4$)-induced fibrosis. A. Msln$^{-/-}$ and wt mice (n=10 per group) were subjected to BDL (5 d, 17 d) or CCl$_4$ (1.5 mo). Livers were analyzed by Sirius Red, and quantified. Expression of fibrogenic genes was analyzed by qPCR, and the data is fold induction compared with sham-operated mice, $*p<0.01$, $**p<0.05$, B. Msln$^{-/-}$ Col-GFP mice and Col-GFP mice were subjected to BDL (17 d). aPFs were isolated from Msln$^{-/-}$Col-GFP and Col-GFP mice and analyzed by qPCR. Msln$^{-/-}$ aPFs exhibited a defect in activation compared to wt aPFs, p<0.01.

To test if mesothelin plays a role in PF activation into myofibroblasts, Msln$^{-/-}$ mice were subjected to BDL- and $CCl_4$-injury, and development of liver fibrosis was compared to wt mice (FIG. 23A). No difference in liver fibrosis was observed in $CCl_4$-injured Msln$^{-/-}$ and wt mice, confirming that Msln aHSCs, but not Msln$^+$ aPFs, are critical for liver hepatotoxic liver fibrosis (FIG. 23A). In contrast, development of BDL (5 days)-induced liver fibrosis was attenuated in Msln$^{-/-}$ mice compared to wt mice, as demonstrated by reduced (↓2 fold) area of Sirius Red staining and downregulation of fibrogenic gene expression (↓2 fold Col1a1, ↓1.7 fold α-SMA, ↓1.7 fold TIMP1, but not TGFβ-RI). Inhibition of liver fibrosis was also observed in Msln$^{-/-}$ mice at 17 days after BDL, as determined by reduced staining for Sirius Red ↓ (1.5 fold) and decreased expression of Col1a1 (↓1.6 fold), αSMA (↓1.4 fold), TIMP1 (↓1.7 fold) mRNA in Msln$^-$ deficient PFs (versus wt PFs, FIG. 23A-B). These data correlate with our findings that activation of PFs is critical at the onset of BDL, while activation of HSCs correlates with the progression of cholestatic liver fibrosis.

Example 18—Msln$^{-/-}$ aPFs Exhibit a Defect in Activation, Migration and Proliferation Primary aPFs were isolated from BDL (5 d) wt and Msln$^{-/-}$ mice and analyzed by qPCR and RNA-Seq (data not shown). We determined that the clusters of genes responsible for fibrogenesis and ECM production, proliferation, and adhesion were downregulated in Msln$^{-/-}$ aPFs, while expression of VDR, IL-25R, and IL-18R were not affected by mesothelin deficiency. To further investigate mesothelin function and signaling, we generated immortalized wt and Msln$^{-/-}$ aPF cell lines by introducing SV40 large T antigen (via lentiviral infection) as previously described (91). Similar to primary aPFs, TGB-β1-stimulated immortalized Msln$^{-/-}$ aPFs exhibited a defect in induction of Col1a1, αSMA, PAI-1, and activin mRNA (FIG. 24A). This effect was associated with low levels of Smad2/3 phosphorylation (compared to wt aPFs, FIG. 24B), and surprisingly, with upregulation of Thy-1 (↑150 fold), mucin 16 (Muc16, ↑2.5) and Smad7 (↑2). Previous studies implicated Thy-1 and Smad7 in suppression of TGF-β1 responses, while the role of Muc16 in fibroblast function has not been investigated. To explore the relationship between Msln (78, 92) Thy-1 (92, 93) Smad7 (95) and Muc16 (96, 97), a series of immunoprecipitations (IP) was performed using immortalized wt and Msln aPFs (FIG. 24C). IP with anti-TGFβRI Ab revealed that Thy-1 proteins (detected by anti-Thy-1 Ab). IP with anti-Msln Ab revealed that Thy-1 also binds to Msln, suggesting that Msln and Thy-1 may form a complex with TGFβRI in response to TGF-β1. In addition, FGF-2-stimulated Msln$^{-/-}$ aPFs failed to upregulate Cyclin D, c-Myc, or integrin 136 genes (FIG. 24D), and Msln$^{-/-}$ aPFs demonstrated reduced proliferation and migration in response to a "scratch assay" (FIG. 24E). Based on the data presented herein and without wishing to be bound by any particular theory, we hypothesize that 1) similar to Endoglin (CD105), Msln may act as a TGF-β1 co-receptor, 2) similar to Bambi, Msln may serve as an inhibitor of Thy-1; and 3) Mesothelin might regulate integrin(s)/Muc16-depended migration of aPFs.

Figure 25:
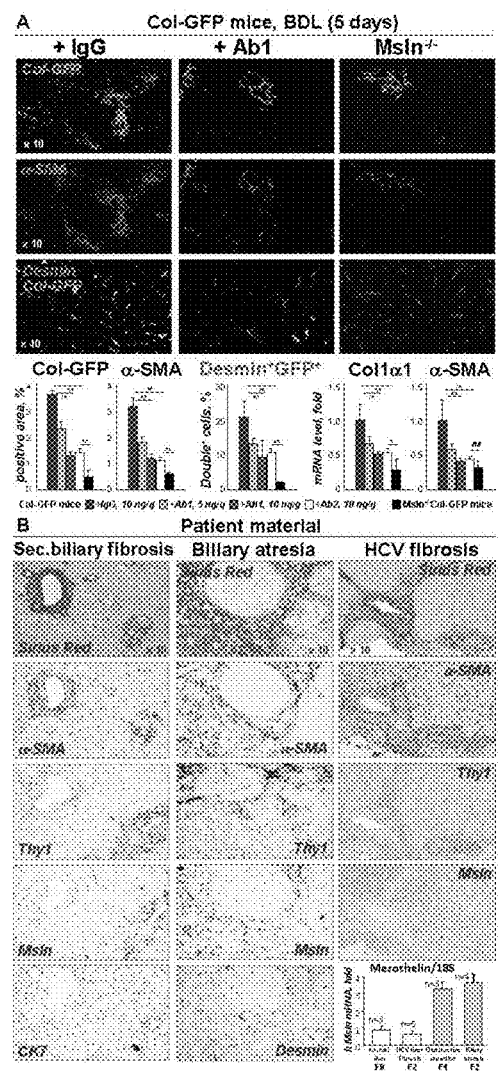
FIG. 25. Mesothelin as target for anti-fibrotic therapy. A. Msln-blocking Ab attenuates liver fibrosis in BDL-operated Col-GFP mice (n=6/group) compared to IgG-treated mice. B. Immunostaining of human liver shows upregulation of Thy-1$^+$ aPFs in patients with secondary biliary fibrosis, and biliary atresia, but not in patients with HCV fibrosis. Msln expression overlapped with Thy-1 and α-SMA staining in patients with biliary fibrosis. aHSCs were stained for Desmin, bile ducts were stained for cytokeratin 7 (CK7). Liver fibrosis stage was evaluated by Metavir Score. Sirius Red and H&E are shown using ×10 objective.

Example 19-Blocking of Msln Expression in aPFs May Attenuate Cholestatic Liver Fibrosis Hepatic fibroblasts have been suggested to originate from Msln+progenitors in response to injury (98). The loss of Msln expression in aPFs results in their reduced proliferation and activation. Here we test if treatment of BDL-injured mice with Msln-blocking Abs can inhibit activation of hepatic myofibroblasts and reduce fibrosis. For this purpose, Col-GFP mice were i.v. injected with anti-Msln Ab D233-3 (5 ng, 10 ng, MBL Inc.) or B35 Ab (10 ng, LSBio) at day 1 and day 3 post BDL, and sacrificed at day 5 post BDL (FIG. 25A). Significant inhibition of liver fibrosis (approximately 60%) was observed in mice treated with anti-Msln Abs (versus isotype-matched Ab-treated mice, 100%), and was associated with reduced activation of GFP+ myofibroblasts in a dose-dependent manner. These data indicate that Msln is an anti-fibrotic target.

Example 20-Thy-1$^+$ and Msln$^+$ aPFs were Detected Only in Livers of Patients with Cholestatic Liver Injury The composition of myofibroblasts was analyzed by immunohistochemistry in livers resected from patients with cholestatic (biliary atresia, n=4, secondary biliary cirrhosis, n=3), and HCV liver fibrosis (n=5). Thy-1$^+$ and Msln$^+$ aPFs were detected in fibrotic lesions of patients with biliary atresia and secondary biliary cirrhosis, but not HCV-fibrosis (FIG. 25B), signifying that aPFs play a role in the pathogenesis of cholestatic injury. Expression of Msln overlapped with Thy-1$^+$α-SMA$^+$ (but not CK7$^+$ or desmin$^+$) areas, suggesting that Msln may serve as a new marker of human aPFs.

Discussion of Results

Clinical and experimental hepatic fibrosis regresses dramatically with removal of the underlying etiological agent. Myofibroblasts are αSMA$^+$ Collagen Type I$^+$ cells that are absent from the normal uninjured liver, rapidly emerge in fibrotic liver to produce the fibrous scar, and completely disappear with regression of liver fibrosis (1, 2). In hepatotoxic-induced liver fibrosis (such as CCl$_4$ or intragastric alcohol feeding), quiescent hepatic stellate cells (GFAP$^+$Desmin$^+$SMA$^-$Col$^-$ qHSCs) undergo activation to become the major source of myofibroblasts (GFAP$^+$Desmin$^+$αSMA$^+$Col$^+$ aHSCs). The above results demonstrate the use of genetic markers to address the composition of fibrogenic myofibroblasts. The fate (determined using irreversible genetic labeling using Cre-lox system) of these aHSCs/myofibroblasts during regression of liver fibrosis is determined using transgenic mice specifically generated for this study, Collagen-Cre mice. The data demonstrate that aHSCs/myofibroblasts are cleared by two mechanisms: 1) As previously reported, some myofibroblasts undergo cell death by apoptosis (2); and 2) Some myofibroblasts revert to a previously unrecognized inactive phenotype (iHSCs) that is similar to, but distinct from, quiescent HSCs.

Reversal of fibrosis is associated with increased collagenase activity, activation of macrophages/Kupffer cells secreting matrix metalloproteinases, and matrix degradation (1). Senescence and apoptosis of activated HSCs plays a significant role in resolution of liver fibrosis by eliminating the cell type responsible for producing the fibrotic scar (2, 3). Here. the data demonstrate that some aHSCs undergo apoptosis, while other aHSCs escapes apoptosis, lose expression of fibrogenic genes, and persist in the liver in an inactivated phenotype. This phenomenon was demonstrated using two models of liver fibrosis with different etiologies: CCl$_4$ and alcohol-induced liver injury. These data suggest that inactivation of aHSCs/myofibroblasts is a common feature of regression of liver fibrosis.

Studies in culture suggest that aHSCs can revert to a quiescent phenotype, associated with expression of lipogenic genes (Adfp, Adipor1, CREBP, PPAR-γ)(5) and storage of vitamin A in lipid droplets. Depletion of peroxisome proliferator-activated receptor gamma (PPAR-γ) constitutes a key molecular event for HSC activation, and ectopic over-expression of this nuclear receptor results in the phenotypic reversal of activated HSC to quiescent cells in culture (5). The treatment of activated HSCs with an adipocyte differentiation cocktail, over-expression of SREBP-1c, or culturing on basement membrane-like ECM (16) results in up-regulation of adipogenic transcription factors and causes morphologic and biochemical reversal of activated HSCs to quiescent cells (17). Applicants in vivo cell fate mapping studies demonstrate that iHSCs survive apoptosis during reversal of liver fibrosis with a new phenotype that is similar to, but distinct from, the original qHSCs.

The data presented herein confirms that HSCs transiently express collagen Type I during development (E16.5-P14), but do not spontaneously become myofibroblasts. This observation explains the presence of genetically labeled qHSCs with a history of collagen expression in livers of uninjured adult mice. These genetically labeled qHSCs possess a quiescent phenotype, indistinguishable from qHSCs with no history of collagen expression. In addition, transient activation of HSCs is required for liver regeneration following partial hepatectomy (I8), but the subsequent fate of these HSCs is currently unknown. In turn, after month of regression from CCl$_4$-induced liver fibrosis, aHSCs/myofibroblasts do not fully revert to a quiescent phenotype. iHSCs downregulate the fibrogenic genes Collagen-(α1(I)), Collagen-α1(2), α-SMA, TGF RI and TIMPI, upregulate some quiescence associated genes (PPARγ and Bambi) to levels comparable to qHSCs, but did not reacquire high expression of GFAP, Adfp and Adipor1 (5). These genetically labeled iHSCs constituted approximately 50% of total HSCs in the liver 1 mo after reversal of liver fibrosis. Interestingly, the remaining HSCs have no history of activation, highly resemble qHSCs phenotypically, and represent new qHSCs generated from residual ypp-qHSCs or from a precursor cell population. Although during development HSCs originate from submesothelial mesenchymal cells (I9), the source of HSC replenishment is unknown. Using bone marrow chimeric mice, several studies have indicated that HSCs originate from endogenous liver cells and not from a bone marrow derived progenitor cell (8).

Unlike aHSCs, iHSCs completely downregulate expression of fibrogenic genes, but in response to TGFβ1, more rapidly activate into myofibroblasts than qHSCs. Consistent with the concept of iHSCs being more fibrogenic than qHSCs, a previously injured and recovered liver develops more fibrosis than a naïve liver. Applicants directly tested this concept in vivo by adoptive transfer of HSCs into livers of immunodeficient Rag2$^{-/-}$γc$^{-/-}$ mice. Unlike previous ectopic transfer experiments (20, 21), HSCs (1 mo. recovery) were transplanted into their natural liver environment, and their response to CCl$_4$-injury was monitored. Here, Applicants demonstrated that iHSCs activate and fully integrate into the fibrous scar in recipient mice more efficiently than qHSCs. Thus, in culture and in vivo iHSCs are activated more effectively than naïve qHSCs, so that the previously injured liver generates more fibrous scar in response to a repeated injury.

It is not clear why some aHSCs escape apoptosis and inactivate, while other HSCs die after cessation of the injury. Applicants' data suggest that survival of iHSCs requires the upregulation of pro-survival signals, such as induction of heat shock proteins (22). Two members of Hsp70 family of heat shock proteins, Hspa1a and Hspa1b (22), that play a protective role against stress-induced apoptosis (23), were strongly and transiently upregulated in HSCs after 7 days of reversal of fibrosis (when apoptosis of other aHSCs is highest) compared with the aHSCs in fibrotic liver. Furthermore, Applicants demonstrated that genetic ablation of Hspa1a/b renders aHSCs more susceptible to TNF-α(14) and glyotoxin-induced (24) apoptosis in culture. In concordance, regression of liver fibrosis was strongly accelerated in Hspa1a/b$^{-/-}$ mice, and was associated with increased disappearance of α-SMA$^+$Desmin$^+$ HSCs. These data suggest that Hspa1a/b regulate HSC survival, while PPAR-γ drives HSC inactivation during reversal from liver fibrosis.

The data disclosed herein show that hepatotoxic (CCl$_4$) and cholestatic (BDL) liver injuries activate distinct subsets of fibrogenic myofibroblasts. Thus, CCl$_4$ activates preferentially aHSCs, while BDL initially preferentially activates portal fibroblasts (aPFs). We developed a reliable method of isolation and quantification of hepatic myofibroblast fractions using flow cytometry. Based on the distinctive expression of Vitamin A and GFAP in HSCs and Thy1 and elastin in PFs, this study establishes cell sorting as a robust method to purify distinct populations of myofibroblasts in mice. The data herein provide additional proof that Vitamin A is a reliable marker for identification, quantification and purification of aHSCs, making flow cytometry using Vitamin A autofluorescence as the method of choice to purify aHSCs from myofibroblasts of other origins. Flow cytometry enables identification of hepatic myofibroblasts and isolation of distinct subsets of myofibroblasts (HSCs and PFs) with high purity from the same mouse liver.

In contrast to $CCl_4$-induced injury, the data herein demonstrate that PFs rapidly activate at the onset of cholestatic injury and upregulate fibrogenic genes. Furthermore, early activation of PFs during BDL injury may affect HSCs, and BDL-activated HSCs exhibit more similarity to aPFs than to $CCl_4$-activated HSCs. Gene expression profiling demonstrated novel signature genes for aPFs. According to cell fate mapping, PFs originate from the mesothelium (19, 81), and our data suggest that aPFs share similarity in signature gene expression with other cells of mesothelial origin. One of these genes, mesothelin, is highly induced specifically in aPFs in response to BDL injury.

As shown herein mesothelin (Msln)-deficient mice are less susceptible to liver fibrosis compared to the wild type mice. Previous studies have implicated mesothelin in mediation of cellular interaction and metastatic dissemination. Due to strong induction in different types of cancer, mesothelin is considered as a tumor-associated antigen, which serves as a prognostic marker of disease progression, and became a therapeutic target for anti-cancer therapy. Here we demonstrate that mesothelin is highly expressed in aPFs in response to BDL, so that mesothelin may serve as a novel marker of activated PFs and a target for antifibrotic therapy.

Characterization of New Markers of aPFs.

In an attempt to distinguish aPFs from aHSCs and other myofibroblasts, the "signature genes" characteristic for aPFs were identified. The data herein confirms that expression of Thy1 and Elastin distinguishes Vitamin A$^-$GFAP$^-$Desmin$^-$CD146$^-$ aPFs from Vitamin A$^+$GFAP$^+$Desmin$^+$CD146$^+$ Thy1$^-$Elastin$^-$ aHSCs. Using gene expression profiling of in vivo activated HSCs and PFs, we have identified that calcitonin α, mesothelin, uroplakin 1β, basonuclin 1, asporin, glipican 3, CD200, IL-18R1, and IL-25R may serve as additional useful markers to distinguish aPFs from aHSCs and myofibroblasts of other origins. We determined that these genes are highly expressed in portal fibroblasts but not in other cell types in fibrotic liver.

EQUIVALENTS

Those skilled in the art will recognize, or be able to ascertain using no more than routine experimentation, many equivalents to the specific embodiments of the invention described herein. Such equivalents are intended to be encompassed by the following claims.

LITERATURE CITED

1. Bataller R & Brenner D A (2005) Liver fibrosis. *J Clin Invest* 115(2):209-218.
2. Iredale J P, et al. (1998) Mechanisms of spontaneous resolution of rat liver fibrosis. Hepatic stellate cell apoptosis and reduced hepatic expression of metalloproteinase inhibitors. *J Clin Invest* 102(3):538-549.
3. Krizhanovsky V, et al. (2008) Senescence of activated stellate cells limits liver fibrosis. *Cell* 134(4):657-667.
4. Friedman S L, Roll F J, Boyles J, & Bissell D M (1985) Hepatic lipocytes: the principal collagen-producing cells of normal rat liver. *Proc Natl Acad Sci USA* 82(24):8681-8685.
5. She H, Xiong S, Hazra S, & Tsukamoto H (2005) Adipogenic transcriptional regulation of hepatic stellate cells. *J Biol Chem* 280(6):4959-4967.
6. Lee C G, et al. (2004) Early growth response gene 1-mediated apoptosis is essential for transforming growth factor beta1-induced pulmonary fibrosis. *J Exp Med* 200(3):377-389.
7. Huby A C, et al. (2009) Restoration of podocyte structure and improvement of chronic renal disease in transgenic mice overexpressing renin. *PLoS One* 4(8):e6721.
8. Seki E, et al. (2007) TLR4 enhances TGF-beta signaling and hepatic fibrosis. *Nat Med* 13(11):1324-1332.
9. Lee K S, Buck M, Houglum K, & Chojkier M (1995) Activation of hepatic stellate cells by TGF alpha and collagen type I is mediated by oxidative stress through c-myb expression. *J Clin Invest* 96(5):2461-2468.
10. Stefanovic B & Brenner D A (2003) 5' stem-loop of collagen alpha 1(I) mRNA inhibits translation in vitro but is required for triple helical collagen synthesis in vivo. *J Biol Chem* 278(2):927-933.
11. Goldman J P, et al. (1998) Enhanced human cell engraftment in mice deficient in RAG2 and the common cytokine receptor gamma chain. *British journal of haematology* 103(2):335-342.
12. Hawley T S, Herbert D J, Eaker S S, & Hawley R G (2004) Multiparameter flow cytometry of fluorescent protein reporters. *Methods Mol Biol* 263:219-238.
13. Wright M C, et al. (2001) Gliotoxin Stimulates the Apoptosis of Human and Rat Hepatic Stellate Cells and Enhances the Resolution of Liver Fibrosis in Rats. *Gastroenterology* 121(3):685-698.
14. Siegmund S V, et al. (2007) The endocannabinoid 2-arachidonoyl glycerol induces death of hepatic stellate cells via mitochondrial reactive oxygen species. *FASEB J* 21(11):2798-2806.
15. Ikeyama S, Kusumoto K, Miyake H, Rokutan K, & Tashiro S (2001) A non-toxic heat shock protein 70 inducer, geranylgeranylacetone, suppresses apoptosis of cultured rat hepatocytes caused by hydrogen peroxide and ethanol. *J Hepatol* 35(1):53-61.
16. Wells R G (2008) The role of matrix stiffness in regulating cell behavior. *Hepatology* 47(4):1394-1400.
17. Tsukamoto H (2005) Adipogenic phenotype of hepatic stellate cells. *Alcohol Clin Exp Res* 29(11 Suppl):132S-133S.
18. Kalinichenko V V, et al. (2003) Foxf1+/−mice exhibit defective stellate cell activation and abnormal liver regeneration following CCl4 injury. *Hepatology* 37(1):107-117.
19. Asahina K, et al. (2009) Mesenchymal origin of hepatic stellate cells, submesothelial cells, and perivascular mesenchymal cells during mouse liver development. *Hepatology* 49(3):998-1011.
20. Yin Z, Wu W, Fung J J, Lu L, & Qian S (2007) Cotransplanted hepatic stellate cells enhance vascularization of islet allografts. *Microsurgery* 27(4):324-327.
21. Winau F, et al. (2007) Ito cells are liver-resident antigen-presenting cells for activating T cell responses. *Immunity* 26(1):117-129.

22. Yenari M A, et al. (2005) Antiapoptotic and anti-inflammatory mechanisms of heat-shock protein protection. *Ann NY Acad Sci* 1053:74-83.
23. Gabai V L, et al. (2000) Hsp72-mediated suppression of c-Jun N-terminal kinase is implicated in development of tolerance to caspase-independent cell death. *Mol Cell Biol* 20(18):6826-6836.
24. Wright M C, et al. (2001) Gliotoxin stimulates the apoptosis of human and rat hepatic stellate cells and enhances the resolution of liver fibrosis in rats. *Gastroenterology* 121(3):685-698.
25. Yata Y, et al. (2003) DNase I-hypersensitive sites enhance alpha1(I) collagen gene expression in hepatic stellate cells. *Hepatology* 37(2):267-276.
26. Florin L, et al. (2004) Cre recombinase-mediated gene targeting of mesenchymal cells. *Genesis* 38(3):139-144.
27. Tsukamoto H, Mkrtchyan H, & Dynnyk A (2008) Intragastric ethanol infusion model in rodents. *Methods Mol Biol* 447:33-48.
28. Xiong S, et al. (2008) Hepatic macrophage iron aggravates experimental alcoholic steatohepatitis. *Am J Physiol Gastrointest Liver Physiol* 295(3):G512-521.
29. Yan A W, et al. (Enteric dysbiosis associated with a mouse model of alcoholic liver disease. *Hepatology.*
30. de Hoon M J, Imoto S, Nolan J, & Miyano S (2004) Open source clustering software. *Bioinformatics* 20(9):1453-1454.
31. Saldanha A J (2004) Java Treeview—extensible visualization of microarray data. *Bioinformatics* 20(17):3246-3248.
32. Dennis G, Jr., et al. (2003) DAVID: Database for Annotation, Visualization, and Integrated Discovery. *Genome Biol* 4(5):P3.
33. Eyden B. The myofibroblast: phenotypic characterization as a prerequisite to understanding its functions in translational medicine. J Cell Mol Med 2008; 12:22-37.
34. Majno G, Gabbiani G, Hirschel B J, et al. Contraction of granulation tissue in vitro: similarity to smooth muscle. Science 1971; 173:548-50.
35. Gabbiani G, Ryan G B, Majne G. Presence of modified fibroblasts in granulation tissue and their possible role in wound contraction. Experientia 1971; 27:549-50.
36. Schurch W, Seemayer T A, Gabbiani G. The myofibroblast: a quarter century after its discovery. Am J Surg Pathol 1998; 22:141-7.
37. Kisseleva T, Brenner D A. Mechanisms of fibrogenesis. Exp Biol Med (Maywood) 2008; 233:109-22.
38. Parola M, Marra F, Pinzani M. Myofibroblast—like cells and liver fibrogenesis: Emerging concepts in a rapidly moving scenario. Mol Aspects Med 2008; 29:58-66.
39. Iredale J P. Models of liver fibrosis: exploring the dynamic nature of inflammation and repair in a solid organ. J Clin Invest 2007; 117:539-48.
40. Geerts A. History, heterogeneity, developmental biology, and functions of quiescent hepatic stellate cells. Semin Liver Dis 2001; 21:311-35.
41. Sachs B D, Baillie G S, McCall J R, et al. p75 neurotrophin receptor regulates tissue fibrosis through inhibition of plasminogen activation via a PDE4/cAMP/PKA pathway. J Cell Biol 2007; 177:1119-32.
42. Kendall T J, Hennedige S, Aucott R L, et al. p75 Neurotrophin receptor signaling regulates hepatic myofibroblast proliferation and apoptosis in recovery from rodent liver fibrosis. Hepatology 2009; 49:901-10.
43. Senoo H, Kojima N, Sato M. Vitamin a-storing cells (stellate cells). Vitam Horm 2007; 75:131-59.
44. Bataller R, Schwabe R F, Choi Y H, et al. NADPH oxidase signal transduces angiotensin II in hepatic stellate cells and is critical in hepatic fibrosis. J Clin Invest 2003; 112:1383-94.
45. Winau F, Hegasy G, Weiskirchen R, et al. Ito cells are liver-resident antigen-presenting cells for activating T cell responses. Immunity 2007; 26:117-29.
46. Fallowfield J A, Mizuno M, Kendall T J, et al. Scar-associated macrophages are a major source of hepatic matrix metalloproteinase-13 and facilitate the resolution of murine hepatic fibrosis. J Immunol 2007; 178:5288-95.
47. Kisseleva T, Brenner D A. Hepatic stellate cells and the reversal of fibrosis. J Gastroenterol Hepatol 2006; 21 Suppl 3:S84-7.
48. Kisseleva T, Uchinami H, Feirt N, et al. Bone marrow-derived fibrocytes participate in pathogenesis of liver fibrosis. J Hepatol 2006; 45:429-38.
49. Higashiyama R, Moro T, Nakao S, et al. Negligible Contribution of Bone Marrow-Derived Cells to Collagen Production During Hepatic Fibrogenesis in Mice. Gastroenterology 2009.
50. Tuchweber B, Desmouliere A, Bochaton-Piallat M L, et al. Proliferation and phenotypic modulation of portal fibroblasts in the early stages of cholestatic fibrosis in the rat. Lab Invest 1996; 74:265-78.
51. Guyot C, Lepreux S, Combe C, et al. Hepatic fibrosis and cirrhosis: the (myo)fibroblastic cell subpopulations involved. Int J Biochem Cell Biol 2006; 38:135-51.
52. Kinnman N, Francoz C, Barbu V, et al. The myofibroblastic conversion of peribiliary fibrogenic cells distinct from hepatic stellate cells is stimulated by platelet-derived growth factor during liver fibrogenesis. Lab Invest 2003; 83:163-73.
53. Dudas J, Mansuroglu T, Batusic D, et al. Thy-1 is an in vivo and in vitro marker of liver myofibroblasts. Cell Tissue Res 2007; 329:503-14.
54. Yovchev M I, Zhang J, Neufeld D S, et al. Thymus cell antigen-1-expressing cells in the oval cell compartment. Hepatology 2009; 50:601-11.
55. Wells R G, Kruglov E, Dranoff J A. Autocrine release of TGF-beta by portal fibroblasts regulates cell growth. FEBS Lett 2004; 559:107-10.
56. Knittel T, Kobold D, Saile B, et al. Rat liver myofibroblasts and hepatic stellate cells: different cell populations of the fibroblast lineage with fibrogenic potential. Gastroenterology 1999; 117:1205-21.
57. Kisseleva T, et al. (2011) Fibrocyte-like cells recruited to the spleen support innate and adaptive immune responses to acute injury or infection. *Journal of molecular medicine* 89(10):997-1013.
58. Scholten D, et al. (2011) Migration of fibrocytes in fibrogenic liver injury. *Am J Pathol* 179(1):189-198.
59. Kalluri R. EMT: when epithelial cells decide to become mesenchymal-like cells. J Clin Invest 2009; 119:1417-9.
60. Choi S S, Diehl A M. Epithelial-to-mesenchymal transitions in the liver. Hepatology 2009.
61. Taura K, Miura K, Iwaisako K, et al. Hepatocytes do not undergo epithelial-mesenchymal transition in liver fibrosis in mice. Hepatology 2010; 51:1027-36.
62. Scholten D, Osterreicher C H, Scholten A, et al. Genetic labeling does not detect epithelial-to-mesenchymal transition of cholangiocytes in liver fibrosis in mice. Gastroenterology 2010; 139:987-98.
63. Chu A S, Diaz R, Hui J J, et al. Lineage tracing demonstrates no evidence of cholangiocyte epithelial-to-mesenchymal transition in murine models of hepatic fibrosis. Hepatology 2011; 53:1685-95.

64. Dranoff J A & Wells R G (2010) Portal fibroblasts: Underappreciated mediators of biliary fibrosis. *Hepatology* 51(4):1438-1444.
65. Bhunchet E, Wake K. Role of mesenchymal cell populations in porcine serum-induced rat liver fibrosis. Hepatology 1992; 16:1452-73.
66. Desmouliere A, Darby I, Costa A M, et al. Extracellular matrix deposition, lysyl oxidase expression, and myofibroblastic differentiation during the initial stages of cholestatic fibrosis in the rat. Lab Invest 1997; 76:765-78.
67. Uchio K, Tuchweber B, Manabe N, et al. Cellular retinol-binding protein-1 expression and modulation during in vivo and in vitro myofibroblastic differentiation of rat hepatic stellate cells and portal fibroblasts. Lab Invest 2002; 82:619-28.
68. Wen J W, Olsen A L, Perepelyuk M, & Wells R G (2012) Isolation of rat portal fibroblasts by in situ liver perfusion. *Journal of visualized experiments: JoVE* (64).
69. Kruglov E A, Jain D, & Dranoff J A (2002) Isolation of primary rat liver fibroblasts. *J Investig Med* 50(3):179-184.
70. Clouzeau-Girard H, et al. (2006) Effects of bile acids on biliary epithelial cell proliferation and portal fibroblast activation using rat liver slices. *Lab Invest* 86(3):275-285.
71. Clouzeau-Girard H, Guyot C, Combe C, et al. Effects of bile acids on biliary epithelial cell proliferation and portal fibroblast activation using rat liver slices. Lab Invest 2006; 86:275-85.
72. Goodpaster T, Legesse-Miller A, Hameed M R, et al. An immunohistochemical method for identifying fibroblasts in formalin-fixed, paraffin-embedded tissue. J Histochem Cytochem 2008; 56:347-58.
73. Dranoff J A, Kruglov E A, Robson S C, et al. The ecto-nucleoside triphosphate diphosphohydrolase NTPDase2/CD39L1 is expressed in a novel functional compartment within the liver. Hepatology 2002; 36:1135-44.
74. Bosselut N, Housset C, Marcelo P, et al. Distinct proteomic features of two fibrogenic liver cell populations: hepatic stellate cells and portal myofibroblasts. Proteomics; 10: 1017-28.
75. Fausther, M. & Dranoff, J. A. New insights on the pathogenesis of biliary cirrhosis provided by studies in FXR knockout mice. *J Hepatol* 55, 939-940 (2011).
76. Chang, K. & Pastan, I. Molecular cloning of mesothelin, a differentiation antigen present on mesothelium, mesotheliomas, and ovarian cancers. *Proc Natl Acad Sci USA* 93, 136-140 (1996).
77. Grigoriu, B. D., Grigoriu, C., Chahine, B., Gey, T. & Scherpereel, A. Clinical utility of diagnostic markers for malignant pleural mesothelioma. *Monaldi Arch Chest Dis* 71, 31-38 (2009).
78. Bera, T. K. & Pastan, I. Mesothelin is not required for normal mouse development or reproduction. *Mol Cell Biol* 20, 2902-2906 (2000).
79. Rinkevich, Y., et al. Identification and prospective isolation of a mesothelial precursor lineage giving rise to smooth muscle cells and fibroblasts for mammalian internal organs, and their vasculature. *Nature cell biology* 14, 1251-1260 (2012).
80. Li, Y., Wang, J. & Asahina, K. Mesothelial cells give rise to hepatic stellate cells and myofibroblasts via mesothelial-mesenchymal transition in liver injury. *Proc Natl Acad Sci USA* 110, 2324-2329 (2013).
81. Asahina, K., Zhou, B., Pu, W. T. & Tsukamoto, H. Septum transversum-derived mesothelium gives rise to hepatic stellate cells and perivascular mesenchymal cells in developing mouse liver. Hepatology 53, 983-995 (2011).
82. Fort, M. M., et al. IL-25 induces IL-4, IL-5, and IL-13 and Th2-associated pathologies in vivo. *Immunity* 15, 985-995 (2001).
83. Gregory, L. G., et al. IL-25 drives remodelling in allergic airways disease induced by house dust mite. *Thorax* (2012).
84. Wynn, T. A. IL-13 effector functions. *Annu Rev Immunol* 21, 425-456 (2003).
85. Liu, Y., et al. IL-13 induces connective tissue growth factor in rat hepatic stellate cells via TGF-beta-independent Smad signaling. *J Immunol* 187, 2814-2823 (2011).
86. Kawada, N., et al. Characterization of a stellate cell activation-associated protein (STAP) with peroxidase activity found in rat hepatic stellate cells. *J Biol Chem* 276, 25318-25323 (2001)
87. Forbes, S. J. & Parola, M. Liver fibrogenic cells. *Best Pract Res Clin Gastroenterol* 25, 207-217 (2011).
88. Onitsuka, I., Tanaka, M. & Miyajima, A. Characterization and functional analyses of hepatic mesothelial cells in mouse liver development. *Gastroenterology* 138, 1525-1535, 1535 e1521-1526 (2010).
89. Bochmann, L., et al. Revealing new mouse epicardial cell markers through transcriptomics. *PLoS One* 5, e11429 (2010).
90. Asahina, K. Hepatic stellate cell progenitor cells. *Journal of gastroenterology and hepatology* 27 Suppl 2, 80-84 (2012).
91. Meurer, S. K., et al. Overexpression of endoglin modulates TGF-beta1-signalling pathways in a novel immortalized mouse hepatic stellate cell line. *PLoS One* 8, e56116 (2013)
92. Wang, Y., Wang, L., Li, D., Wang, H. B. & Chen, Q. F. Mesothelin promotes invasion and metastasis in breast cancer cells. *The Journal of international medical research* 40, 2109-2116 (2012).
93. Derso, K., et al. Thy-1 is expressed in hepatic myofibroblasts and not oval cells in stem cell-mediated liver regeneration. *Am J Pathol* 171, 1529-1537 (2007).
94. Hagood, J. S., et al. Loss of fibroblast Thy-1 expression correlates with lung fibrogenesis. *Am J Pathol* 167, 365-379 (2005).
95. Dooley, S., et al. Smad7 prevents activation of hepatic stellate cells and liver fibrosis in rats. *Gastroenterology* 125, 178-191 (2003).
96. Cheon, D. J., et al. CA125/MUC16 is dispensable for mouse development and reproduction. *PLoS One* 4, e4675 (2009).
97. Shimizu, A., et al. Coexpression of MUC16 and mesothelin is related to the invasion process in pancreatic ductal adenocarcinoma. *Cancer science* 103, 739-746 (2012).
98. Rinkevich, Y., et al. Identification and prospective isolation of a mesothelial precursor lineage giving rise to smooth muscle cells and fibroblasts for mammalian internal organs, and their vasculature. *Nature cell biology* 14, 1251-1260 (2012).

All publications, patent applications, patents, and other references mentioned herein are incorporated by reference in their entireties.

We claim:

1. A method for treating or attenuating cholestatic liver fibrosis in a subject in need thereof comprising administering to said subject a therapeutic amount of an anti-mesothelin antibody or antigen binding fragment thereof capable of inhibiting the activity of mesothelin, wherein the anti-mesothelin antibody or antigen binding fragment thereof comprises: a $V_H$ chain comprising CDRs 1, 2, and 3 having the amino acid sequence set forth in SEQ ID NOS: 1, 2 and 3, respectively and a $V_L$ chain comprising CDRs 1, 2, and 3 having the amino acid sequence set forth in SEQ ID NOS:4, 5 and 6, respectively; or a $V_H$ chain comprising CDRs 1, 2, and 3 having the amino acid sequence set forth in SEQ ID NOS: 7, 8, and 9, respectively and a $V_L$ chain comprising CDRs 1, 2, and 3 having the amino acid sequence set forth in SEQ ID NOS: 10, 11 and 12, respectively, wherein the antibody or antigen binding fragment thereof specifically binds to mesothelin, thereby treating or attenuating the cholestatic liver fibrosis.

2. The method of claim 1, wherein the anti-mesothelin antibody or antigen binding fragment thereof is a conjugate.

3. The method of claim 2, wherein the conjugate comprises an immunotoxin.

4. The method of claim 1, wherein the anti-mesothelin antibody or antigen binding fragment thereof is given in combination with an additional active agent.

5. The method of claim 4, wherein the additional active agent comprises tauroursodeoxycholic acid.

6. The method of claim 4, wherein the additional active agent comprises a corticosteroid.

7. The method of claim 1, wherein the anti-mesothelin antibody or antigen binding fragment thereof is a recombinant polypeptide.

8. The method of claim 1, wherein the subject is a human.

9. The method of claim 1, wherein the subject is a non-human primate.

10. The method of claim 1, wherein the cholestatic liver fibrosis is partially inhibited or reduced.

11. The method of claim 1, wherein the administering to said subject the therapeutic amount of the anti-mesothelin antibody or antigen binding fragment thereof reduces the severity of the cholestatic liver fibrosis.

12. The method of claim 1, wherein the administering to said subject the therapeutic amount of the anti-mesothelin antibody or antigen binding fragment thereof retards or slows the progression of the cholestatic liver fibrosis.

13. The method of claim 4, wherein the additional active agent comprises an antifibrotic.

14. The method of claim 4, wherein the additional active agent comprises an anti-inflammatory.

15. The method of claim 4, wherein the additional active agent comprises an immunosuppressant.

16. The method of claim 4, wherein the additional active agent comprises a chemotherapeutic agent.

17. The method of claim 4, wherein the additional active agent comprises an anti-metabolite.

18. The method of claim 4, wherein the additional active agent comprises an immunomodulator.

19. The method of claim 9, wherein the non-human primate is a dog, a cat, a horse or a mouse.

20. The method of claim 7, wherein the recombinant antigen binding fragment comprises a humanized antibody.

21. The method of claim 1, wherein the $V_H$ chain and the $V_L$ chain are linked by a peptide linker to form a scFv, or the $V_H$ chain and the $V_L$ chain have one or more cysteine residues engineered into a framework region to permit formation of a disulfide bond linking the $V_H$ chain and the $V_L$ chain together.

* * * * *